US009849124B2

(12) United States Patent
Hummel et al.

(10) Patent No.: US 9,849,124 B2
(45) Date of Patent: Dec. 26, 2017

(54) SYSTEMS AND METHODS FOR TREATING AN OPIOID-INDUCED ADVERSE PHARMACODYNAMIC RESPONSE

(71) Applicant: Purdue Pharma L.P., Stamford, CT (US)

(72) Inventors: Michele Hummel, Marlton, NJ (US); Donald J. Kyle, Yardley, PA (US); Garth Whiteside, Yardley, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 14/885,597

(22) Filed: Oct. 16, 2015

(65) Prior Publication Data
US 2016/0106735 A1    Apr. 21, 2016

Related U.S. Application Data

(60) Provisional application No. 62/065,399, filed on Oct. 17, 2014.

(51) Int. Cl.
*A61K 31/485* (2006.01)
*A61K 9/20* (2006.01)
*A61K 9/48* (2006.01)
*A61K 9/70* (2006.01)

(52) U.S. Cl.
CPC .......... *A61K 31/485* (2013.01); *A61K 9/2004* (2013.01); *A61K 9/4816* (2013.01); *A61K 9/7023* (2013.01)

(58) Field of Classification Search
CPC .................................................. A61K 31/485
USPC ....................................................... 514/282
See application file for complete search history.

(56) References Cited

U.S. PATENT DOCUMENTS

| | | | |
|---|---|---|---|
| 3,965,256 A | 6/1976 | Leslie | |
| 4,235,870 A | 11/1980 | Leslie | |
| 4,443,428 A | 4/1984 | Oshlack et al. | |
| 4,588,580 A | 5/1986 | Gale et al. | |
| 4,769,372 A | 9/1988 | Kreek et al. | |
| 4,785,000 A | 11/1988 | Kreek et al. | |
| 4,834,984 A | 5/1989 | Goldie et al. | |
| 4,844,909 A | 7/1989 | Goldie et al. | |
| 4,861,598 A | 8/1989 | Oshlack | |
| 4,970,075 A | 11/1990 | Oshlack | |
| 4,987,136 A | 1/1991 | Kreek et al. | |
| 4,990,341 A | 2/1991 | Goldie et al. | |
| 5,266,331 A | 11/1993 | Oshlack et al. | |
| 5,273,760 A | 12/1993 | Oshlack et al. | |
| 5,286,493 A | 2/1994 | Oshlack et al. | |
| 5,324,351 A | 6/1994 | Oshlack et al. | |
| 5,356,467 A | 10/1994 | Oshlack et al. | |
| 5,411,745 A | 5/1995 | Oshlack et al. | |
| 5,472,712 A | 12/1995 | Oshlack et al. | |
| 5,478,577 A | 12/1995 | Sackler et al. | |
| 5,500,227 A | 3/1996 | Oshlack et al. | |
| 5,508,042 A | 4/1996 | Oshlack et al. | |
| 5,549,912 A | 8/1996 | Oshlack et al. | |
| 5,580,578 A | 12/1996 | Oshlack et al. | |
| 5,639,476 A | 6/1997 | Oshlack et al. | |
| 5,656,295 A | 8/1997 | Oshlack et al. | |
| 5,672,360 A | 9/1997 | Sackler et al. | |
| 5,681,585 A | 10/1997 | Oshlack et al. | |
| 5,843,480 A | 12/1998 | Miller et al. | |
| 5,849,240 A | 12/1998 | Miller et al. | |
| 5,891,471 A | 4/1999 | Miller et al. | |
| 5,914,131 A | 6/1999 | Merrill et al. | |
| 5,958,452 A | 9/1999 | Oshlack et al. | |
| 5,965,161 A | 10/1999 | Oshlack et al. | |
| 5,965,163 A | 10/1999 | Miller et al. | |
| 5,968,547 A | 10/1999 | Reder et al. | |
| 5,968,551 A | 10/1999 | Oshlack et al. | |
| 6,024,982 A | 2/2000 | Oshlack et al. | |
| 6,143,322 A | 11/2000 | Sackler et al. | |
| 6,162,467 A | 12/2000 | Miller et al. | |
| 6,210,714 B1 | 4/2001 | Oshlack et al. | |
| 6,228,863 B1 | 5/2001 | Palermo et al. | |
| 6,277,384 B1 | 8/2001 | Kaiko et al. | |
| 6,344,212 B2 | 2/2002 | Reder et al. | |
| 6,375,957 B1 | 4/2002 | Kaiko et al. | |
| 6,572,885 B2 | 6/2003 | Oshlack et al. | |
| 6,696,066 B2 | 2/2004 | Kaiko et al. | |
| 6,696,088 B2 | 2/2004 | Oshlack et al. | |
| 6,733,783 B2 | 5/2004 | Oshlack et al. | |
| 7,141,250 B2 | 11/2006 | Oshlack et al. | |
| 7,144,587 B2 | 12/2006 | Oshlack et al. | |
| 7,157,103 B2 | 1/2007 | Sackler | |
| 7,332,182 B2 | 2/2008 | Sackler | |

(Continued)

FOREIGN PATENT DOCUMENTS

DE  10 2010 048 883   4/2012
EP        1958621      8/2008

(Continued)

OTHER PUBLICATIONS

US Dept. of Health and Human Services (DHHS), Publ. No. SMA 09-4376 (2009) pp. 1-104.*
Guide to Physcians: DHHS Publ. No. (SMA) 05-4003 (2005), pp. 1-35.*
Alhaddad, H., et al., "Respiratory toxicity of buprenorphine results from the blockage of Pglycoprotein-mediated efflux of norbuprenorphine at the blood-brain barrier in mice," Critical Care Medicine, vol. 40, No. 12, pp. 3215-3223, Dec. 2012.
Aurilio, B., et al., "Transdermal buprenorphine combined with spinal morphine and naropine for pain relief in chronic peripheral vasculopathy," Minerva Anestesiologica, vol. 71, No. 7-8, pp. 445-449, Jul.-Aug. 2005.
Beltrutti, D., et al., "Late Antinociception and Lower Untoward Effects of Concomitant Intrathecal Morphine and Intravenous Buprenorphine in Humans," Journal of Clinical Anesthesia, vol. 14, No. 6, pp. 441-446, Sep. 2002.

(Continued)

*Primary Examiner* — Taofiq A Solola
(74) *Attorney, Agent, or Firm* — Lowenstein Sandler LLP

(57) ABSTRACT

Disclosed in certain embodiments is a method of treating or preventing an opioid induced adverse pharmacodynamic response comprising administering to a patient in need thereof an effective amount of buprenorphine.

16 Claims, 29 Drawing Sheets

(56) References Cited

U.S. PATENT DOCUMENTS

| | | |
|---|---|---|
| 7,674,799 B2 | 3/2010 | Chapman et al. |
| 7,674,800 B2 | 3/2010 | Chapman et al. |
| 7,683,072 B2 | 3/2010 | Chapman et al. |
| 7,727,557 B2 | 6/2010 | Sackler |
| RE41,489 E | 8/2010 | Reder et al. |
| RE41,571 E | 8/2010 | Reder et al. |
| 7,842,307 B2 | 11/2010 | Oshlack et al. |
| 7,842,311 B2 | 11/2010 | Oshlack et al. |
| 7,943,174 B2 | 5/2011 | Oshlack et al. |
| 8,017,148 B2 | 9/2011 | Sackler |
| 8,337,888 B2 | 12/2012 | Wright et al. |
| 8,389,007 B2 | 3/2013 | Wright et al. |
| 8,524,275 B2 | 9/2013 | Oshlack et al. |
| 8,529,948 B1 | 9/2013 | Wright et al. |
| 8,551,520 B2 | 10/2013 | Oshlack et al. |
| 8,609,683 B2 | 12/2013 | Wright et al. |
| 8,647,667 B2 | 2/2014 | Oshlack et al. |
| 8,652,497 B2 | 2/2014 | Sackler |
| 8,652,515 B2 | 2/2014 | Sackler |
| 8,673,355 B2 | 3/2014 | Kaiko et al. |
| 8,822,487 B2 | 9/2014 | Kaiko et al. |
| 8,846,090 B2 | 9/2014 | Brögmann et al. |
| 8,846,091 B2 | 9/2014 | Brögmann et al. |
| 8,946,253 B2 | 2/2015 | Hummel et al. |
| 8,969,369 B2 | 3/2015 | Caruso et al. |
| 9,211,293 B2 | 12/2015 | Deaver et al. |
| 9,233,073 B2 | 1/2016 | Sackler |
| 2001/0031278 A1 | 10/2001 | Oshlack et al. |
| 2002/0010127 A1 | 1/2002 | Oshlack et al. |
| 2003/0064099 A1 | 4/2003 | Oshlack et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0124185 A1 | 7/2003 | Oshlack et al. |
| 2003/0187010 A1 | 10/2003 | Foss et al. |
| 2004/0047907 A1 | 3/2004 | Oshlack et al. |
| 2004/0266807 A1 | 12/2004 | Oshlack et al. |
| 2005/0063909 A1 | 3/2005 | Wright et al. |
| 2007/0020339 A1 | 1/2007 | Bear |
| 2009/0246265 A1 | 10/2009 | Stinchcomb et al. |
| 2010/0152222 A1 | 6/2010 | Chapleo et al. |
| 2010/0227876 A1 | 9/2010 | Rech |
| 2010/0284960 A1 | 11/2010 | Riggs-Sauthier |
| 2011/0097395 A1 | 4/2011 | Babul et al. |
| 2011/0245287 A1 | 10/2011 | Holaday et al. |
| 2011/0262532 A1 | 10/2011 | Oshlack et al. |
| 2012/0164220 A1 | 6/2012 | Huang |
| 2012/0178771 A1 | 7/2012 | Babul et al. |
| 2013/0281388 A1 | 10/2013 | Deaver et al. |
| 2014/0056979 A1 | 2/2014 | Huang |

FOREIGN PATENT DOCUMENTS

| | | |
|---|---|---|
| RU | 2012122945 | 12/2013 |
| WO | 9602251 | 2/1996 |
| WO | 2004054554 | 7/2004 |
| WO | 2005011579 | 2/2005 |
| WO | WO-2006/087160 | 8/2006 |
| WO | 2006089973 | 12/2006 |
| WO | 2007005716 | 1/2007 |
| WO | 2010141505 | 12/2010 |
| WO | 2011109743 | 9/2011 |
| WO | WO-2012/166998 | 6/2012 |

OTHER PUBLICATIONS

Beltrutti, D., et al., "Pain relief after simultaneous administration of intravenous buprenorphine and intrathecal morphine in terminally ill patients; A report of two cases," The Pain Clinic, vol. 12, No. 2, pp. 121-123, Jun. 2000.

Ben-Abraham, R., et al., "The benefit of combining spinal morphine and intravenous buprenorphine for perioperative pain," vol. 140, No. 8, pp. 709-712, Aug. 2001, Abstract.

Bickel, et al., "Buprenorphine: Dose-Related Blockade of Opioid Challenge Effects in Opioid Dependent Humans,The Journal of Pharmacology and Experimental Therapeutics", 1988, pp. 47-53, vol. 247, No. 1, The AmericanSociety for Pharmacology and Experimental Therapeutics, United States.

"Buprenorphine: A Guide for Nurses," Technical Assistance Publication (TAP) Series, Substance Abuse and Mental Health Services Administration, 2009, pp. 1-104, DHHS Publication No. (SMA) 09-4376.

"Clinical Guidelines for the Use of Buprenorphine in the Treatment of Opioid Addiction," Quick Guide for Physicians Based on TIP 40, 2005, pp. 1-35, U.S. Department of Health and Human Services, DHHS Publication No. (SMA) 05-4003.

Chen, L.H., et al., "Interaction of combined administration of intrathecal morphine with subcutaneous morphine or buprenorphine," Acta Pharmacologica Sinica, vol. 21, No. 8, pp. 685-689, Aug. 2000.

Chung, C.Y., et al., "Analgesic properties of loperamide differ following systemic and local administration to rats after spinal nerve injury," European Journal of Pain, vol. 16, No. 7, pp. 1021-1032, Aug. 2012.

Elkader, et al., "Buprenorphine Clinical Pharmacokinetics in the Treatment of Opioid Dependence", 2005, pp. 661-680, vol. 44, No. 7, Adis Data Information BV, Canada.

Fickel, J.,et al., "Opioid receptor expression in the rat gastrointestinal tract: a quantitative study with comparison to the brain," Molecular Brain Research, vol. 46, No. 1-2, pp. 1-8, Jun. 1997.

Huang, P., et al., "Comparison of Pharmacological Activities of Buprenorphine and Norbuprenorphine: Norbuprenorphine is a Potent Opioid Agonist," The Journal of Pharmacology and Experimental Therapeutics, vol. 297, No. 2, pp. 688-695, May 2001.

International Search Report dated Jul. 12, 2013 from PCT App. No. PCT/IB2013/000746 filed Apr. 17, 2013.

International Preliminary Report on Patentability dated Nov. 14, 2014 from PCT App. No. PCT/IB2013/000746 filed Apr. 17, 2013.

International Search Report and Written Opinion dated Jan. 16, 2016 for International Application No. PCT/US15/49948 filed Sep. 14, 2015, 9 pgs.

Jasinski, et al., "Human Pharmacology and Abuse Potential of the Analgesic Buprenorphine", Arch Gen Psychiatry, Apr. 1978, pp. 501-516, vol. 35, Arch Gen Psychiatry, United States.

Jensen, M.L., et al., "Comparison of cerebral pharmacokinetics of buprenorphine and norbuprenorphine in an in vivo sheep model," Xenobiotica, vol. 37, No. 4, pp. 441-457, Apr. 2007.

Jones, et al., "The Subjective, Reinforcing, and Analgesic Effects of Oxycodone in Patients with Chronic, Non-Malignant Pain who are Maintained on Sublingual Buprenorphine/Naloxone, Neuropsychopharmacology", 2011, pp. 11-422, vol. 36, American College of Neuropsychopharmacology, United States.

Kogel, B., et al., "Interaction of mu-Opioid Receptor Agonists and Antagonists with the Analgesic Effect of Buprenorphine in Mice," European Journal of Pain, vol. 9, pp. 599-611, Oct. 2005.

Kopper W. et al., "Different profiles of buprenorphine-induced analgesia and antihyperalgesia in a human pain model", Pain 118 (2005), pp. 15-22.

Megarbane, B., et al., "Buprenorphine is protective against the depressive effects of norbuprenorphine on ventilation," Toxicology and Applied Pharmacology, vol. 212, No. 3, pp. 256-267, May 2006.

Mendelson, et al., "Bioavailability of Sublingual Buprenorphine", Journal Clinical Pharmacology, 1997, pp. 31-37, Vo. 37, SAGE Social Science Collections, United States.

Mercadante, S., et al., "Safety and Effectiveness of Intravenous Morphine for Episodic Breakthrough Pain in Patients Receiving Transdermal Buprenorphine," Journal of Pain and Symptom Management, vol. 32, No. 2, pp. 175-179, Aug. 2006.

Morgan, D., et al., "An Examination of the Interactions between the Antinociceptive Effects of Morphine and Various mu-Opioids: The Role of Intrinsic Efficacy and Stimulus Intensity," Anesthesia & Analgesia, vol. 88, No. 2, pp. 407-413, Feb. 1999.

Niv, D., et al., "Antinociceptive Effect Induced by the Combined Administration of Spinal Morphine and Systemic Buprenorphine," Anesthesia & Analgesia, vol. 87, No. 3, pp. 583-586, Sep. 1998.

(56) References Cited

OTHER PUBLICATIONS

Parker, R.K., et al., "Patient-Controlled Epidural Analgesia: Interactions between Nalbuphine and Hydromorphone," Anesthesia & Analgesia, vol. 84, No. 4, pp. 757-763, Apr. 1997.
Pick, C.G., et al., "Pharmacological Characterization of Buprenorphine, a Mixed Agonist-Antagonist with kappa3 Analgesia," Brian Research, vol. 744, pp. 41-46, Jan. 1997.
Purdue Pharma LP, "BUTRANS—buprenorphine patch, extended release," available at http://app.purduepharma.com/xmlpublishing/pi.aspx?id=b, pp. 1-43, Jun. 2014.
Ramasubbu, C., et al., "Pharmacological Treatment of Opioid-Induced Hyperalgesia: A Review of the Evidence," Journal of Pain & Palliative Care Pharmacotherapy, vol. 25, No. 3, pp. 219-230, Aug. 2011.
Rosen, et al., "Buprenorphine: duration of blockade of effects of intramuscular hydromorphone", Drug and Alcohol Dependence 1994, pp. 141-149, vol. 35, Elsevier, Ireland.
Rosti, G., et al., "Opioid-Related Bowel Dysfunction: Prevalence and Identification of Predictive Factors in a Large Sample of Italian Patients on Chronic Treatment," European Review for Medical and Pharmacological Sciences, vol. 14, No. 12, pp. 1045-1050, Dec. 2010.
Teoh, S.K., et al., "Buprenorphine Effects on Morphine- and Cocaine- Induced Subjective Responses by Drug-Dependent Men," Journal of Clinical Psychopharmacology, vol. 14, No. 1, pp. 15-27, Feb. 1994.
Virk, M.S., et al., "Buprenorphine is a Weak Partial Agonist That Inhibits Opioid Receptor Desensitization," The Journal of Neuroscience, vol. 29, No. 22, pp. 7341-7348, Jun. 2009.
Walker, E.A., et al., "Buprenorphine Antagonism of Mu Opioids in the Rhesus Tail-Withdrawal Procedure," Journal of Pharmacology and Experimental Therapeutics, vol. 273, No. 3, pp. 1345-1352, Jun. 1995.
Walsh, S.L., et al., "Acute Administration of Buprenorphine in Humans: Partial Agonist and Blockade Effects," The Journal of Pharmacology and Experimental Therapeutics, vol. 274, No. 1, pp. 361-372, Jul. 1995.
Written Opinion dated Jul. 12, 2013 from PCT App. No. PCT/IB2013/000746 filed Apr. 17, 2013.
Yassen, A., et al., "Pharmacokinetic-Pharmacodynamic Modeling of the Respiratory Depressant Effect of Norbuprenorphine in Rats," The Journal of Pharmacology and Experimental Therapeutics, vol. 321, No. 2, pp. 598-607, May 2007.
Ben-Abraham, Ron, et al., "The Efficacy of the Combination of Intrathecal Morphine and Intravenous Buprenorphine for Postoperative Pain," Harefuah, vol. 140, No. 8, 2001, pp. 709-712—Certified English translation Thereof.
Bruzgin, V. V., "Treatment of Chronic Pain Syndrome in Patients with Generalized Forms of Breast Cancer," Tumors of the Femal Reproductive System, vol. 3, 2007, pp. 6-10—Certified English Translation Thereof.
Pchelintcev, M., "Combination preparation, comrpising opioids and antagonists of opioids receptors, in increasing safety of treatment of intensive pain," Vrach Nov. 2012, pp. 38-42—English Translation Thereof.
Pchelintcev, M. V., "The Role of Ketamine in the Analgesic Effect of the Combination of Fentanyl and Buprenorphine in a Thermal Nociception Model in Mice," Proceedings of St. Petersburg State Medical University Named After Academician I.P. Pavlov, vol. 17, No. 2, 2010, pp. 59-62—Certified English Translation Thereof.
U.S. Appl. No. 13/864,791, filed Apr. 17, 2013.
U.S. Appl. No. 14/562,170, filed Dec. 5, 2014.
U.S. Appl. No. 14/612,941, filed Feb. 3, 2015.
U.S. Appl. No. 14/632,152, filed Feb. 26, 2015.
U.S. Appl. No. 14/669,475, filed Mar. 26, 2015.
U.S. Appl. No. 14/669,481, filed Mar. 26, 2015.
U.S. Appl. No. 14/669,486, filed Mar. 26, 2015.
U.S. Appl. No. 14/669,490, filed Mar. 26, 2015.
U.S. Appl. No. 14/669,496, filed Mar. 26, 2015.
U.S. Appl. No. 14/669,499, filed Mar. 26, 2015.

Boysen K, Hertel S, Chraemmer-Jorgensen B, Risbo a, Poulsen NJ: Buprenorphine antagonism of ventilatory depression following fentanyl anaesthesia. Acta Anaesthesiol Scand 1988;32:490-2.
Sittl, et al., "Changes in the Prescribed Daily Doses of Transdermal Fentanyl and Transdermal Buprenorphine During Treatment of Patients with Cancer and Noncancer Pain in Germany: Results of Retrospective Cohort Study," Clinical Therapeutics, vol. 27, No. 7, (2005) pp. 1022-1031.
Dahan, A. et al, Incidence, Reversal, and Prevention of Opioid-induced Respiratory Depression, The American Society of Anesthesiologists, Inc., Jan. 2010, Anestesiology, vol. 112, No. 1; 112-226-38.
Dahan, A. et al., Buprenorphine induces ceiling in respiratory depression but not in analgesia, Advanced Access publication, Mar. 2017, 2006, British Journal of Anesthesia 96 (5); 627-632.
Dahan, A. Opoid-induced respiratory effects: new data on buprenorphine, Palliative Medicine 2006, vol. 20; s3-s8.
Liang Zhou; Liang Sun; Haiyan Wang; Yanpeng Dong; Linxin Wu; Li Sun, "Efficacy of combination of morphine sulfate controlled-release tablet and buprenorphine sublingual tablet in moderate to severe cancer pain patient", Intl. J. Anesth. Resus, Feb. 2015, (36)2, 113-116; and it's English translation thereof.
M. Kwarcinski; M. Cataldo; C. Munera; B. Dain, "The use of immediate-release opioids as supplemental analgesia during the management of moderate to severe chronic pain with transdermal buprenorphine, a partial mu-opioid receptor agonist.", Journal of the American Pharmacists Association, (Mar.-Apr. 2012) vol. 52, No. 2, p. 284.
M.V. Pchelintcev, "The Role of Ketamine in the Analgesic Effect of the Combination of Fentanyl and Buprenorphine in a Thermal Nociception Model in Mice", Scientific notes of the Saint Petersburg State Medical University named after acad. Pavlov. Volume XVII No. 2, 2010.
Nemirovsky A et al., Antinociceptive effect of combined administration of spinal morphine and systemic buprenorphine, Anesthesiology (Hagerstown), (Sep., 1998) vol. 89, No. 3A, p. A1087.
Nemirovsky A et al., Antinociceptive effect of the combinations of spinal morphine and systemic morphine or buprenorphine, FASEB Journal, Mar. 17, 1998, vol. 12, No. 4, p. A156, Abstract No. 911.
Nemirovsky A et al., Mutual antagonism of buprenorphine and morphine as evidenced in the nociceptive activity evoked in thalamus neurons of the rat, Anesthesiology, (Sep. 2000) vol. 93, No. 3A, Supp. [S], pp. U192-U192.
Nemirovsky A, Chen L, Zelman V, Jurna I: The antinociceptive effect of the combination of spinal morphine with systemic morphine or buprenorphine. Anesth Analg 2001;93:197-203.
Oifa, S., et al., "Effects of Intravenous Patient-Controlled Analgesia with Burprenorphine and Morphine Alone and in COmbination during the First 12 Postoperative Hours: A Randomized, Double-Blind, Four-Arm Tiral in Adults Undergoing Abdominal Surgery," Clinical Therapeutics 31.3 (2009), pp. 527-41.
Pergolizzi Joseph et al., Current knowledge of buprenorphine and its unique pharmacological profile, Pain practice : the official journal of World Institute of Pain, (Sep.-Oct. 2010) vol. 10, No. 5, pp. 428-50.
Revere E. et al., Controlled-release oxycodone tablets after transdermal-based opioid therapy in patients with cancer and non-cancer pain, Aging clinical and experimental research, (Oct.-Dec. 2011) vol. 23, No. 5-6, pp. 328-32.
Sharon L. Walsh et al., "Intranasal buprenorphine alone and in combination with naloxone: Abuse liability and reinforcing efficacy in physically dependent opioid abusers.", Drug and Alcohol Dependence, (May 1, 2016) vol. 162, pp. 190-198.
Troster, Interaction of fentanyl and buprenorphine in an experimental model of pain and central sensitization in human volunteers, Clinical J. of Pain, (2013) vol. 28 p. 705-11.
Zanette G, Manani G, Giusti F, et al. Respiratory depression following administration of low dose buprenorphine as postoperative analgesic after fentanyl balanced anaesthesia.
Van der Shier, R. et al, Opoid-induced respritaroy depression: reversal by non-opioid drugs, F1000Prime Reports, Sep. 4, 2014, 6:79, pp. 1-8.

(56) References Cited

OTHER PUBLICATIONS

Vedig AE, Gibbs jM, Rutten Aj, Ilsley AH. The effect ofbuprenorphine on the analgesic and respiratory depressant effects of pethidine: A preliminary study. Pain. 1988;34:253-259.

M. Pechlintsev, Ph.D., "Combinations of drugs containing opiates and opiate receptor antagonists, for increased safety of therapy in pain," Saint Petersburg State Medical Sciences named for academician I.P. Pavlov. (2012).

Afsharimani, B., et al., "Pharmacological options for the management of refractory cancer pain—what is the evidence?" Support Care Cancer, 2015, pp. 1473-1481, vol. 35, No. 4, Springer.

Ambros, Barbara, "Effect of pretreatment with hydromorphone or buprenorphine on thermal antinociception induced by fentanyl in awake cats," Journal of Feline Medicine and Surgery, 2016, pp. 818-825, vol. 18, No. 10, SAGE.

Berland, D., et al., "When Opioids Fail in Chronic Pain Management: The Role for Buprenorphine and Hospitalization," American Journal of Therapeutics, 2013, pp. 316-321, vol. 20, No. 4, Lippincott Williams & Wilkins.

Boas, R.A., et al., "Clinical Actions of Fentanyl and Buprenorphine," British Journal of Anaesthesia, 1985, pp. 192-196, vol. 57, No. 2.

Cordonnier, L., et al., "Blockade of morphine-induced behavioral sensitization by a combination of amisulpride and RB101, comparison with classical opioid maintenance treatments," British Journal of Pharmacology, 2007, pp. 94-102, vol. 151, Nature Publishing Group.

Cowan, A., et al., "Agonist and Antagonist Properties of Buprenorphine, A New Antinociceptive Agent," British Journal of Pharmacology, 1977, pp. 537-545, vol. 60.

Cowan, A., et al., "Buprenorphine—The Unique Opioid Analgesic," Pharmacology and Clinical Application, 2005, pp. 92-101, Thieme Medical Publishers, NY.

Davis, M., et al., "Twelve Reasons for Considering Buprenorphine as a Frontline Analgesic in the Management of Pain," The Journal of Support Oncology, Nov./Dec. 2012, pp. 209-219, vol. 10, No. 6.

Davis, M., et al., "Evidence from basic research for opioid combinations," Expert Opinion Drug Discovery, 2012, pp. 165-178, vol. 7, No. 2, Informa UK, Ltd.

De Barutell, C., et al., "Efficacy and safety of buprenorphine TDS in conjunction with oral tramadol or morphine as rescue medication in the treatment of 390 patients with chronic pain: A summary of two retrospective Spanish multicenter studies," Journal of Applied Therapeutic Research, 2007, pp. 14-24, vol. 6, No. 2, Euromed Communications.

Dum, J., et al., "In vivo Receptor Binding of the Opiate Partial Agonist, Buprenorphine, Correlated with its Agonistic and Antagonistic Actions," British Journal of Pharmacology, 1981, pp. 627-633, vol. 74, No. 3, Macmillian Publishers Ltd.

Filibeck, U., et al., "Differential Effects of Opiate Agonists-Antagonists on Morphine-Induced Hyperexcitability and Analgesia in Mice," Psychophamarmacology, 1981, pp. 134-136, vol. 73, Springer-Verlag.

Flecknell, P.A., et al., "Reversal of fentanyl/fluanisone neuroleptanalgesia in the rabbit using mixed agonist/antagonist opioids," Laboratory Animals, 1989, pp. 147-155, vol. 23.

Foltin, R., et al., "Interaction of Buprenorphine With cocaine—Morphine Combinations," Experimental and Clinical Psychoparacology, 1995, pp. 261-269, vol. 3, No. 3.

Freye, E., et al., "No potentiation of fentanyl by use of transdermal buprenorphine in patients undergoing fast-track anesthesia for open-heart surgery," Journal of Opioid Management, Jul./Aug. 2005, pp. 162-165, vol. 1.

Glover, E., et al., "Anxiolytic-like effects of morphine and buprenorphine in the rat model of fear-potentiated startle: tolerance, cross-tolerance, and blockade by naloxone," Psychopharmacology, 2008, pp. 167-180, vol. 198, No. 2, Springer-Verlag.

Gonzales-Escalada, J.R., "Concomitant use of transdermal buprenorphine and oral morphine in patients with chronic pain," Spanish Society for the Study of Pain, Dec. 2004, pp. 3-10, vol. 11, Suppl. V.

Griessinger, N., et al., "Transdermal buprenorphine in clinical practice—a post-marketing surveillance study in 13179 patients," Current Medical Research and Opinion, 2005, pp. 1147-1156, vol. 21, No. 8, Librapharm Limited.

Khanna, I., et al., "Buprenorphine—an attractive opioid with underutilized potential in treatment of chronic pain," Journal of Pain Research, 2015, pp. 859-870, vol. 8, Dovepress.

Kress, Hans, G., "Clinical update on the pharmacology, efficacy and safety of transdermal buprenorphine," European Journal of Pain, 2009, pp. 219-230, vol. 13, Elsevier.

Kuribara, H., et al., "The Ambulation-Increasing Effect of Buprenorphine in Mice: Comparison with the Effect of Morphine," Japanese Journal of Alcohol Studies and Drug Dependence, 1991, pp. 3748, vol. 26, No. 1.

Lee, H., et al., "Survey of methadone-drug interactions among patients of methadone maintenance treatment program in Taiwan," Substance Abuse Treatment, Prevention, and Policy, 2012, pp. 1-12, vol. 7. No. 11, BioMed Central.

Lewis, J.W., et al., "Rx 6029-M," Report of the annual scientific meeting—Committee on Problems of Drug Dependence, 1972, pp. 514-535, Research Laboratories.

Likar, Rudolph, "Transdermal buprenorphine in the management of persistent pain—safety aspects," Therapeutics and Clinical Risk Management, 2006, pp. 115-125, vol. 2, No. 1, Dove Medical Press Limited.

Lundorff, et al., "Switching from high doses of pur u-opioid agonists to transdermal buprenorphine in patients with cancer: A feasibility study," Journal of Opioid Management, Jul./Aug. 2013, pp. 255-262, vol. 9, No. 4.

Macintyre, P., et al., "Pain relief and opioid requirements in the first 24 hours after surgery in patients taking buprenorphine and methadone opioid substitution therapy," Anaesthesia Intensive Care, Mar. 2013, pp. 222-230, vol. 41, No. 2.

McCormick, Z., et al., "Acute Pain Control Challenges with Buprenorphine/Naloxone Therapy in a Patient with Compartment Syndrome Secondary to McArdle's Disease: A Case Report and Review," Pain Medicine, 2013, pp. 1187-1191, vol. 14, Wiley Periodicals, Inc.

Mendelson, J., et al., "Buprenorphine and naloxone combinations: the effects of three dose ratios in morphine-stabilized, opiate-dependent volunteers," Psychopharmacology, 1999, pp. 37-46, vol. 141, Springer-Verlag.

MOH Guidelines, "Drug Therapy for Chronic Pain Syndrome in Adult Patients to Provide Palliative Medical Care in Hospital and Outpatient Clinic Settings," 2015.

Muller, H., et al., "Intra-and Postoperative Interactions Between the two Opioids Fentanyl and Buprenorphine," Der Anaesthesist, 1986, pp. 219-225, vol. 35, No. 4.

Nantwi, K., et al., "Cellular Interactions of Buprenorphine and Morphine in Nucleus Accumbens Neurons," Drug Abuse I: Opiates, Alcohol, Depressants, Marijuana, 1994, p. A380, paragraph 2195.

Pace, M. C., et al., "Buprenorphine in long-term control of chronic pain in cancer patients," Frontiers in Bioscience, Jan. 1, 2007, pp. 1291-1299, vol. 12.

Riley, A., et al., "The Effects of Chronic Morphine on the Generalization of Buprenorphine Stimulus Control: An Assessment of Kappa Antagonist Activity," Pharmacology Biochemistry and Behavior, 1995, pp. 779-787, vol. 52, No. 4, Pergamon.

Robertson, D.H., et al., "Intravenous Buprenorphine (Temgesic): Use Following Fentanyl Analgesic Anaesthesia," Clinical Trials Journal, 1980, pp. 51-55, vol. 17, No. 2.

Roux, P., et al., "Buprenorphine/naloxone as a promising therapeutic option for opioid abusing patients with chronic pain: Reduction of pain, opioid withdrawal symptoms, and abuse liability of oral oxycodone," Pain, 2013, pp. 1442-1448, vol. 154, No. 8, Elsevier.

Rowlett, J.K. et al., "Conditioned Place Preference with Buprenorphine: Interactions with Naltrexone, Morphine and Amphetamine," Society for Neuroscience Abstracts, 1993, p. 1026, vol. 19, paragraph 418.13.

(56) References Cited

OTHER PUBLICATIONS

Sittl, Reinhard, "Transdermal buprenorphine in cancer pain and palliative care," Palliative Medicine, 2006, pp. 25-30, vol. 20, Suppl. 1, Edward Arnold (Publishers) Ltd.

Stoller, K., et al., "Effects of buprenorphine/naloxone in opioid-dependent humans," Psychopharmacology, 2001, pp. 230-242, vol. 154, No. 3, Springer-Verlag.

Strain, E., et al., "The effects of buprenorphine in buprenorphine-maintained volunteers," Psychopharmacology, 1997, pp. 329-338, vol. 129, Apringer-Verlag.

Strain, E., et al., "Effects of buprenorphine versus buprenorphine/naloxone tablets in nondependent opioid abusers," Psychopharmacology, 2000, pp. 374-383, vol. 148, No. 4, Springer-Verlag.

Strain, E., et al., "Blockade of hydromorphone effects by buprenorphine/naloxone and buprenorphine," Psychopharmacology, 2002, pp. 161-166, vol. 159, No. 2, Springer-Verlag.

Taverner, A., et al., "Transdermal delivery of a buprenorphine/naltrexone combination for the treatment of polydrug abuse," Pharmacological Reports, 2011, p. 257, vol. 63, No. 1.

Taylor, P.M., et al., "Does buprenorphine premedication affect the action of fentanyl during surgery in dogs?" Veterinary Anaesthesia and Analgesia, 2003, pp. 51-57, vol. 30, No. 1.

Teoh S.K., et al., "Acute Interactions of Buprenorphine with Intravenous Cocaine and Morphine: An Investigational New Drug Phase I Safety Evaluation," Journal of Clinical Psychopharmacology, 1993, pp. 87-99, vol. 13, No. 2, Williams & Wilkins.

Teoh, S.K., et al., "Acute Interactions of Buprenorphine with Intravenous Cocaine and Morphine," Research Monograph Series, 1993, vol. 132, p. 341.

Troester, Andreas, "Quantification of analgesic and antihyperalgesic effects of buprenorphine and fentanyl in healthy volunteers," Abstracts of the $9^{th}$ Congress of the European Association for Palliative Care, 2005, pp. 78-79.

Van Niel, J.C.G., et al., "Efficacy of Full u-Opioid Receptor Agonists is not Impaired by Concomitant Buprenorphine or Mixed Opioid Agonists/Antagonists—Preclinical and Clinical Evidence," Drug Research, 2016, pp. 562-570, vol. 66, No. 11.

Yu, G., et al., "Thienorphine Is a Potent Long-Acting Partial Opioid Agonist: A Cmparative Study with Buprenorphine," The Journal of Pharmacology and Experimental Therapeutics, 2006, pp. 282-287, vol. 318, No. 1.

* cited by examiner

The Effect of Buprenorphine on Response Latency in the Rat Hot Plate Assay

The Effect of Buprenorphine on Response Latency in the Rat Hot Plate Assay

Buprenorphine Dose-Dependently Increases Response Latency in the Rat Tail Flick Assay Buprenorphine Dose-Dependently Increases Response Latency In The Rat Tail flick Test Oxycodone Dose-Dependently Increases Response
Latency In The Rat Tail flick Test The Effect of Buprenorphine on MOR-Induced Inhibition of GI Transit in Rats The Effect of Buprenorphine and Morphine Co-Administration on Rat GI Transit The Effect of Buprenorphine on Morphine Analgesia in the Rat Hot Plate Assay The Effect of Buprenorphine on Morphine Analgesia in the Rat Hot Plate Assay
(Percent Reversal)

The Effect of Buprenorphine on Morphine Analgesia in the Rat Tail Flick Assay

The Effect of Oxycodone with Buprenorphine Pretreatment on GI Transit

The Effect of Oral Buprenorphine on Oxycodone-Induced Inhibition of Rat GI Transit The Effect of Oral Buprenorphine and Oral Oxycodone Dosing on Rat GI Transit The Effect of Buprenorphine Pre-Treatment on Oxycodone Response
Latency in the Rat Hot Plate Assay The Effect of Buprenorphine Pretreatment on Oxycodone Response
Latency in the Rat Tail Flick Assay The Effect of Buprenorphine and Oxycodone Co-Administration
Response Latency in the Rat Tail Flick Assay The Effect of Buprenorphine and Oxycodone Co-Administration
Response Latency in the Hot Plate Assay

SYSTEMS AND METHODS FOR TREATING AN OPIOID-INDUCED ADVERSE PHARMACODYNAMIC RESPONSE

FIELD OF THE INVENTION

The invention is directed to systems and methods to treat or prevent an opioid-induced adverse pharmacodynamic response.

BACKGROUND OF THE INVENTION

Endogenous opioids are found throughout the body and are involved in a variety of homeostatic functions and movement control. Receptors that are regulated by endogenous opioids include delta (δ) receptors, kappa (κ) receptors and mu (μ) receptors, all of which are located in the brain and the peripheral nervous system and play a role in analgesia. Of these receptors, the mu (μ) receptors are located in the human gastrointestinal tract on myenteric and submucosal neurons and on immune cells of the lamina propria and play a role in gastrointestinal function.

Exogenous opioids, such as morphine, oxycodone, hydrocodone, buprenorphine and fentanyl, are commonly prescribed to treat both acute and chronic pain, as their action on the opioid receptors can provide effective analgesia. However, with respect to the mu (μ) receptors, the stimulating effect exogenous opioids have on these receptors may also cause an adverse pharmacodynamic response including bowel dysfunction that can be manifested by, e.g., decreased gastric motility, delayed gastric emptying, constipation, bloating and cramping. Other adverse pharmacodynamic responses associated with opioid therapy include nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance.

Opioid-induced adverse pharmacodynamic responses in patients receiving opioid therapy for pain management can be particularly troublesome, as these patients are already trying to manage severe pain, and the added discomfort of adverse side effects can add to their distress. In some cases, the side effects may be so extreme that the patient would rather discontinue use of the opioid than continue to suffer with such side effects.

In the case of opioid-induced bowel dysfunction, current treatments include administration of laxatives, opioid antagonists and prokinetic agents. However, all of these treatments are not without risk. Laxatives, such as bisacodyl and psyllium, have a long history of safety and efficacy issues, and can themselves produce severe side effects such as dehydration and bowel obstruction Opioid antagonists, such as naloxone and naltrexone, while acting to suppress the receptors causing the bowel dysfunction, can reverse the desired analgesic effect of the opioid. Prokinetic agents, such as metoclopramide, may improve gastrointestinal motility but are associated with extrapyramidal effects, such as acute dystonic reactions, pseudoparkinsonism or akathisia.

There remains a need in the art for a composition and method to prevent or treat an opioid-induced adverse pharmacodynamic response that minimizes the issues of the current treatment protocols All references cited herein are incorporated by reference in their entireties for all purposes.

OBJECTS AND SUMMARY

It is an object of certain embodiments of the invention to provide methods of treating or preventing an opioid-induced adverse pharmacodynamic response.

It is an object of certain embodiments of the invention to provide methods of treating or preventing an opioid-induced adverse pharmacodynamic response in a patient on chronic opioid therapy.

It is an object of certain embodiments of the invention to provide methods of treating or preventing an opioid-induced adverse pharmacodynamic response in an opioid naive patient.

It is an object of certain embodiments of the invention to provide methods of treating or preventing an opioid-induced adverse pharmacodynamic response resulting from administration of an opioid having an Ema, of greater than about 25%.

It is an object of certain embodiments of the invention to provide methods of treating or preventing an opioid-induced adverse pharmacodynamic response comprising administering buprenorphine to a patient in need thereof.

It is an object of certain embodiments of the invention to provide pharmaceutical compositions for treating or preventing an opioid-induced adverse pharmacodynamic response.

It is an object of certain embodiments of the invention to provide pharmaceutical compositions for treating or preventing an opioid-induced adverse pharmacodynamic response in a patient on chronic opioid therapy.

It is an object of certain embodiments of the invention to provide pharmaceutical compositions for treating or preventing an opioid-induced adverse pharmacodynamic response in an opioid naive patient.

It is an object of certain embodiments of the invention to provide pharmaceutical compositions for treating or preventing an opioid-induced adverse pharmacodynamic response resulting from administration of an opioid having an Ema, of greater than about 25%.

It is an object of certain embodiments of the invention to provide pharmaceutical compositions comprising buprenorphine for treating or preventing an opioid-induced adverse pharmacodynamic response in a patient in need thereof.

It is an object of certain embodiments of the invention to provide methods of preparing the pharmaceutical compositions disclosed herein for treating or preventing an opioid-induced adverse pharmacodynamic response in a patient in need thereof.

It is an object of certain embodiments of the invention to provide kits for preventing for treating or preventing an opioid-induced adverse pharmacodynamic response in a patient in need thereof.

The above objects of the present invention and others can be achieved by the present invention, which in certain embodiments is directed to a method of treating or preventing an opioid-induced adverse pharmacodynamic response comprising administering to a patient in need thereof, an effective amount of buprenorphine to treat or prevent an opioid-induced adverse pharmacodynamic response.

In some embodiments, the invention is directed to a method of preventing or treating an opioid-induced adverse pharmacodynamic response comprising administering to a patient in need thereof an effective amount of buprenorphine to prevent or treat the adverse pharmacodynamic response induced by the administration of an analgesically effective amount of an opioid, e.g., selected from the group consisting of oxycodone, morphine, codeine, oxymorphone, fentanyl, hydrocodone, hydromorphone, tramadol, a pharmaceutically acceptable salt thereof and mixtures thereof, wherein the adverse pharmacodynamic response is selected from the group consisting of bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, allodynia, physical dependence and tolerance. In certain embodiments, the buprenorphine does not cause a substantial decrease, a decrease or an increase in the analgesic effectiveness of the opioid. In some embodiments, the buprenorphine is sub-analgesic In certain embodiments, the present invention is directed to a method of treating or preventing an opioid-induced adverse pharmacodynamic response comprising administering to a patient on chronic administration of an opioid having an Emax of greater than about 25%, an effective amount of buprenorphine to treat or prevent the opioid-induced adverse pharmacodynamic response.

In certain embodiments, the present invention is directed to a method of treating or preventing an opioid-induced adverse pharmacodynamic response comprising administering to an opioid naive patient an opioid having an $E_{max}$, of greater than about 25%, and an effective amount of buprenorphine to treat the opioid-induced adverse pharmacodynamic response.

In certain embodiments, the present invention is directed to a method of treating or preventing an opioid-induced adverse pharmacodynamic response comprising concurrently administering to a patient in need thereof (i) an effective amount of buprenorphine to treat or prevent an opioid-induced adverse pharmacodynamic response and (ii) another opioid.

In certain embodiments, the present invention is directed to a kit comprising (i) a unit dose of an effective amount of buprenorphine to prevent or treat an opioid-induced adverse pharmacodynamic response induced by another opioid and (ii) a unit dose of another opioid in an effective amount to treat pain, diarrhea, cough or anxiety.

In describing the present invention, the following terms are to be used as indicated below. As used herein, the singular forms "a," "an," and "the" include plural references unless the context clearly indicates otherwise. Thus, for example, reference to "an opioid" includes a single opioid as well as a mixture of two or more different opioids.

As used herein, the term "therapeutically effective" refers to the amount of drug or the rate of drug administration needed to produce a desired therapeutic result.

As used herein, the term "prophylactically effective" refers to the amount of drug or the rate of drug administration needed to produce a desired preventive result.

The term "patient" means a subject, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

As used here, the term "patient in need thereof" refers to a patient experiencing an opioid-induced adverse pharmacodynamic response such as, but not limited to, bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence or tolerance.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "buprenorphine" means buprenorphine free base, and all pharmaceutically acceptable salts, complexes, crystalline forms, co-crystals, hydrates, solvates, and mixtures thereof. In certain embodiments, the buprenorphine utilized in the present invention is buprenorphine base or a pharmaceutically acceptable salt thereof.

The term "$C_{max}$" denotes the maximum plasma concentration obtained during a dosing interval.

The term "bioavailability" is defined for purposes of the present invention as the relevant extent to which the drug (e.g., oxycodone) is absorbed from the unit dosage forms. Bioavailability is also referred to as AUC (i.e., area under the plasma concentration/time curve).

The term "opioid-induced bowel dysfunction" means a symptom associated with the digestive system, including the gastrointestinal tract caused or exacerbated by an opioid. The symptoms include but are not limited to constipation, decreased gastric emptying, abdominal cramping, spasm, bloating, delayed gastro-intestinal transit and the formation of hard dry stools.

The term "opioid analgesic" means any material that produces an analgesic effect through modulation of an opioid receptor, whether or not approved by a government agency for that purpose. The term includes all pharmaceutically active forms of the opioid analgesic, including the free base form of the agent, and all pharmaceutically acceptable salts, complexes, crystalline forms, co-crystals, hydrates, solvates, and mixtures thereof, where the form is pharmaceutically active.

The term "opioid-induced adverse pharmacodynamic response" means an unintended side effect experienced by a patient receiving opioid therapy for an intended therapeutic effect. Typically, the intended affect is analgesia. The intended effect can also be the treatment of diarrhea, cough, anxiety (e.g., due to shortness of breath) and opioid dependence. Unintended side effects associated with opioid therapy include bowel dysfunction, nausea, vomiting, somnolence, dizziness, respiratory depression, headache, dry mouth, sedation, sweats, asthenia, hypotension, dysphoria, delirium, miosis, pruritis, urticaria, urinary retention, hyperalgesia, allodynia, physical dependence and tolerance.

The term "peripherally restricted opioid-induced adverse pharmacodynamic response" means a non-central nervous system-mediated unintended side effect (e.g., bowel dysfunction) experienced by a patient receiving peripheral opioid therapy for an intended therapeutic effect (e.g., analgesia).

The term "peripherally restricted opioid analgesic" means any material that produces an analgesic effect through modulation of a peripheral opioid receptor (whether or not approved by a government agency for that purpose) and does not cross or significantly cross the blood brain barrier. The term includes all pharmaceutically active forms of the peripherally restricted opioid analgesic, including the free base form of the agent, and all pharmaceutically acceptable salts, complexes, crystalline forms, co-crystals, hydrates, solvates, and mixtures thereof, where the form is pharmaceutically active.

The term "concurrently" means that a dose of one agent is administered prior to the end of the dosing interval of another agent. For example, a dose of an opioid analgesic with a 12-hour dosing interval would be concurrently administered with a buprenorphine dose administered within 12 hours of the opioid administration.

The term "$E_{max}$" means the maximal μ GTP effect elicited by a compound relative (expressed as a %) to the effect elicited by [D-Ala$^2$, N-methyl-Phe$^4$, Gly-ol$^5$]-enkephalin (a/k/a DAMGO), which is a μ agonist standard. Generally, the $E_{max}$ value measures the efficacy of a compound to treat or prevent pain or diarrhea.

The term "opioid naive" refers to patients who are not receiving opioid analgesics on a daily basis The term "opioid tolerant" means patients who are chronically receiving opioid analgesics on a daily basis.

The term "first administration" means a single dose at the initiation of therapy to an individual subject, patient, or healthy subject or a subject population, patient population, or healthy subject population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

The term "sub-analgesic" means a dose of a drug (e.g. buprenorphine) that when administered alone does not provide analgesia upon administration to a patient. A sub-analgesic dose does not preclude that the dose can have other therapeutic, prophylactic or pharmacodynamics effects.

DETAILED DESCRIPTION

Figure 1A:
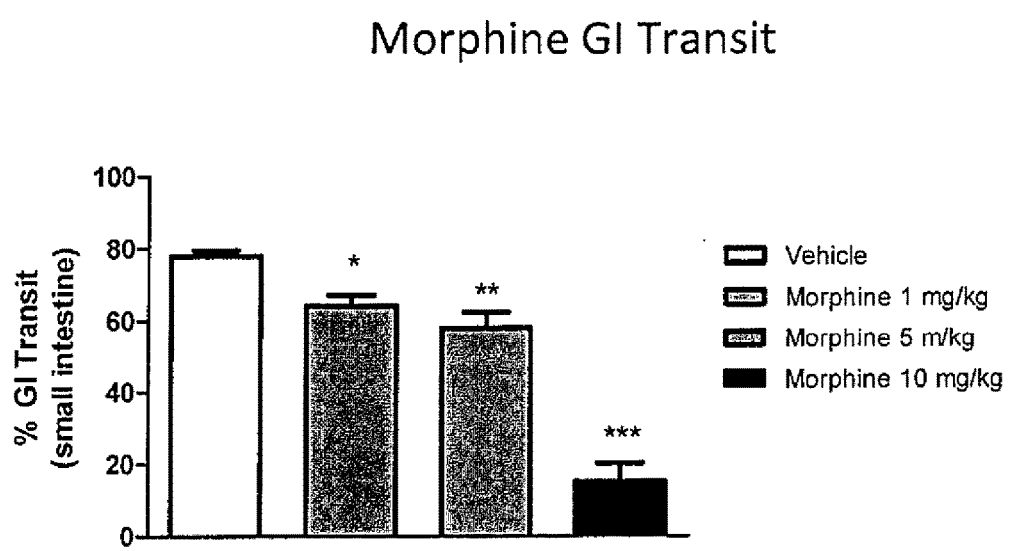
FIGS. 1A and 1B are graphical depictions of the results of Example 1.

Buprenorphine is commonly used for its analgesic properties and is formulated, e.g., in a transdermal patch (Butrans® buprenorphine transdermal system) to provide 5 mcg/hour, 10 mcg/hour or 20 mcg/hour of buprenorphine. Butrans® is indicated for the management of moderate to severe chronic pain in patients requiring a continuous, around-the-clock opioid analgesic for an extended period of time. The prescribing information states that the most common adverse events (>5%) reported by patients in clinical trials include constipation. By virtue of the present invention, buprenorphine can be administered to patients at a dose that will treat or prevent opioid-induced bowel dysfunction (e.g., opioid-induced constipation) or other opioid induced adverse pharmacodynamic responses.

In certain embodiments, the opioid-induced adverse pharmacodynamic response can be caused by the administration of an isolated or synthetic opioid that is typically endogenous to the patient (e.g., an endorphin or an enkephalin). In other embodiments, the opioid-induced adverse pharmacodynamic response can be induced by administration to the patient of an opioid that is exogenous to the patient (e.g., oxycodone, morphine, codeine, oxymorphone, fentanyl, hydrocodone, hydromorphone, tramadol or a pharmaceutically acceptable salt thereof).

In certain embodiments, the opioid-induced adverse pharmacodynamic response can be induced by a peripherally restricted opioid, e.g., by administration of a peripherally restricted opioid exogenous to the patient by any suitable route (e.g., parenterally, subcutaneously or intramuscularly).

The peripherally restricted opioid analgesic utilized in the present invention (i) does not cross the blood brain or (ii) does not significantly cross the blood brain barrier (i.e., in an amount insufficient to provide a pharmacological effect). The opioid analgesic utilized in the present invention can be peripherally restricted due to, e.g., (i) having an ionic charge (anionic or cationic), (ii) containing a quaternary amine, (iii) molecule size (e.g., proteins and peptides) or (iv) being a p-glycoprotein substrate.

In certain embodiments, the peripherally restricted opioid analgesic is loperamide or a pharmaceutically acceptable salt thereof or frakefamide or a pharmaceutically acceptable salt thereof.

When the peripherally restricted opioid analgesic is loperamide, the agent can be administered subcutaneously, e.g., in an amount from about 0.1 mg/kg to about 10 mg/kg; from about 0.5 mg/kg to about 5 mg/kg, or in an amount of about 1 mg/kg, 2 mg/kg, 3 mg/kg, or 4 mg/kg.

In certain embodiments, the buprenorphine is administered concurrently with another opioid, and the buprenorphine serves to reduce, prevent, minimize, inhibit, ameliorate or reverse the opioid-induced adverse pharmacodynamic response that might otherwise be associated with or caused by the other opioid. Typically, the other opioid is administered in an effective amount to provide an analgesic effect. In other embodiments, the other opioid is administered in an effective amount to treat diarrhea, cough, anxiety (e.g., due to shortness of breath) or opioid dependence. In certain embodiments, the buprenorphine is administered in a sub-analgesic dose, yet still in an effective amount to reduce, prevent, minimize, inhibit, ameliorate or reverse the opioid-induced adverse pharmacodynamic response that might otherwise be associated with or caused by the other opioid A patient receiving the buprenorphine therapy of the present invention may be opioid naive. Opioid naive patients may have initiated therapy with the other opioid prior to initiation of the buprenorphine therapy, or they may have initiated therapy with the other opioid concurrently with the initiation of the buprenorphine therapy. In other embodiments, the buprenorphine therapy can be initiated prior to the initiation of therapy with the other opioid so as to provide a prophylactic effect.

Alternatively, a patient receiving the buprenorphine therapy of the present invention may previously have been dosed chronically with another opioid so that he or she is now opioid tolerant.

The buprenorphine therapy of the present invention can be administered after the patient begins to exhibit symptoms of an opioid-induced adverse pharmacodynamic response. Alternatively, the buprenorphine therapy of the present invention can be administered prior to or at the same time as a patient begins treatment with the other opioid in order to reduce or avoid symptoms that might otherwise occur due to administration of the other opioid alone.

In certain embodiments, the other opioid is administered before, concurrently with, or after the buprenorphine therapy of the present invention has an Emax of greater than about 25%, greater than about 40%, greater than about 50%, greater than about 60%, greater than about 70%, greater than about 80%, or greater than about 90%. In certain embodiments, the Emax is from about 25% to about 100%, from about 25% to about 99%, from about 25% to about 95%, from about 25% to about 90%, from about 40% to about 100%, from about 40% to about 99%, from about 40% to about 95%, from about 40% to about 90%, from about 50% to about 100%, from about 50% to about 99%, from about 50% to about 95%, from about 50% to about 90%, from about 60% to about 100%, from about 60% to about 99%, from about 60% to about 95%, from about 60% to about 90%, from about 70% to about 100%, from about 70% to about 99%, from about 70% to about 95%, from about 70% to about 90%, from about 80% to about 100%, from about 80% to about 99%, from about 80% to about 95%, or from about 80% to about 90%

The buprenorphine administered in the present invention can be selected from buprenorphine base, pharmaceutically acceptable salts, solvates, polymorphs, and mixtures thereof.

The buprenorphine used according to the present invention can be administered by the same route as the other opioid. For example, the buprenorphine and the other opioid can both be administered by the same route selected from the group consisting of oral, transdermal, sublingual, buccal, intranasal, rectal, subcutaneous, intramuscular, intravenous and parenteral.

In alternative embodiments, the buprenorphine used according to the present invention can be administered by a different route than the other opioid. For example, the buprenorphine and the other opioid can be independently administered by different routes selected from the group consisting of oral, transdermal, sublingual, buccal, intranasal, rectal, subcutaneous, intramuscular, intravenous and parenteral.

Non-limiting examples of routes of administration for the present invention include transdermal buprenorphine with the other opioid administered orally; transdermal buprenorphine with the other opioid administered parenterally; transdermal buprenorphine with the other opioid administered intranasally; transdermal buprenorphine with the other opioid administered sublingually; and transdermal buprenorphine with the other opioid administered transdermally.

Other routes of administration of the present invention include sublingual buprenorphine with the other opioid administered orally; sublingual buprenorphine with the other opioid administered parenterally; sublingual buprenorphine with the other opioid administered intranasally; sublingual buprenorphine with the other opioid administered sublingually; and sublingual buprenorphine with the other opioid administered transdermally.

Other routes of administration of the present invention include oral buprenorphine with the other opioid administered orally; oral buprenorphine with the other opioid administered parenterally; oral buprenorphine with the other opioid administered intranasally; oral buprenorphine with the other opioid administered sublingually; and oral buprenorphine with the other opioid administered transdermally.

Other routes of administration of the present invention include parenteral buprenorphine with the other opioid administered orally; parenteral buprenorphine with the other opioid administered parenterally; parenteral buprenorphine with the other opioid administered intranasally; parenteral buprenorphine with the other opioid administered sublingually; and parenteral buprenorphine with the other opioid administered transdermally.

In one embodiment, the buprenorphine is administered in a transdermal system to provide, e.g., a dosing interval of about 24 hours, a dosing interval of about 3 days, or a dosing interval of about 7 days.

The transdermal buprenorphine system can be formulated to administer buprenorphine, e.g., at a rate from about 0.001 mcg/hour to about 50 mcg/hour, from about 0.01 mcg/hour to about 40 mcg/hour, from about 0.05 mcg/hour to about 30 mcg/hour, from about 0.1 mcg/hour to about 20 mcg/hour or from about 0.5 mcg/hour to about 10 mcg/hour. The rate can also be, e.g., from about 0.0001 mcg/hour to about 50 mcg/hour, from about 0.001 mcg/hour to about 40 mcg/hour, from about 0.001 mcg/hour to about 30 mcg/hour, from about 0.001 mcg/hour to about 20 mcg/hour or from about 0.001 mcg/hour to about 10 mcg/hour. The rate can also be, e.g., from about 0.001 mcg/hour to about 50 mcg/hour, from about 0.01 mcg/hour to about 40 mcg/hour, from about 0.01 mcg/hour to about 30 mcg/hour, from about 0.01 mcg/hour to about 20 mcg/hour or from about 0.01 mcg/hour to about 10 mcg/hour.

In other embodiments, the transdermal buprenorphine system can be formulated to administer buprenorphine, e.g., at a rate from about 0.001 mcg/hour to about 5 mcg/hour, from about 0.01 mcg/hour to about 4 mcg/hour, from about 0.05 mcg/hour to about 3 mcg/hour, from about 0.1 mcg/hour to about 2 mcg/hour, or from about 0.5 mcg/hour to about 1 mcg/hour. The rate can also be, e.g., from about 0.0001 mcg/hour to about 5 mcg/hour, from about 0.001 mcg/hour to about 4 mcg/hour, from about 0.001 mcg/hour to about 3 mcg/hour, from about 0.001 mcg/hour to about 2 mcg/hour, or from about 0.001 mcg/hour to about 1 mcg/hour. The rate can also be, e.g., from about 0.001 mcg/hour to about 5 mcg/hour, from about 0.01 mcg/hour to about 4 mcg/hour, from about 0.01 mcg/hour to about 3 mcg/hour, from about 0.01 mcg/hour to about 2 mcg/hour, or from about 0.01 mcg/hour to about 1 mcg/hour.

In other embodiments, the transdermal buprenorphine system can be formulated to administer buprenorphine, e.g., at a rate of about 50 mcg/hour, about 40 mcg/hour, about 30 mcg/hour, about 20 mcg/hour, about 10 mcg/hour, about 5 mcg/hour, about 4 mcg/hour, about 3 mcg/hour, about 2 mcg/hour, about 1 mcg/hour, about 0.5 mcg/hour, about 0.1 mcg/hour, about 0.05 mcg/hour, about 0.01 mcg/hour, about 0.001 mcg/hour or about 0.0001 mcg/hour.

In one embodiment, the buprenorphine is administered sublingually. The buprenorphine can be formulated in a sublingual formulation to provide, e.g., a dosing interval of about 4 hours, a dosing interval of about 6 hours, a dosing interval of about 8 hours, a dosing interval of about 12 hours, or a dosing interval of about 24 hours.

The sublingual buprenorphine formulation can be formulated to administer buprenorphine, e.g., at a dose of about 0.001 mg to about 10 mg, from about 0.01 mg to about 8 mg, from about 0.05 mg to about 6 mg, from about 0.1 mg to about 5 mg or from about 0.5 mg to about 4 mg, or from about 1 mg to about 2 mg. The sublingual formulation can also administer a dose, e.g., of about 0.0001 mg to about 10 mg, from about 0.001 mg to about 8 mg, from about 0.001 mg to about 6 mg, from about 0.001 mg to about 5 mg or from about 0.001 mg to about 4 mg, or from about 0.001 mg to about 2 mg.

In one embodiment, the buprenorphine is administered in an oral dosage form to provide, e.g., a dosing interval of about 4 hours, about 6 hours, about 8 hours, about 12 hours or about 24 hours.

The oral buprenorphine dosage form can be formulated to administer buprenorphine, e.g., at a dose of less than about 500 mg, less than about 400 mg, less than about 350 mg, less than about 300 mg, less than about 250 mg, less than about 200 mg, less than about 150 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 9 mg, less than about 8 mg, less than about 7 mg, less than about 6 mg, less than about 5 mg, less than about 4 mg, less than about 3 mg, less than about 2 mg, less than about 1 mg, less than about 0.9 mg, less than about 0.8 mg, less than about 0.7 mg, less than about 0.6 mg, less than about 0.5 mg, less than about 0.4 mg, less than about 0.3 mg, less than about 0.2 mg, less than about 0.1 mg, or less than about 0.01 mg. In certain embodiments, the dosage form can administer buprenorphine at a dose of at least about 0.0001 mg, at least about 0.001 mg, at least about 0.01 mg or at least about 0.1 mg.

In other embodiments, the oral buprenorphine dosage form can be formulated to administer buprenorphine, e.g., at a dose of from about 1 mg to about 500 mg, from about 1 mg to about 400 mg, from about 1 mg to about 350 mg, from about 1 mg to about 300 mg, from about 1 mg to about 250 mg, from about 1 mg to about 200 mg, from about 1 mg to about 150 mg, from about 1 mg to about 100 mg, from about 1 mg to about 90 mg, from about 1 mg to about 80 mg, from about 1 mg to about 70 mg, from about 1 mg to about 60 mg, from about 1 mg to about 50 mg, from about 1 mg to about 40 mg, or from about 1 mg to about 30 mg.

In other embodiments, the oral buprenorphine dosage form can be formulated to administer buprenorphine, e.g., at a dose of from about 0.0001 mg to about 30 mg, from about 0.001 mg to about 30 mg, from about 0.01 mg to about 30 mg, from about 30 mg to about 500 mg, from about 30 mg to about 400 mg, from about 30 mg to about 350 mg, from about 30 mg to about 300 mg, from about 30 mg to about 250 mg, from about 30 mg to about 200 mg, from about 30 mg to about 150 mg, from about 30 mg to about 100 mg, from about 30 mg to about 90 mg, from about 30 mg to about 80 mg, from about 30 mg to about 70 mg, from about 30 mg to about 60 mg, from about 30 mg to about 50 mg, or from about 30 mg to about 40 mg.

In other embodiments, the oral buprenorphine dosage form can be formulated to administer buprenorphine, e.g., at a dose of from about 0.1 mg to about 30 mg, from about 0.2 mg to about 30 mg, from about 0.3 mg to about 30 mg, from about 0.4 mg to about 30 mg, from about 0.5 mg to about 30 mg, from about 0.6 mg to about 30 mg, from about 0.7 mg to about 30 mg, from about 0.8 mg to about 30 mg, from about 0.9 mg to about 30 mg, from about 2 mg to about 30 mg, from about 3 mg to about 30 mg, from about 4 mg to about 30 mg, from about 5 mg to about 30 mg, from about 6 mg to about 30 mg, from about 7 mg to about 30 mg, from about 8 mg to about 30 mg, from about 9 mg to about 30 mg or from about 10 mg to about 30 mg.

In other embodiments, the oral buprenorphine dosage form can be formulated to administer buprenorphine, e.g., at a dose of from about 3 mg to about 500 mg, from about 3 mg to about 400 mg, from about 3 mg to about 350 mg, from about 3 mg to about 300 mg, from about 3 mg to about 250 mg, from about 3 mg to about 200 mg, from about 3 mg to about 150 mg, from about 3 mg to about 100 mg, from about 3 mg to about 90 mg, from about 3 mg to about 80 mg, from about 3 mg to about 70 mg, from about 3 mg to about 60 mg, from about 3 mg to about 50 mg, from about 3 mg to about 40 mg, from about 3 mg to about 30 mg, from about 3 mg to about 20 mg or from about 3 mg to about 10 mg.

In other embodiments, the oral buprenorphine dosage form can be formulated to administer buprenorphine, e.g., at a dose of from about from about 0.0001 mg to about 3 mg, from about 0.001 mg to about 3 mg, from about 0.01 mg to about 3 mg, 0.1 mg to about 3 mg, from about 0.2 mg to about 3 mg, from about 0.3 mg to about 3 mg, from about 0.4 mg to about 3 mg, from about 0.5 mg to about 3 mg, from about 0.6 mg to about 3 mg, from about 0.7 mg to about 3 mg, from about 0.8 mg to about 3 mg, from about 0.9 mg to about 3 mg, from about 1 mg to about 3 mg, or from about 2 mg to about 3 mg.

In certain embodiments, the buprenorphine is administered orally in an amount of from about 0.0001 mg to about 500 mg, from about 0.001 mg to about 500 mg, from about 0.01 mg to about 500 mg, from about 0.1 mg to about 500 mg, from about 0.1 mg to about 400 mg, from about 0.1 mg to about 300 mg, from about 0.1 mg to about 200 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, or from about 0.1 mg to about 5 mg.

The buprenorphine of the present invention can be administered by any route (e.g., oral or transdermal or subcutaneous) to provide at steady state, e.g., from about 0.0001 mg/kg to about 1 mg/kg, from about 0.001 mg/kg to about 1 mg/kg, from about 0.005 mg/kg to about 0.5 mg/kg or from about 0.05 mg/kg to about 0.1 mg/kg. In other embodiments, the buprenorphine of the present invention can be administered by any route (e.g., oral) to provide at steady state, e.g., about 1 mg/kg, about 0.5 mg/kg, about 0.1 mg/kg, about 0.05 mg/kg, about 0.005 mg/kg, about 0.001 mg/kg, or about 0.0001 mg/kg. The buprenorphine can be administered for any suitable time, e.g., for the full duration of therapy with the other opioid or for a fraction of the full duration of therapy with the other opioid.

The buprenorphine of the present invention can be administered by any route (e.g., oral or transdermal or subcutaneous) to provide after first administration or at steady state, a Cmax, e.g., from about 0.0001 ng/ml to about 15 ng/ml, from about 0.001 ng/ml to about 15 ng/ml, from about 0.005 ng/ml to about 12 ng/ml, from about 0.05 ng/ml to about 10 ng/ml, from about 0.05 ng/ml to about 1 ng/ml, from about 0.05 ng/ml to about 0.5 ng/ml from about 0.5 ng/ml to about 8 ng/ml, from about 1.0 ng/ml to about 5 ng/ml, or from about 2 ng/ml to about 4 ng/ml.

In other embodiments, the buprenorphine of the present invention can be administered by any route (e.g., oral or transdermal or subcutaneous) to provide after first administration or at steady state, a Cmax, e.g., of about 0.0001 ng/ml, about 0.001 ng/ml, about 0.01 ng/ml, about 0.1 ng/ml, about 1 ng/ml, about 2 ng/ml, about 3 ng/ml, about 4 ng/ml, or about 5 ng/ml.

In other embodiments, the buprenorphine of the present invention can be administered by any route (e.g., oral or transdermal or subcutaneous) to provide after first administration or at steady state, a Cmax, e.g., of less than about 5 ng/ml, less than about 4 ng/ml, less than about 3 ng/ml, less than about 2 ng/ml, less than about 1 ng/ml, less than about 0.1 ng/ml, less than about 0.01 ng/ml, less than about 0.001 ng/ml or less than about 0.0001 ng/ml. In certain embodiments, the Cmax is, e.g., at least about 0.0001 ng/ml, at least about 0.001 ng/ml, at least about 0.01 ng/ml, or at least about 0.1 ng/ml.

In other embodiments, the buprenorphine of the present invention can be administered by any route (e.g., oral or transdermal or subcutaneous) to provide after first administration or at steady state, an AUC, e.g., from about 0.001 ng/ml*hr to about 100 ng/ml*hr, from about 0.01 ng/ml*hr to about 100 ng/ml*hr, from about 0.1 ng/ml*hr to about 75 ng/ml*hr, from about 1.0 ng/ml*hr to about 50 ng/ml*hr, from about 5.0 ng/ml*hr to about 40 ng/ml*hr, or from about 10 ng/ml*hr to about 30 ng/ml*hr.

In certain embodiments, the buprenorphine is administered orally and provides treatment or prevention of an opioid-induced adverse pharmacodynamic response (e.g., constipation) without a circulating plasma level, or a plasma level below detectable limits.

The steady state or first administration AUC and Cmax values disclosed herein may be obtained by any suitable route of administration such as transdermally, sublingually, buccally, orally, subcutaneously, intramuscularly or by a parenteral depot injection. A depot injection of buprenorphine may be administered by implantation (for example, subcutaneously or intramuscularly) or by intramuscular injection. In such formulations, the release of the buprenorphine is controlled by formulation with a suitable polymeric or hydrophobic material (e.g., polylactic glycolic acid), an ion exchange resin, or as a sparingly soluble derivative (e.g., a sparingly soluble salt). Preferably, the depot injection provides a dosing interval from about 1 day to about 3 months, or about 3 days, about 7 days, about 10 days, about 14 days, about 21 days, about one month, about 6 weeks, or about 2 months.

The other opioid can be selected from the group consisting of alfentanil, allylprodine, alphaprodine, anileridine, benzylmorphine, bezitramide, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the other opioid agonist is selected from the group consisting of codeine, fentanyl, hydromorphone, hydrocodone, oxycodone, dihydrocodeine, dihydromorphine, morphine, tramadol, oxymorphone, pharmaceutically acceptable salts thereof, and mixtures thereof.

In certain embodiments, the other opioid is oxycodone or a pharmaceutically acceptable salt thereof.

In certain embodiments, the other opioid is hydrocodone or a pharmaceutically acceptable salt thereof.

In certain embodiments, the other opioid is hydromorphone or a pharmaceutically acceptable salt thereof.

In certain embodiments, the other opioid is oxymorphone or a pharmaceutically acceptable salt thereof.

In certain embodiments, the other opioid is morphine or a pharmaceutically acceptable salt thereof.

The other opioid may be formulated in the free base form, or as a pharmaceutically acceptable salt thereof.

The other opioid can be administered as a transdermal patch, a liquid oral dosage form, or as a solid oral dosage form in either immediate or controlled release form.

The other opioid can be administered in controlled release form with a dosing interval, e.g., of about 8 hours, about 12 hours or about 24 hours. The other opioid can alternatively be administered in immediate release form with a dosing interval, e.g., of about 2 hours, about 4 hours, about 6 hours or about 8 hours. The other opioid, either in controlled release form or immediate release form, can be utilized in the present invention either alone or in combination with a non-opioid analgesic such as an NSAID (e.g., acetaminophen, aspirin, ibuprofen, naproxen, diclofenac, or a COX-2 inhibitor). Certain combination products can contain in addition to the other opioid, from about 200 mg to about 800 mg acetaminophen (e.g., about 325 mg, about 500 mg or about 650 mg); from about 200 mg to about 800 mg aspirin (e.g., about 325 mg or about 500 mg); or about 200 mg to about 1000 mg ibuprofen (e.g., about 200 mg, about 400 mg, about 600 mg or about 800 mg).

The other opioid in controlled release form can be oxycodone hydrochloride in an amount, e.g., from about 10 mg to about 160 mg per unit dose. In specific embodiments, each unit dose can provide an amount of oxycodone hydrochloride of about 10 mg, about 20 mg, about 30 mg, about 40 mg, about 50 mg, about 60 mg, about 70 mg, about 80 mg, about 100 mg, about 120 mg or about 160 mg. Controlled release oxycodone hydrochloride utilized in the present invention may be Oxycontin® (Oxycodone hydrochloride extended release tablets) commercially available from Purdue Pharma. The oxycodone hydrochloride in immediate release form can be in an amount from about 2.5 mg to about 50 mg, about 2.5 mg, about 4.5 mg; about 4.8355 mg; about 5 mg, about 7.5 mg, about 10 mg, about 15 mg, about 20 mg, or about 30 mg. Immediate release oxycodone hydrochloride utilized in the present invention may be Tylox® (acetaminophen, oxycodone hydrochloride); Roxilox® (acetaminophen, oxycodone hydrochloride); Percocet® (acetaminophen, oxycodone hydrochloride); Oxycet® (acetaminophen, oxycodone hydrochloride); Roxicet (acetaminophen, oxycodone hydrochloride); Percodan® (aspirin, oxycodone hydrochloride); Oxecta® (acetaminophen, oxycodone hydrochloride); or Roxicodone® (oxycodone hydrochloride).

The other opioid in controlled release form can be tramadol hydrochloride in an amount, e.g., from about 100 mg to about 300 mg per unit dose. In specific embodiments, each unit dose can provide an amount of tramadol hydrochloride of about 100 mg, about 150 mg, about 200 mg, about 250 mg, or about 300 mg. Tramadol hydrochloride utilized in the present invention may be Conzip® (Tramadol hydrochloride extended release capsules); Ryzolt® (Tramadol hydrochloride extended release tablets); or Ultram ER® (Tramadol hydrochloride extended release capsules). Immediate release tramadol hydrochloride utilized in the present invention may be Ultracet® (acetaminophen, tramadol hydrochloride); or Rybix ODT® (tramadol hydrochloride orally disintegrating tablet).

The other opioid in controlled release form can be oxymorphone hydrochloride in an amount, e.g., from about 5 mg to about 40 mg per unit dose. In specific embodiments, each unit dose can provide an amount of oxymorphone hydrochloride of about 5 mg, about 10 mg, about 15 mg, about 20 mg, about 25 mg, about 30 mg, about 35 mg or about 40 mg. Oxymorphone hydrochloride utilized in the present invention may be Opana ER® (Oxymorphone hydrochloride extended release tablets). Immediate release oxymorphone hydrochloride utilized in the present invention may be Opana® (oxymorphone hydrochloride).

The other opioid in controlled release form can be hydrocodone bitartrate in an amount, e.g., from about 2 mg to about 200 mg per unit dose. In specific embodiments, each unit dose can provide an amount of hydrocodone bitartrate of about 20 mg, about 30 mg, about 40 mg, about 60 mg, about 80 mg, about 100 mg or about 120 mg. Immediate release hydrocodone bitartrate utilized in the present invention may be Vicodin® (acetaminophen, hydrocodone bitartrate); Zydone® (acetaminophen, hydrocodone bitartrate); Anexsia® (acetaminophen, hydrocodone bitartrate); Lortab® (acetaminophen, hydrocodone bitartrate) or Vicoprofen® (ibuprofen, hydrocodone bitartrate).

The other opioid in controlled release form can be morphine sulfate in an amount, e.g., from about 2 mg to about 200 mg per unit dose. In specific embodiments, each unit dose can provide an amount of morphine sulfate of about 15 mg, about 20 mg, about 30 mg, about 40 mg, about 60 mg, about 80 mg, about 100 mg, about 120 mg or about 200 mg. Morphine sulfate utilized in the present invention may be Avinza® (Morphine sulfate extended release capsules); Kadian® (Morphine sulfate extended release capsules); or MS Contin® (Morphine sulfate extended release tablets).

The other opioid in controlled release form can be hydromorphone hydrochloride in an amount, e.g., from about 2 mg to about 200 mg per unit dose. In specific embodiments, each unit dose can provide an amount of hydromorphone hydrochloride of about 8 mg, about 12 mg, about 16 mg, about 32 mg, about 64 mg, or about 128 mg; or about 20 mg, about 30 mg, about 40 mg, about 60 mg, about 80 mg, about 100 mg or about 120 mg. Hydromorphone hydrochloride utilized in the present invention may be Exalgo® (Hydromorphone hydrochloride extended-release tablets); Palladone® (Hydromorphone hydrochloride extended-release capsules); or Dilaudid® (Hydromorphone hydrochloride oral tablets).

The other opioid in controlled release form can be tapentadol hydrochloride in an amount, e.g., from about 2 mg to about 400 mg per unit dose. In specific embodiments, each unit dose can provide an amount of tapentadol hydrochloride of about 50 mg, about 100 mg, about 150 mg, or about 250 mg. Tapentadol utilized in the present invention may be Nucynta ER® (Tapentadol extended release oral tablets) or Nucynta® (Tapentadol oral tablets).

The other opioid can be fentanyl disposed in a transdermal system that delivers the fentanyl in an amount, e.g., of about 12.5 mcg/hr; about 25 mcg/hr; about 50 mcg/hr; about 75 mcg/hr or about 100 mcg/hr. Fentanyl utilized in the present invention can be Duragesic® (fentanyl film, extended release).

In certain embodiments, the ratio of the daily dose of buprenorphine to the other opioid is, e.g., less than about 1:5 (w/w), less than about 1:10 (w/w), less than about 1:50 (w/w), less than about 1:5 (w/w), less than about 1:10 (w/w), less than about 1:25 (w/w), less than about 1:50 (w/w), less than about 1:75 (w/w), less than about 1:100 (w/w), less than about 1:150 (w/w), less than about 1:200 (w/w), less than about 1:250 (w/w), less than about 1:500 (w/w), less than about 1:600 (w/w), less than about 1:700 (w/w), less than about 1:850 (w/w), or less than about 1:1000 (w/w), or less than about 1:10,000 (w/w). In other embodiments, the ratio of the daily dose of buprenorphine to the other opioid is, e.g., at least 1:10,000 (w/w), at least about 1:1000 (w/w), at least about 1:850 (w/w), at least 1:700 (w/w), at least about 1:600 (w/w), or least about 1:500 (w/w). in alternative embodiments, the ratio of the daily dose of buprenorphine to the other opioid is, e.g., from about 1:5 (w/w) to about 1:10,000 (w/w), from about 1:5 (w/w) to about 1:1000 (w/w), from about 1:5 (w/w) to about 1:850 (w/w), from about 1:5 (w/w) to about 1:700 (w/w), from about 1:5 (w/w) to about 1:600 (w/w), or from about 1:5 (w/w) to about 1:500 (w/w).

In certain embodiments, the buprenorphine is administered transdermally in an amount of about 5 mcg/hr or less (e.g., from about 0.0001 mcg/hr to about 5 mcg/hr) concurrently with oral controlled release oxycodone hydrochloride in a unit dose of about 10 mg, about 20 mg, about 30 mg, about 40 mg, about 50 mg, about 60 mg, about 70 mg, about 80 mg, about 100 mg, about 120 mg or about 160 mg. Preferably, the buprenorphine dosing interval is about 3 days or about 7 days and the oxycodone dosing interval is about 12 hours.

In certain embodiments, the buprenorphine is administered transdermally in an amount of about 5 mcg/hr or less concurrently with oral controlled release oxymorphone hydrochloride in a unit dose of about 5 mg, about 10 mg, about 15 mg, about 20 mg, about 25 mg, about 30 mg, about 35 mg or about 40 mg. Preferably, the buprenorphine dosing interval is about 3 days or about 7 days, and the oxymorphone dosing interval is about 12 hours.

In certain embodiments, the buprenorphine is administered transdermally in an amount of about 5 mcg/hr or less (e.g., from about 0.0001 mcg/hr to about 5 mcg/hr) concurrently with oral controlled release oxymorphone hydrochloride in a unit dose of about 5 mg, about 10 mg, about 15 mg, about 20 mg, about 25 mg, about 30 mg, about 35 mg or about 40 mg. Preferably, the buprenorphine dosing interval is about 3 days or about 7 days, and the oxymorphone dosing interval is about 12 hours.

In certain embodiments, the buprenorphine is administered transdermally in an amount of about 5 mcg/hr or less (e.g., from about 0.0001 mcg/hr to about 5 mcg/hr) concurrently with oral controlled release hydrocodone bitartrate in a unit dose of about 20 mg, about 30 mg, about 40 mg, about 60 mg, about 80 mg, about 100 mg or about 120 mg. Preferably, the buprenorphine dosing interval is about 3 days or about 7 days, and the hydrocodone dosing interval is about 12 hours or about 24 hours.

In certain embodiments, the buprenorphine is administered transdermally in an amount of about 5 mcg/hr or less (e.g., from about 0.0001 mcg/hr to about 5 mcg/hr) concurrently with oral controlled release morphine sulfate in a unit dose of about 15 mg, about 30 mg, about 40 mg, about 60 mg, about 80 mg, about 100 mg, about 120 mg or about 200 mg. Preferably, the buprenorphine dosing interval is about 3 days or about 7 days, and the morphine dosing interval is about 12 hours or about 24 hours.

In certain embodiments, the buprenorphine is administered transdermally in an amount of about 5 mcg/hr or less (e.g., from about 0.0001 mcg/hr to about 5 mcg/hr) concurrently with transdermally administered fentanyl in an amount of about 12.5 mcg/hr; about 25 mcg/hr; about 50 mcg/hr; about 75 mcg/hr or about 100 mcg/hr. Preferably, the buprenorphine dosing interval is about 3 or 7 days and the fentanyl dosing interval is about 3 or 7 days.

In certain embodiments, the buprenorphine is administered orally concurrently with oral administration of the other opioid. The buprenorphine can be in the same oral dosage form as the other opioid or can be in a separate oral dosage form as the other opioid.

In certain embodiments, the buprenorphine is administered orally in an amount of about 5 mg or less (e.g., from about 0.0001 mg to about 5 mg), about 4 mg or less (e.g., from about 0.0001 mg to about 4 mg), about 2 mg or less (e.g., from about 0.0001 mg to about 2 mg), about 1 mg or less (e.g., from about 0.0001 mg to about 1 mg), about 0.5 mg or less (e.g., from about 0.0001 mg to about 0.5 mg), about 0.25 mg or less (e.g., from about 0.0001 mg to about 0.25 mg) or about 0.1 mg or less (e.g., from about 0.0001 mg to about 0.01 mg) concurrently with oral controlled release oxycodone hydrochloride in a unit dose of about 10 mg, about 20 mg, about 30 mg, about 40 mg, about 50 mg, about 60 mg, about 70 mg, about 80 mg, about 100 mg, about 120 mg or about 160 mg. Preferably, the buprenorphine dosing interval is about 12 hours or about 24 hours and the oxycodone dosing interval is about 12 hours.

In certain embodiments, the buprenorphine is administered orally in an amount of about 5 mg or less (e.g., from about 0.0001 mg to about 5 mg), about 4 mg or less (e.g., from about 0.0001 mg to about 4 mg), about 2 mg or less (e.g., from about 0.0001 mg to about 2 mg), about 1 mg or less (e.g., from about 0.0001 mg to about 1 mg), about 0.5 mg or less (e.g., from about 0.0001 mg to about 0.5 mg), about 0.25 mg or less (e.g., from about 0.0001 mg to about 0.25 mg) or about 0.1 mg or less (e.g., from about 0.0001 mg to about 0.01 mg) concurrently with oral controlled release oxymorphone hydrochloride in a unit dose of about 5 mg, about 10 mg, about 15 mg, about 20 mg, about 25 mg, about 30 mg, about 35 mg or about 40 mg. Preferably, the buprenorphine dosing interval is about 12 hours or about 24 hours, and the oxymorphone dosing interval is about 12 hours.

In certain embodiments, the buprenorphine is administered orally in an amount of about 5 mg or less (e.g., from about 0.0001 mg to about 5 mg), about 4 mg or less (e.g., from about 0.0001 mg to about 4 mg), about 2 mg or less (e.g., from about 0.0001 mg to about 2 mg), about 1 mg or less (e.g., from about 0.0001 mg to about 1 mg), about 0.5 mg or less (e.g., from about 0.0001 mg to about 0.5 mg), about 0.25 mg or less (e.g., from about 0.0001 mg to about 0.25 mg) or about 0.1 mg or less (e.g., from about 0.0001 mg to about 0.01 mg) concurrently with oral controlled release hydrocodone bitartrate in a unit dose of about 20 mg, about 30 mg, about 40 mg, about 60 mg, about 80 mg, about 100 mg or about 120 mg. Preferably, the buprenorphine dosing interval is about 12 hours or about 24 hours, and the hydrocodone dosing interval is about 12 hours or about 24 hours.

In certain embodiments, the buprenorphine is administered orally in an amount of about 5 mg or less (e.g., from about 0.0001 mg to about 5 mg), about 4 mg or less (e.g., from about 0.0001 mg to about 4 mg), about 2 mg or less (e.g., from about 0.0001 mg to about 2 mg), about 1 mg or less (e.g., from about 0.0001 mg to about 1 mg), about 0.5 mg or less (e.g., from about 0.0001 mg to about 0.5 mg), about 0.25 mg or less (e.g., from about 0.0001 mg to about 0.25 mg) or about 0.1 mg or less (e.g., from about 0.0001 mg to about 0.01 mg) concurrently with oral controlled release morphine sulfate in a unit dose of about 15 mg, about 30 mg, about 40 mg, about 60 mg, about 80 mg, about 100 mg, about 120 mg or about 200 mg. Preferably, the buprenorphine dosing interval is about 12 hours or about 24 hours, and the morphine dosing interval is about 12 hours or about 24 hours.

In certain embodiments, the buprenorphine is administered orally in an amount of about 5 mg or less (e.g., from about 0.0001 mg to about 5 mg), about 4 mg or less (e.g., from about 0.0001 mg to about 4 mg), about 2 mg or less (e.g., from about 0.0001 mg to about 2 mg), about 1 mg or less (e.g., from about 0.0001 mg to about 1 mg), about 0.5 mg or less (e.g., from about 0.0001 mg to about 0.5 mg), about 0.25 mg or less (e.g., from about 0.0001 mg to about 0.25 mg) or about 0.1 mg or less (e.g., from about 0.0001 mg to about 0.01 mg) concurrently with oral controlled release hydromorphone hydrochloride in a unit dose of about 8 mg, about 12 mg, about 16 mg, about 32 mg, about 64 mg, or about 128 mg. Preferably, the buprenorphine dosing interval is about 12 hours or about 24 hours, and the hydromorphone dosing interval is about 12 hours.

In certain embodiments, the buprenorphine is administered orally in an amount of about 5 mg or less (e.g., from about 0.0001 mg to about 5 mg), about 4 mg or less (e.g., from about 0.0001 mg to about 4 mg), about 2 mg or less (e.g., from about 0.0001 mg to about 2 mg), about 1 mg or less (e.g., from about 0.0001 mg to about 1 mg), about 0.5 mg or less (e.g., from about 0.0001 mg to about 0.5 mg), about 0.25 mg or less (e.g., from about 0.0001 mg to about 0.25 mg) or about 0.1 mg or less (e.g., from about 0.0001 mg to about 0.01 mg) concurrently with transdermally administered fentanyl in an amount of about 12.5 mcg/hr; about 25 mcg/hr; about 50 mcg/hr; about 75 mcg/hr or about 100 mcg/hr. Preferably, the buprenorphine dosing interval is about 12 hours or about 24 hours and the fentanyl dosing interval is about 3 or 7 days.

The buprenorphine and the other opioid can both be formulated to provide (i) an immediate release from the same or different oral dosage forms or (ii) controlled release from the same or different dosage forms.

In alternate embodiments, the buprenorphine can be formulated for immediate release and the other opioid can be formulated for controlled release, from the same or different oral dosage forms.

In further embodiments, the buprenorphine can be formulated for controlled release and the other opioid can be formulated for immediate release, from the same or different oral dosage forms.

Preferably, the oral dosage form containing either the buprenorphine, the other opioid, or both agents, is in the form of a tablet or capsule.

In formulations containing both agents, the buprenorphine and the other opioid can be commingled in a tablet or capsule.

In a tablet formulation, the core can contain the buprenorphine which is layered with a coating of the other opioid. Alternatively, the core can contain the other opioid which is layered with a coating of the buprenorphine. In other embodiments, the formulation can be in a laminar arrangement such that the buprenorphine and the other opioid are layered in at least a bilayer tablet.

In capsule formulations, the agents can be in the same multiparticulate formulation or in separate multiparticulate formulations that are contained in a pharmaceutically acceptable capsule (e.g., a gelatin capsule). The components of the multiparticulate formulation can be in the form of a core containing the buprenorphine which is layered with a coating of the other opioid. Alternatively, the components of the multiparticulate formulation can be in the form of a core containing the other opioid which is layered with a coating of the buprenorphine. In other embodiments, the capsule can contain a granulation or powder blend containing both the buprenorphine and the other opioid, or separate granulations or powders each containing the buprenorphine or the other opioid.

In oral formulations, the buprenorphine and/or the other opioid can be formulated to provide a delayed release in order to target release at a specific site in the gastro-intestinal tract (e.g., the intestine or the colon). The delayed release can be obtained with an enteric coating on the tablet, multiparticulates, capsule or any other dosage form or component of a dosage form, as appropriate. Enteric materials that can be utilized to provide a delayed release of buprenorphine and/or the other opioid include, e.g., shellac, cellulose acetate phthalate (CAP), polyvinyl acetate phthalate (PVAP), hydroxypropylmethylcellulose phthalate, methacrylic acid ester copolymers and zein.

The invention further encompasses kits that can simplify the administration of buprenorphine concurrently with another opioid in order to prevent or treat an opioid-induced adverse pharmacodynamic response. A typical kit of the invention comprises a unit dosage form of buprenorphine and a unit dosage form of another opioid.

In one embodiment, the kit comprises one container holding at least one unit dose of buprenorphine and another container holding at least one unit dose of another opioid. The kit can further comprise a label or printed instructions instructing the use of the buprenorphine to prevent or treat an opioid-induced adverse pharmacodynamic response.

Kits of the invention can further comprise a device that is useful for administering the unit dosage forms. Examples of such a device include, but are not limited to, a syringe, a drip bag, a patch, an inhaler, and an enema bag.

In one embodiment, buprenorphine is included in the kit as a transdermal patch, e.g., suitable for administration every 3 or 7 days, along with an amount of unit doses of a controlled or immediate release opioid (e.g., oxycodone hydrochloride or oxymorphone hydrochloride) for an equivalent time period. For example, a kit of the invention can include a 7 day transdermal buprenorphine patch and 14 controlled release oxycodone hydrochloride tablets (to be administered every 12 hours). A kit of the invention can include any combination of a buprenorphine formulation with a formulation the other opioid as disclosed herein. When oral solid dosage forms are included in a kit, the formulations can be contained in a blister package.

The buprenorphine can be in an amount that (i) does not cause a decrease in the analgesic effectiveness of the other opioid, or (ii) does not cause a substantial decrease in the analgesic effectiveness of the other opioid, or (iii) provides an increase in analgesia as compared to the administration of the other opioid alone. Thus, the buprenorphine can also be in an amount that (i) causes a decrease in the analgesic effectiveness of the other opioid, or (ii) causes a substantial decrease in the analgesic effectiveness of the other opioid, or (iii) does not provide an increase in analgesia as compared to the administration of the other opioid alone. Although when the other opioid is utilized for an analgesic effect, embodiments that negatively affect the analgesically effectiveness of the other opioid are not preferred.

The concentration of buprenorphine that affects the analgesic efficacy of the concurrently administered other opioid as compared to the concentration of buprenorphine that prevents or treats opioid induced adverse pharmacodynamic response (e.g., bowel dysfunction) depends on the identity of the other opioid that is concurrently being administered. Preferably, the window of separation is sufficient such that the buprenorphine effectively prevents or treats the opioid induced adverse pharmacodynamic response without affecting the analgesic potency of the opioid. Oxycodone is a specific opioid with a sufficient window that enables the prevention or treatment of the opioid-induced adverse pharmacodynamic response with buprenorphine with a reduced likelihood of the oxycodone having its analgesic effect compromised.

In preferred embodiments, the minimal concentration of buprenorphine that affects the analgesic efficacy of the concurrently administered other opioid is about 1000 times, about 750 times, about 500 times, about 250 times, or about 100 times the concentration of buprenorphine that prevents or treats opioid induced adverse pharmacodynamic response. In other embodiments, the minimal concentration of buprenorphine that affects the analgesic effectiveness of the concurrently administered other opioid is about 90 times, about 80 times, about 70 times, about 60 times, about 50 times, about 40 times, about 30 times, about 20 times 10 times, about 5 times, or about 2 times the minimal concentration of buprenorphine that prevents or treats the opioid induced adverse pharmacodynamic response. In some embodiments, the minimal concentration of buprenorphine that affects the analgesic efficacy of the concurrently administered other opioid is from about 2 to about 250 times, from about 10 to about 175 times, from about 25 to about 150 times, from about 50 to about 125 times or from about 75 to about 100 times the minimal concentration of buprenorphine that prevents or treats the opioid induced adverse pharmacodynamic response.

Formulations of Buprenorphine and the Other Opioid

The buprenorphine and/or the other opioid can be administered as a component of a pharmaceutical composition that comprises a pharmaceutically acceptable carrier or excipient. The buprenorphine and/or the other opioid can be formulated as (i) separate formulations intended for different routes of administration, (ii) separate formulations intended for the same route of administration, or (iii) in the same formulation to be administered together by the same route of administration. The pharmaceutical compositions can be administered by any appropriate route, as determined by the medical practitioner. Methods of administration may include intradermal, intramuscular, intraperitoneal, parenteral, intravenous, subcutaneous, intranasal, epidural, oral, sublingual, buccal, intracerebral, intravaginal, transdermal, transmucosal, rectal, by inhalation, or topical (particularly the skin).

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, suppositories, aerosols, sprays, or any other form suitable for use. In one embodiment, the composition is in the form of a capsule (see, e.g., U.S. Pat. No. 5,698,155). Other examples of suitable pharmaceutical excipients are described in Remington's Pharmaceutical Sciences 1447-1676 (Alfonso R. Gennaro ed., 19th ed. 1995), incorporated herein by reference.

Pharmaceutical compositions of the invention preferably comprise a suitable amount of a pharmaceutically acceptable excipient so as to provide the form for proper administration to the patient. Such a pharmaceutical excipient can be a diluent, suspending agent, solubilizer, binder, disintegrant, buffer, glidant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to a patient. Water is a particularly useful excipient when the pharmaceutical composition is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, American Pharmaceutical Association (1986).

In certain embodiments, the pharmaceutical compositions are formulated for oral administration. A pharmaceutical composition of the invention to be orally delivered can be in the form of tablets, capsules, gelcaps, caplets, lozenges, aqueous or oily solutions, suspensions, granules, powders, emulsions, syrups, or elixirs, for example. When the buprenorphine and/or the other opioid is incorporated into oral tablets, such tablets can be compressed, tablet triturates, enteric-coated, sugar-coated, film-coated, multiply compressed or multiply layered.

An orally administered pharmaceutical composition can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in Pharmaceutical Dosage Forms: Tablets (Lieberman, Lachman and Schwartz, eds., 2nd ed.) published by Marcel Dekker, Inc. Techniques and compositions for making tablets (compressed and molded), capsules (hard and soft gelatin) and pills are also described in Remington's Pharmaceutical Sciences 1553-1593 (Arthur Osol, ed., 16.sup.th ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in Pharmaceutical Dosage Forms: Disperse Systems, (Lieberman, Rieger and Banker, eds.) published by Marcel Dekker, Inc.

When the buprenorphine and/or the other opioid is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When the buprenorphine and/or the other opioid is to be injected parenterally, it can be, e.g., in the form of an isotonic sterile solution. The buprenorphine and/or the other opioid can also be in the form of a powder for reconstitution as an injectable formulation.

In certain embodiments, the buprenorphine and/or the other opioid is formulated into a pharmaceutical composition for intravenous administration. Typically, such compositions comprise sterile isotonic aqueous buffer. Where necessary, the compositions can also include a solubilizing agent. A pharmaceutical composition for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the buprenorphine and/or the other opioid is to be administered by infusion, it can be dispensed, for example, with an infusion bottle containing sterile pharmaceutical grade water or saline. When the buprenorphine and/or the other opioid is administered by injection, an ampule of sterile water for injection or saline can be provided so that the ingredients can be mixed prior to administration.

When the buprenorphine and/or the other opioid is to be administered by inhalation, it can be formulated into a dry aerosol, or an aqueous or partially aqueous solution.

In another embodiment, the buprenorphine and/or the other opioid can be delivered in a vesicle, in particular a liposome (see Langer, Science 249:1527-1533 (1990); and Treat et al., Liposomes in the Therapy of Infectious Disease and Cancer 317-327 and 353-365 (1989)).

In certain embodiments, the buprenorphine and/or the other opioid can be delivered in an immediate release form. In other embodiments, the buprenorphine and/or the other opioid can be delivered in a controlled-release system or sustained-release system. Controlled- or sustained-release pharmaceutical compositions can have a common goal of improving drug therapy over the results achieved by their non-controlled or non-sustained-release counterparts. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the buprenorphine and/or the other opioid, and can thus reduce the occurrence of adverse side effects.

Controlled- or sustained-release compositions can initially release an amount of the buprenorphine and/or the other opioid that promptly produces the desired therapeutic or prophylactic effect, and gradually and continually release other amounts of the buprenorphine and/or the other opioid to maintain a level of therapeutic or prophylactic effect over an extended period of time. To maintain a constant level of the buprenorphine and/or the other opioid in the body, the pharmaceutical composition can release the active(s) from the dosage form at a rate that will replace the amount of active(s) being metabolized and excreted from the body. Controlled or sustained release of an active ingredient can be triggered by any of various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or both of the active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in Medical Applications of Controlled Release, Vol. 2, Applications and Evaluation, R. S. Langer and D. L. Wise eds., CRC Press (1984). Other controlled- or sustained-release systems that are discussed in the review by Langer, Science 249:1527-1533 (1990) can be selected for use according to the present invention. In one embodiment, a pump can be used (Langer, Science 249:1527-1533 (1990); Sefton, CRC Crit. Ref Biomed. Eng. 14:201 (1987); Buchwald et al., Surgery 88:507 (1980); and Saudek et al., N. Engl. J. Med. 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, J. Macromol. Sci. Rev. Macromol. Chem. 23:61 (1983); Levy et al., Science 228: 190 (1985); During et al., Ann. Neurol. 25:351 (1989); and Howard et al., J. Neurosurg. 71:105 (1989)).

When in tablet or pill form, a pharmaceutical composition of the invention can be coated to delay disintegration and absorption in the gastrointestinal tract thereby providing targeted release to a particular portion of the GI tract, or providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions preferably include standard excipients of pharmaceutical grade selected, for example, from mannitol, lactose, starch, magnesium stearate, sodium saccharin, cellulose, and magnesium carbonate, among others.

Controlled release oral dosage forms according to the present invention may also be prepared as osmotic dosage forms. The osmotic dosage forms preferably include a bilayer core comprising a drug layer (containing the buprenorphine and/or the other opioid) and a delivery or push layer, wherein the bilayer core is surrounded by a semipermeable wall and optionally having at least one passageway disposed therein.

The expression "passageway" as used for the purpose of this invention, includes an aperture, orifice, bore, pore, porous element, fiber, capillary tube, porous overlay, porous insert, microporous member, or porous composition through any of which the buprenorphine and/or the other opioid can diffuse, migrate or be pumped through. The passageway can also include a compound that erodes or is leached from the wall in the fluid environment of use to produce at least one passageway. Representative compounds for forming a passageway include erodible poly(glycolic) acid or poly(lactic) acid in the wall; a gelatinous filament; a water-removable poly(vinyl alcohol); and leachable compounds such as fluid-removable pore-forming polysaccharides, acids, salts or oxides. Examples of leachable compounds include sorbitol, sucrose, lactose, maltose, or fructose. The passageway can have any shape, such as round, triangular, square and elliptical, for assisting in the controlled release of the buprenorphine and/or the other opioid from the dosage form. The dosage form can be manufactured with one or more passageways in spaced-apart relation on one or more surfaces of the dosage form. A passageway and equipment for forming a passageway are described in U.S. Pat. Nos. 3,845,770; 3,916,899; 4,063,064 and 4,088,864. Passageways prepared by leaching are described in U.S. Pat. Nos. 4,200,098 and 4,285,987.

In certain embodiments the drug layer may comprise at least one polymer hydrogel. Examples of polymer hydrogels include but are not limited to a maltodextrin polymer; a poly(alkylene oxide) such as a poly(ethylene oxide) and a poly(propylene oxide); an alkali carboxyalkylcellulose, wherein the alkali is sodium or potassium and the alkyl is methyl, ethyl, propyl, or butyl; and a copolymer of ethylene-acrylic acid, including methacrylic and ethacrylic acid.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide may be a member selected from the group consisting of polymethylene oxide, polyethylene oxide and polypropylene oxide. The carboxyalkylcellulose may be a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethylcellulose, carboxyalkylhydroxyalkylcellulose, carboxymethylhydroxyethylcellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into the dosage form, thereby swelling and expanding as an osmotic hydrogel, whereby they push the contents of the drug layer from the osmotic dosage form.

The push layer may also include one or more osmotically effective compounds that imbibe an environmental fluid, for example, from the gastrointestinal tract, into the dosage form to contribute to the delivery kinetics of the displacement layer. Examples of osmotically effective compounds comprise a member selected from the group consisting of osmotic salts and osmotic carbohydrates. Examples of specific osmagents include but are not limited to sodium chloride, potassium chloride, magnesium sulfate, lithium phosphate, lithium chloride, sodium phosphate, potassium sulfate, sodium sulfate, potassium phosphate, glucose, fructose and maltose.

The push layer may optionally include a hydroxypropylalkylcellulose such as hydroxypropylmethylcellulose, hydroxypropylethylcellulose, hydroxypropyl isopropyl cellulose, hydroxypropylbutylcellulose, and hydroxypropylpentylcellulose.

In certain alternative embodiments, the dosage form comprises a substantially homogenous core comprising the buprenorphine and/or the other opioid, a pharmaceutically acceptable polymer (e.g., polyethylene oxide) and optional excipients such as disintegrants and absorption enhancers. The substantially homogenous core is surrounded by a semipermeable wall having a passageway (as defined above) for the release of the buprenorphine and/or the other opioid. Such an embodiments would not require a push layer.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates.

With osmotic systems, the buprenorphine or the other opioid can be formulated for controlled release and the other agent can be formulated for immediate release, e.g., by coating onto the semipermeable wall.

Pharmaceutical compositions of the invention include single unit dosage forms suitable for oral administration such as, but not limited to, tablets, capsules, gelcaps, and caplets, which may be adapted for controlled or immediate release.

In certain embodiments, both the buprenorphine and the other opioid can be included in the same dosage form. For example, the buprenorphine and the other opioid can both be included in a transdermal dosage form such that each agent is administered according to the desired rate. In certain embodiments, the two agents can be segregated from each other in a dual reservoir system.

Transdermal Dosage Forms

In certain embodiments, wherein the buprenorphine is administered in a transdermal device, the formulation can, e.g., be a transdermal patch, a transdermal plaster, a transdermal disc or an iontophoretic transdermal device.

Transdermal dosage forms used in accordance with the invention can include a backing layer made of a pharmaceutically acceptable material which is impermeable to the buprenorphine. The backing layer can serve as a protective cover for the buprenorphine and may also provide a support function. Examples of materials suitable for making the backing layer are films of high and low density polyethylene, polypropylene, polyvinylchloride, polyurethane, polyesters such as poly(ethylene phthalate), metal foils, metal foil laminates of suitable polymer films, textile fabrics, and the like. The backing layer can be any appropriate thickness which will provide the desired protective and support functions. A suitable thickness can be, e.g., from about 10 microns to about 200 microns.

In certain embodiments, the transdermal dosage forms used in accordance with the invention contain a biologically acceptable polymer matrix layer. Generally, the polymers used to form the polymer matrix layer are capable of allowing the buprenorphine to pass through at a controlled rate. A non-limiting list of exemplary materials for inclusion in the polymer matrix includes polyethylene, polypropylene, ethylene/propylene copolymers, ethylene/ethylacrylate copolymers, ethylenevinyl acetate copolymers, silicones, natural or synthetic rubber, polyacrylic esters and copolymers thereof, polyurethanes, polyisobutylene, chlorinated polyethylene, polyvinylchloride, vinyl chloride-vinyl acetate copolymer, polymethacrylates, polyvinylidene chloride, poly(ethylene terephthalate), ethylene-vinyl alcohol copolymer, ethylene-vinyloxyethanol copolymer, silicones, silicone copolymers such as polysiloxane-polymethacrylate copolymers, cellulose polymers (e.g., ethyl cellulose, and cellulose esters), polycarbonates, polytetrafluoroethylene and mixtures thereof.

The polymer matrix layer may optionally include a pharmaceutically acceptable cross-linking agent such as, e.g., tetrapropoxy silane.

In certain embodiments, the transdermal delivery systems used in accordance with the methods of the present invention include an adhesive layer to affix the dosage form to the skin of the patient for a desired period of administration, e.g., about 1 day, about 2 days, about 3 days, about 4 days, about 5 days, about 6 days, or about 7 days. If the adhesive layer of the dosage form fails to provide adhesion for the desired period of time, it is possible to maintain contact between the dosage form with the skin, e.g., by affixing the dosage form to the skin of the patient with an adhesive tape.

The adhesive layer may include an adhesive such as polyacrylic adhesive polymers, acrylate copolymers (e.g., polyacrylate) and polyisobutylene adhesive polymers.

The transdermal dosage forms which can be used in accordance with the present invention may optionally include a permeation enhancing agent. Permeation enhancing agents are compounds which promote penetration and/or absorption of the buprenorphine into the blood stream of the patient. A non-limiting list of permeation enhancing agents includes polyethylene glycols, surfactants, and the like.

In one embodiment, the transdermal dosage form which may be used in accordance with the present invention includes a non-permeable backing layer comprising, e.g., a polyester; an adhesive layer comprising, e.g., a polyacrylate; and a matrix containing the buprenorphine and other excipients such as softeners, permeability enhancers, viscosity agents and the like.

The buprenorphine may be included in the device in a drug reservoir, drug matrix or drug/adhesive layer. Preferably, the active agent is buprenorphine or a pharmaceutically acceptable salt thereof.

Certain preferred transdermal delivery systems also include a softening agent. Suitable softening agents include higher alcohols such as dodecanol, undecanol, octanol, esters of carboxylic acids, diesters of dicarboxylic acids and triglycerides. Further examples of suitable softeners are multivalent alcohols such as levulinic acid, caprylic acids, glycerol and 1,2-propanediol, which can also be etherified by a polyethylene glycol.

A buprenorphine solvent may also be included in the transdermal delivery systems of the present invention. A non-limiting list of suitable solvents includes those with at least one acidic group such as monoesters of dicarboxylic acids (e.g., monomethylglutarate and monomethyladipate).

In certain embodiments, the transdermal dosage form includes a removable protective layer. The removable protective layer is removed prior to application, and may comprise the materials used for the production of the backing layer disclosed above provided that they are rendered removable, e.g., by silicone treatment. Other removable protective layers include polytetra-fluoroethylene, treated paper, allophane, polyvinyl chloride, and the like. Generally, the removable protective layer is in contact with the adhesive layer and provides a convenient means of maintaining the integrity of the adhesive layer until the desired time of application.

The transdermal system utilized in the present invention is used by adhering the transdermal system to a dermal surface of a patient. The dermal surface should be clean and unbroken. In certain embodiments, the transdermal system will be sufficiently adhesive to remain adhered to the patient's skin during normal everyday activities and for an adequate period of time. In other embodiments, it may be necessary to further secure the transdermal system to the patient, e.g., by wrapping tape or a medical bandage around the area to which the transdermal system has been applied.

In some embodiments, the transdermal system can be cut or otherwise separated into two or more separate pieces to adjust the amount of buprenorphine that will be delivered to the patient. For example, the transdermal system may include perforations or lines along which to cut for dividing the transdermal system into multiple doses.

Mucosal Tablets and Films

In certain embodiments, the buprenorphine can be formulated for application to the mucosal tissue. Such a formulation can be a tablet, film or spray adapted for lingual (i.e., to be placed onto the tongue), sublingual (i.e., to be placed under the tongue), buccal (i.e., to be applied to the cheek), or gingival (i.e., to be applied to the gums) administration. One benefit of such administration is the avoidance or reduction of first pass metabolism associated with oral administration.

Sublingual, lingual, buccal and gingival tablets, and films are formulated to disintegrate rapidly in the mouth to provide absorption of the buprenorphine in the oral cavity in a relatively short period of time. Such forms may contain soluble excipients such as lactose, mannitol, dextrose, sucrose or mixtures thereof. Such forms may also contain granulating and disintegrating agents such as starch, silicon dioxide, or sodium starch glycolate, binding agents such as povidone or hydroxypropyl-methyl cellulose and lubricating agents such as magnesium stearate. Such forms may also comprise a bioerodible polymeric carrier that optionally may also serve to adhere the dosage form to the sublingual, lingual, buccal, or gingival mucosa.

In some embodiments, the buprenorphine can be formulated as a gel in the form of a film or strip. The film should be capable of disintegrating quickly, e.g., in about 0.5 second to 120 seconds from contact with a surface in the oral cavity. In certain embodiments, the film is capable of disintegrating within about 0.5 second to about 60 seconds, or in less than about 5 seconds, or in less than about 10 seconds, or in less than about 15 seconds, or in less than about 20 seconds, or in less than about 30 seconds, or in less than about 45 seconds.

The film may comprise hydrophilic (water-soluble and water-swellable) polymers that adhere to a wet surface in the oral cavity. Polymeric carriers may be selected from acrylic acid polymers, hydrolyzed polyvinylalcohols, polyethylene oxides, polyacrylates, vinyl polymers, polyvinylpyrrolidones, dextrans, guar gums, pectins; starches, and cellulosic polymers, among others.

Mucosal tablets or films can also include a permeation enhancer to increase the rate at which the buprenorphine permeates through the mucosal tissue to which it is applied, e.g., the buccal, lingual, gingival, or sublingual mucosa. Permeation enhancers may be selected from dimethylsulfoxide ("DMSO"), dimethyl formamide ("DMF"), N,N-dimethylacetamide ("DMA"), decylmethylsulfoxide ("C10MSO"), polyethylene glycol monolaurate ("PEGML"), glycerol monolaurate, lecithin, 1-substituted azacycloheptan-2-ones, alcohols, and surfactants, among others.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

In the below examples and the related graphical depictions: morphine sulphate is referred to as morphine, morphine sulphate and MS; buprenorphine free base is referred to as buprenorphine, burprenorphine free base and bup; oxycodone hydrochloride is referred to as oxycodone, oxycodone hydrochloride and oxy.

Example 1

The Effect of Morphine Alone on GI Transit

Example 1A

Test subjects: male Sprague-Dawley rats, 200-230 g; n=10/group.

Morphine sulfate (1-10 mg/kg) or 0.9% normal saline (vehicle) was administered subcutaneously (SC) to the test subjects. 0.5 hour later, a charcoal meal (1 ml/100 grams) was orally administered (PO) to the test subjects.

One hour after the charcoal meal, the test subjects were euthanized by CO2 and the gastrointestinal tract was removed from the stomach to the cecum. The length of the small intestine and the distance (cm) to the leading edge of the charcoal were recorded. Data were analyzed using a one-way ANOVA followed by the Dunnett's Multiple Comparisons test where *P<0.05, P<0.01 and*P<0.001. Data are represented as the means+S.E.M. The results shown in FIG. 1A demonstrate that morphine decreases gastrointestinal transit as evidenced by the decreased % of the small intestine traveled by a charcoal meal following morphine treatment as compared to vehicle treated animals. This effect was dose dependent with a greater magnitude of effect observed with increasing dose.

Example 1B

Test subjects: male Sprague-Dawley rats, 200-230 g; n=10/group.

Figure 1B:
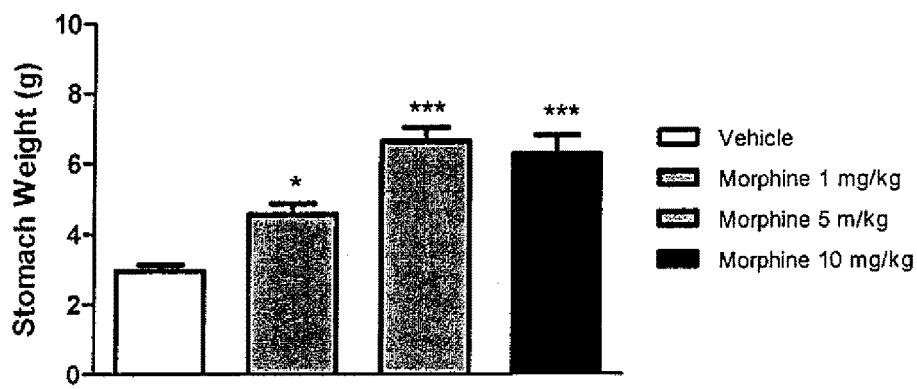

Morphine sulfate (1-10 mg/kg) or 0.9% normal saline (vehicle) was administered SC to the test subjects. 0.5 hour later, a charcoal meal (1 ml/100 grams) was administered PO to the test subjects. One hour after the charcoal meal, the test subjects were euthanized by CO2 and the stomachs were removed and weighed. Data were analyzed using a one-way ANOVA followed by the Dunnett's Multiple Comparisons test where *P<0.05, P<0.01 and *P<0.001. Data are represented as the means+S.E.M. Results are shown in FIG. 1B. The results shown in FIG. 1B demonstrate that morphine decreases gastrointestinal transit as evidenced by increased stomach weight due to delayed gastric emptying. This effect was dose dependent with a greater magnitude of effect observed with increasing dose.

Example 2

The Effect of Morphine in Response Latency in a Rat Hot Plate Assay

Example 2A

Subjects: male Sprague-Dawley rats, 200-230 g; n=10/group.

Morphine sulphate (1-10 mg/kg) was dissolved in 0.9% normal saline solution (NSS) (vehicle) and administered SC 1 hour prior to testing against vehicle. Data were analyzed by a two-way ANOVA using a Bonferroni Multiple Comparison Test,***P<0.001.

Figure 2A:
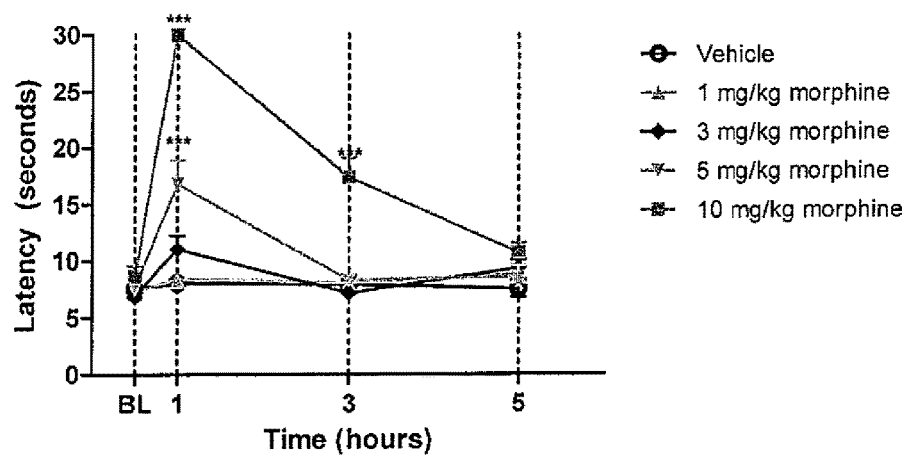
FIGS. 2A and 2B are graphical depictions of the results of Example 2.

The results shown in FIG. 2A demonstrate that morphine provides analgesia as evidenced by increased latency to nocifensive response. This effect was dose dependent with a greater magnitude of effect observed with increasing dose.

Example 2B

Subjects: male Sprague-Dawley rats, 200-230 g; n=10/group.

Morphine sulphate (1-10 mg/kg) was dissolved in 0.9% normal saline solution (NSS) (vehicle) and administered SC 1 hour prior to testing against vehicle. % MPE=Percent of Maximum Possible Effect. % MPE=(test latency-baseline)/(cutoff-baseline). Data was analyzed using a Bonferroni Multiple Comparison Test,***P<0.001.

Figure 2B:
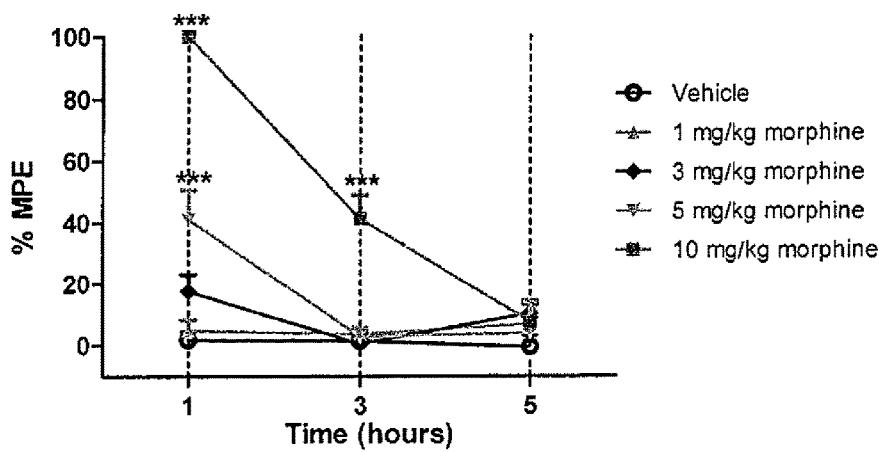

The results shown in FIG. 2 B demonstrate that morphine provides analgesia as evidenced by increased % of the maximal possible effect (a normalized transformation of the latency to nocifensive response). This effect was dose dependent with a greater magnitude of effect observed with increasing dose.

Example 3

The Effect of Morphine in Response Latency in a Rat Tail Flick Assay

Example 3A

Subjects: male Sprague-Dawley rats, 200-230 g; n=10/group.

Morphine sulphate (1-10 mg/kg) was dissolved in 0.9% normal saline solution (NSS) (vehicle) and administered SC 1 hour prior to testing against vehicle. Data were analyzed by a two-way ANOVA using a Bonferroni post-hoc test, *P<0.05, ***P<0.001.

Figure 3A:
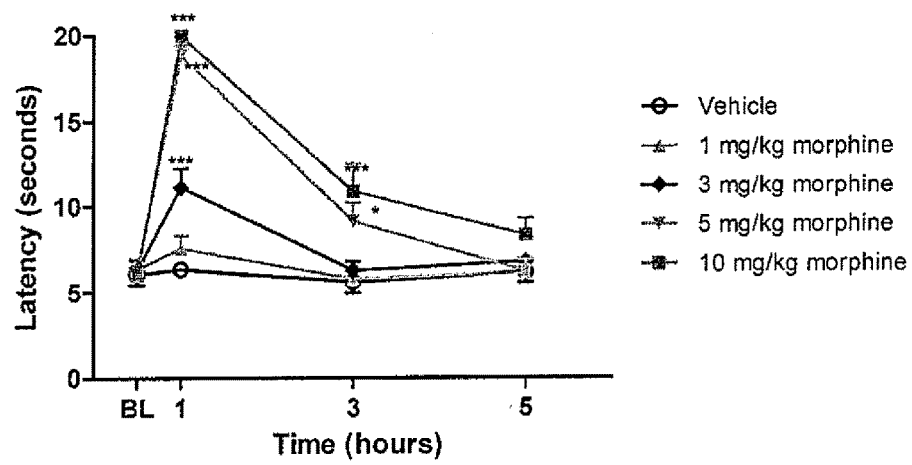
FIGS. 3A and 3B are graphical depictions of the results of Example 3.

The results, shown in FIG. 3A demonstrate that morphine provides analgesia as evidenced by increased latency to nocifensive response. This effect was dose dependent with a greater magnitude of effect observed with increasing dose.

Example 3B

Subjects: male Sprague-Dawley rats, 200-230 g; n=10/group.

Morphine sulphate (1-10 mg/kg) was dissolved in 0.9% normal saline solution (NSS) (vehicle) and administered SC 1 hour prior to testing against vehicle. % MPE=Percent of Maximum Possible Effect. % MPE=(test latency-baseline)/(cutoff(20 s)-baseline)*100. Data were analyzed by a two-way ANOVA using a Bonferroni post-hoc test, *P<0.05, P<0.01, *P<0.001.

Figure 3B:
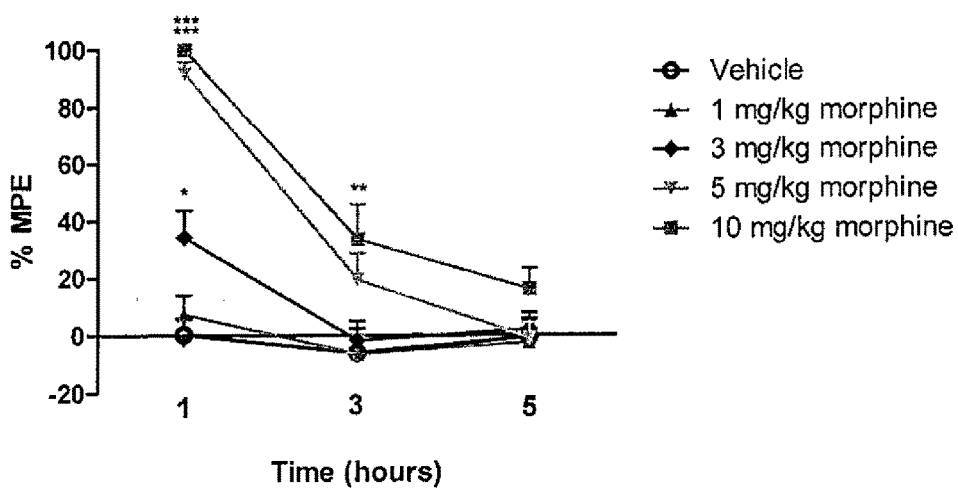

The results shown in FIG. 3B demonstrate that morphine provides analgesia as evidenced by increased % of the maximal possible effect (a normalized transformation of the latency to nocifensive response). This effect was dose dependent with a greater magnitude of effect observed with increasing dose.

Example 4

The Effect of Buprenorphine Alone on GI Transit

Example 4A

Test subjects: male Sprague-Dawley rats, 220-240 g; n=10/group.

Morphine sulfate (10 mg/kg), buprenorphine free base (0.005-1 mg/kg) (Bup) or 25% hydroxylpropyl-beta-cyclodextrin (HPBCD; vehicle) was administered SC to test subjects. 0.5 hour later, test subjects were given a PO administration of a charcoal meal (1 ml/100 grams).

One hour after the charcoal meal, the test subjects were euthanized by CO2 and the GI tract was removed from the stomach to the cecum. The length of the small intestine and the distance (cm) to the leading edge of the charcoal were recorded. Data were analyzed using a one-way ANOVA followed by Bonferroni's Multiple Comparisons Test where *P<0.05, P<0.01 and **P<0.001 vs. vehicle. Data are represented as the means+S.E.M.

Figure 4A:
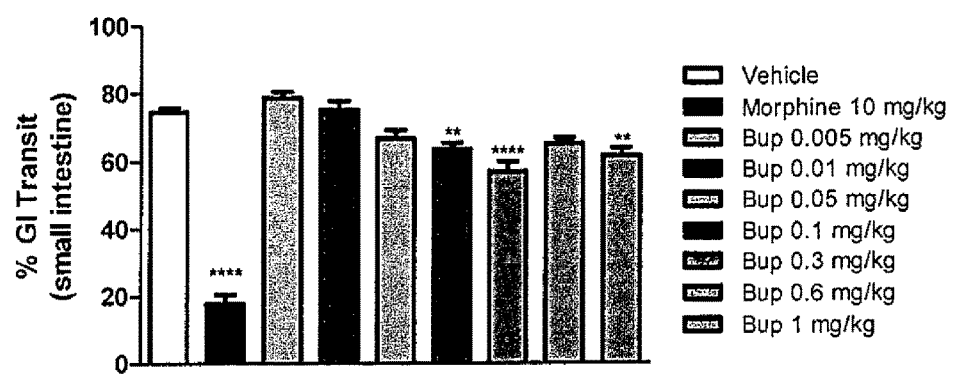
FIGS. 4A and 4B are graphical depictions of the results of Example 4.

The results shown in FIG. 4A demonstrates that buprenorphine decreases gastrointestinal transit as evidenced by the decreased % of the small intestine traveled by a charcoal meal following buprenorphine treatment as compared to vehicle treated animals. The effect was less in magnitude as compared to either morphine or oxycodone and a "floor effect" was observed such that with increasing dose further retardation of GI transit was not observed.

Example 4B

Test subjects: male Sprague-Dawley rats, 203-235 g; n=10-11/group.

Rats were dosed with buprenorphine/Bup or vehicle (25% HPBCD) PO 1 hour prior to PO administration of a charcoal meal (1 ml/100 grams), while some others were given 10 mg/kg of morphine sulfate 0.5 hour before the charcoal meal. One hour after charcoal, all rats were euthanized by $CO_2$ and the GI tract was removed from the stomach to the cecum. The length of the small intestine and the distance (cm) to the leading edge of charcoal was recorded. Data were analyzed using a one-way ANOVA with Bonferonni's Post-Test where ****P<0.0001 vs. vehicle. Data are represented as the means+S.E.M.

Figure 4B:
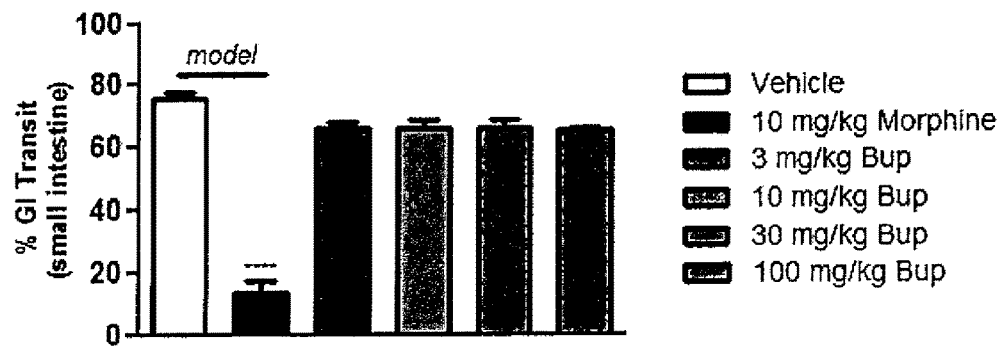

Results shown in FIG. 4B demonstrate that 3-100 mg/kg PO Bup alone does not alter GI Transit in the rat.

Example 5

The Effect of Buprenorphine in Response Latency in a Rat Hot Plate Assay

Example 5A

Subjects: male Sprague-Dawley rats, 225-253 g; n=10/group.

Buprenorphine free base (0.01-1 mg/kg) was formulated in 25% HPBCD (vehicle). Morphine sulphate (10 mg/kg), the positive control, was dissolved in 0.9% NSS (vehicle). The formulations were administered SC 1 hour prior to testing against vehicle. Data were analyzed by a two-way ANOVA using a Bonferroni multiple comparisons test, where *P<0.05 and ***P<0.001. Data are represented as the means+S.E.M.

Figure 5A:
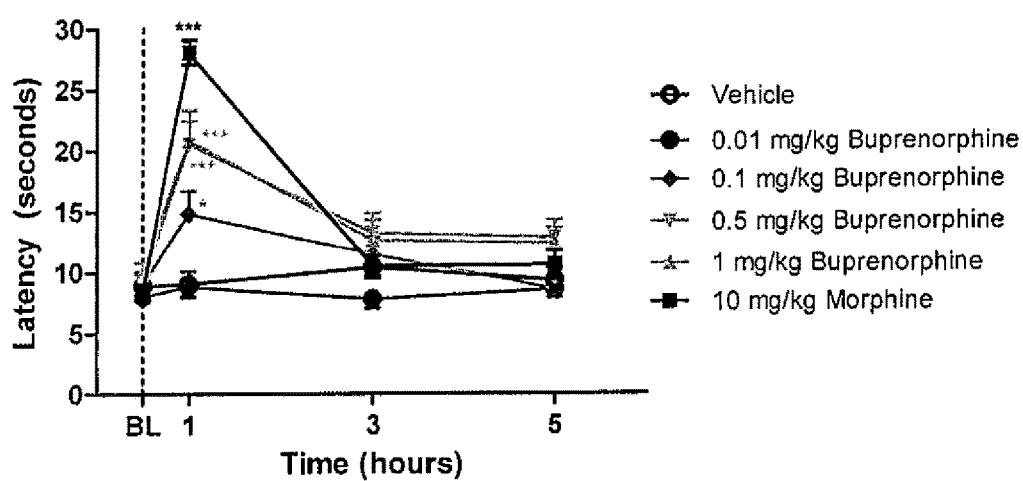
FIGS. 5A, 5B and 5C are graphical depictions of the results of Example 5.

The results shown in FIG. 5A demonstrate that buprenorphine provides analgesia as evidenced by increased latency to nocifensive response. This effect was dose dependent with a greater magnitude of effect observed with increasing dose.

Example 5B

Subjects: male Sprague-Dawley rats, 225-253 g; n=10/group.

Buprenorphine free base (0.01-1 mg/kg) was formulated in 25% HPBCD (vehicle). Morphine sulphate (10 mg/kg) was dissolved in 0.9% NSS (vehicle). The formulations were administered SC 1 hour prior to testing against vehicle. % MPE=Percent Maximum Possible Effect. % MPE=(test latency-baseline)/(cutoff (30 s)-baseline). Data were analyzed by a two-way ANOVA using Bonferroni Multiple Comparisons test for post-hoc analysis, where *P<0.05 and ***P<0.001. Data are represented as the means+SEM.

Figure 5B:
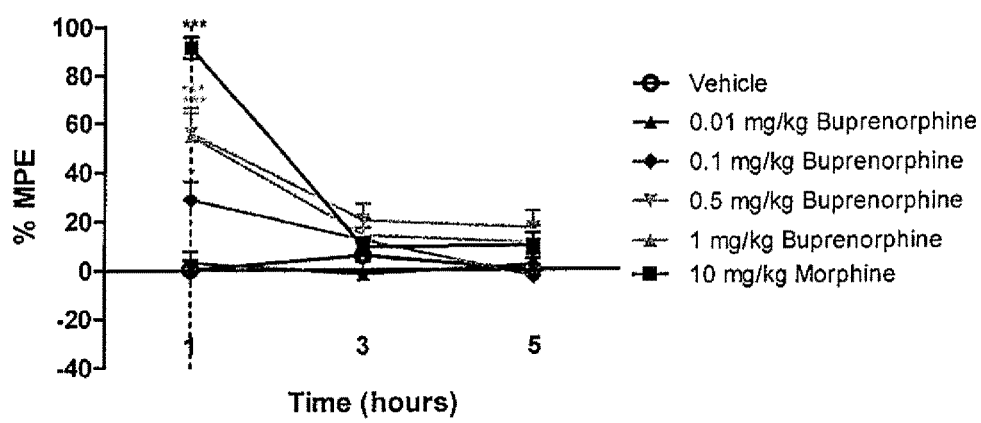

The results shown in FIG. 5B demonstrate that buprenorphine provides analgesia as evidenced by increased % of the maximal possible effect (a normalized transformation of the latency to nocifensive response). This effect was dose dependent with a greater magnitude of effect observed with increasing dose.

Example 5C

Test Subjects: male Sprague-Dawley rats, 217-249 g; n=10-21/group.

Buprenorphine/Bup or vehicle (25% HPBCD) were administered PO 1 hour prior to testing. The positive control, morphine sulfate in 0.9% NS, was administered SC 1 hour prior to testing. Rats were assessed one day prior (BL) and then 1, 3 and 5 hours post-dosing. Hot Plate was set to 52° C. and cutoff was 30 seconds. Data were analyzed by a two-way ANOVA using a Bonferroni Multiple Comparisons Test, where *P<0.05, *P<0.001 and **P<0.0001 versus vehicle. Data are represented as the means+S.E.M from two combined studies.

Figure 5C:
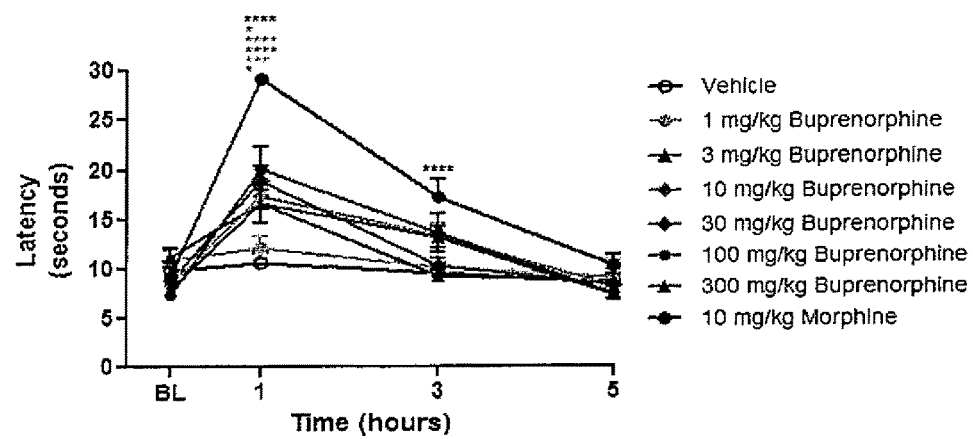

Results shown in FIG. 5C demonstrate that buprenorphine mitigates acute pain at MED 3 mg/kg.

Example 6

The Effect of Buprenorphine in Response Latency in a Rat Tail Flick Assay

Example 6A

Subjects: male Sprague-Dawley rats, 200-230 g; n=10/group

Buprenorphine free base (0.01-1 mg/kg) was formulated in 0.9% NSS (vehicle). Morphine sulphate (10 mg/kg) was dissolved in 0.9% NSS (vehicle). The formulations were administered SC 1 hour prior to testing against vehicle. Data were analyzed by a two-way ANOVA using a Bonferroni multiple comparisons test, *P<0.05, ***P<0.001.

Figure 6A:
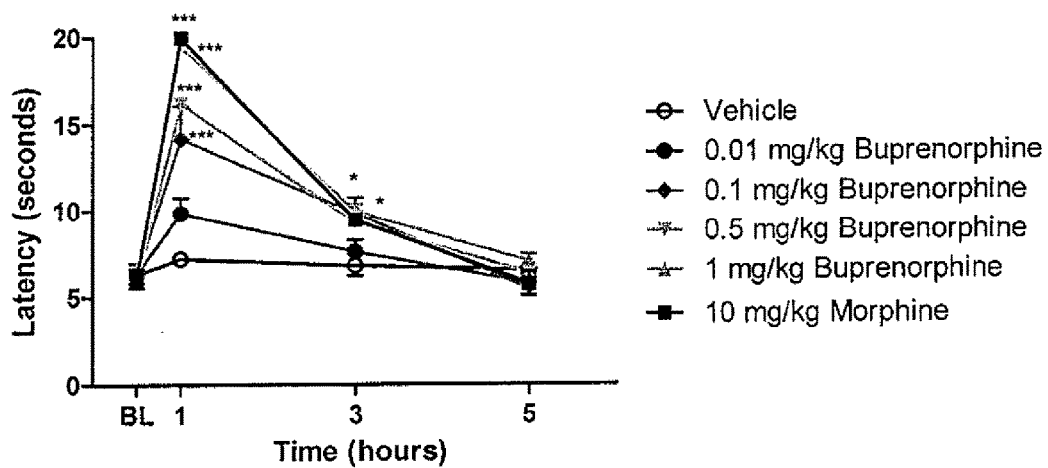
FIGS. 6A, 6B and 6C are graphical depictions of the results of Example 6.

The results shown in FIG. 6A demonstrate that buprenorphine provides analgesia as evidenced by increased latency to nocifensive response. This effect was dose dependent with a greater magnitude of effect observed with increasing dose.

Example 6B

Subjects: male Sprague-Dawley rats, 200-230 g; n=10/group.

Buprenorphine free base (0.01-1 mg/kg) was formulated in 25% HPBCD (vehicle). Morphine sulphate (10 mg/kg) was dissolved in 0.9% NSS (vehicle). The formulations were administered SC 1 hour prior to testing against vehicle. % MPE=Percent Maximum Possible Effect. % MPE=(test latency-baseline)/(cutoff(20 s)-baseline)*100. Data were analyzed by a two-way ANOVA using a Bonferroni multiple comparisons test, ***P<0.001.

Figure 6B:
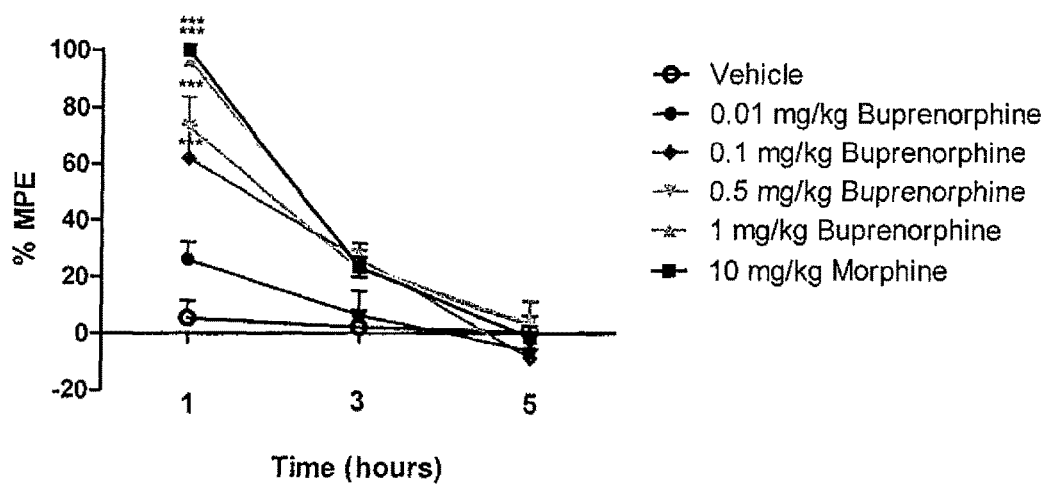

The results shown in FIG. 6B demonstrate that buprenorphine % of the maximal possible effect (a normalized transformation of the latency to nocifensive response). This effect was dose dependent with a greater magnitude of effect observed with increasing dose.

Example 6C

Test subjects: male Sprague-Dawley rats, 217-261 g; n=10-21/group.

Buprenorphine base/Bup or vehicle (25% HPBCD) were administered PO 1 hour prior to testing. The positive control, morphine sulfate in 0.9% NS was administered SC 1 hour prior to testing. Rats were assessed the day prior (BL) and then 1, 3 and 5 hours post-dosing. Tail Flick was set to 40 intensity and cutoff 20 seconds. Data were analyzed by a two-way ANOVA using a Bonferroni Multiple Comparisons Test, where *P<0.05,*P<0.001 and **P<0.0001. Data are represented as the means+S.E.M of two combined studies.

Figure 6C:
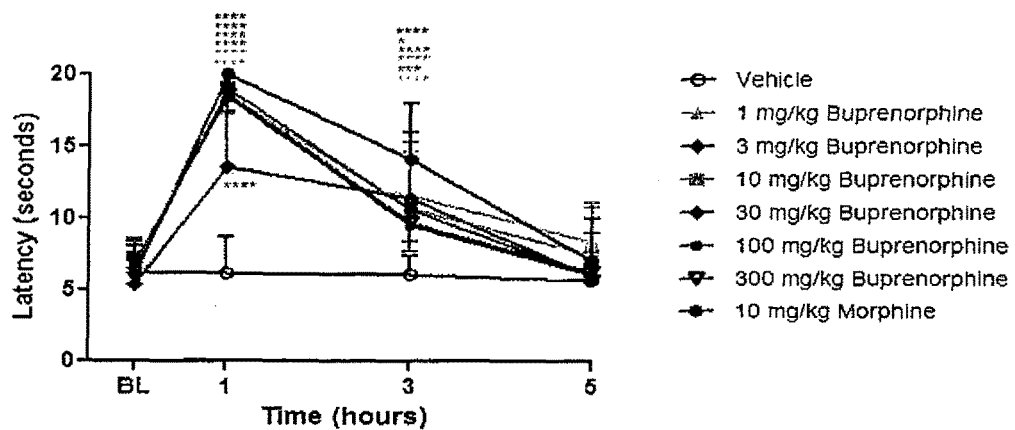

Results shown in FIG. 6C demonstrate that buprenorphine mitigates acute pain at MED<1 mg/kg PO.

Example 7

The Effect of Oxycodone on GI Transit

Example 7A

Subjects: male Sprague-Dawley rats, 207-255 g; n=10/group.

Morphine sulfate (10 mg/kg), oxycodone hydrochloride (0.3-5 mg/kg), or saline (vehicle) were administered SC 0.5 hour (morphine) or 1 hour (oxycodone, vehicle) prior to the PO administration of a charcoal meal (1 ml/100 grams). One hour later, the rats were euthanized by $CO_2$ and the gastrointestinal tract was removed from the stomach to the cecum. The length of the small intestine and the distance (cm) to the leading edge of charcoal were recorded. Data were analyzed using a one-way ANOVA followed by the Dunnett's Multiple Comparisons test where ***P<0.001. Data are represented as the mean+S.E.M.

Figure 7A:
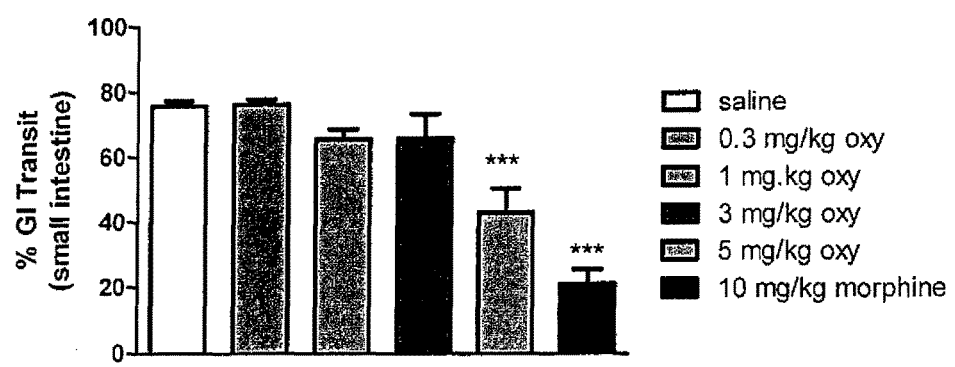
FIGS. 7A, 7B, 7C and 7D are graphical depictions of the results of Example 7.

The results shown in FIG. 7A demonstrate that oxycodone decreases gastrointestinal transit as evidenced by the decreased % of the small intestine traveled by a charcoal meal following oxycodone treatment as compared to vehicle treated animals. This effect was dose dependent with a greater magnitude of effect observed with increasing dose.

Example 7B

Test subjects: male Sprague-Dawley rats, 207-255 g; n=10/group.

Morphine sulfate, the positive control, oxycodone HCl, or saline (vehicle) were administered SC either 0.5 hr (morphine) or 1 hour (oxycodone, vehicle) prior to the PO administration of a charcoal meal (1 ml/100 grams). One hour later, rats were euthanized by $CO_2$ and the GI tract was removed from the stomach to the cecum. The length of the small intestine and the distance (cm) to the leading edge of charcoal was recorded. Data were analyzed using a one-way ANOVA followed by the Dunnett's Multiple Comparisons test where ***P<0.001. Data are represented as the mean+S.E.M.

Figure 7B:
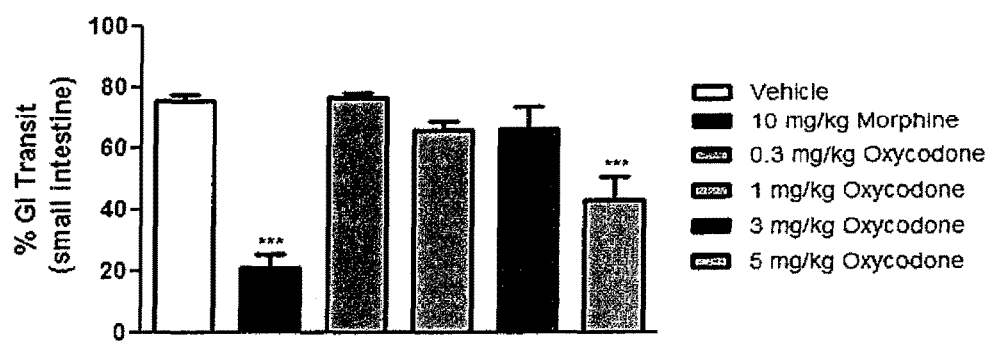

The results are shown in FIG. 7B.

Example 7C

Test subjects: male Sprague-Dawley rats, 225-255 g; n=10/group.

Oxycodone HCl, or water (vehicle) were administered PO, while morphine sulfate, the positive control, was administered SC, either 0.5 hr (morphine) or 1 hour (oxycodone HCl, vehicle) prior to the PO administration of a charcoal meal (1 ml/100 grams). One hour later, rats were euthanized by $CO_2$ and the GI tract was removed from the stomach to the cecum. The length of the small intestine and the distance (cm) to the leading edge of charcoal was recorded. Data were analyzed using a one-way ANOVA followed by the Dunnett's Multiple Comparisons test where P<0.01 and *P<0.001. Data are represented as the mean+S.E.M.

Figure 7C:
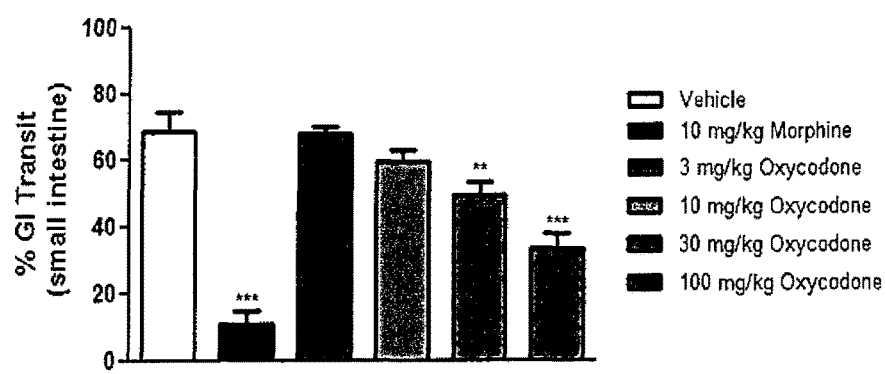

The results are shown in FIG. 7C.

Example 7D

Test subjects: male Sprague-Dawley rats, 197-252 g on the day of testing; n=9-11/group.

Rats were dosed with Oxycodone HCl/Oxy or vehicle (water) PO once daily for 5 days (chronic). Additional groups were dosed only once on day 5 (acute). One hour after the oxy dosing, a PO administration of a charcoal meal (1 ml/100 grams) was given. One hour after charcoal, all rats were euthanized by $CO_2$ and the GI tract was removed from the stomach to the cecum. The length of the small intestine and the distance (cm) to the leading edge of charcoal was recorded. Data were analyzed using a one-way ANOVA with Bonferonni's Multiple Comparison Test where * P<0.05, ****P<0.0001 vs. vehicle (chronic), ### vs. oxycodone (acute). Data are represented as the means+S.E.M.

Figure 7D:
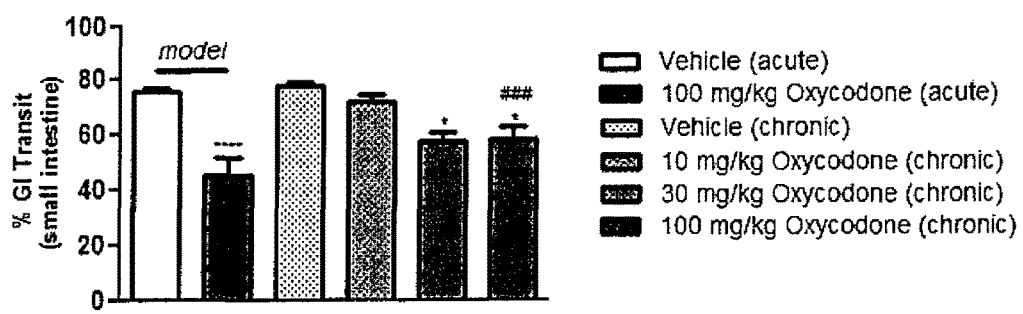

The results shown in FIG. 7D demonstrate that repeated oxycodone dosing produces some tolerances to its acute effect on the inhibition of GI transit.

Example 8

The Effect of Oxycodone in Response Latency in a Rat Hot Plate Assay

Example 8A

Subjects: male Sprague-Dawley rats, 234-279 g; n=10/group.

Oxycodone hydrochloride (0.3-5 mg/kg) was dissolved in 0.9% normal saline solution (NSS) (vehicle) and administered SC 1 hour prior to testing against vehicle. Hot plate was set to 52° C. and cutoff was 30 seconds. Data were analyzed by a two-way ANOVA using a Bonferroni multiple comparisons test, where ****P<0.0001. Data are represented as the means+S.E.M.

Figure 8A:
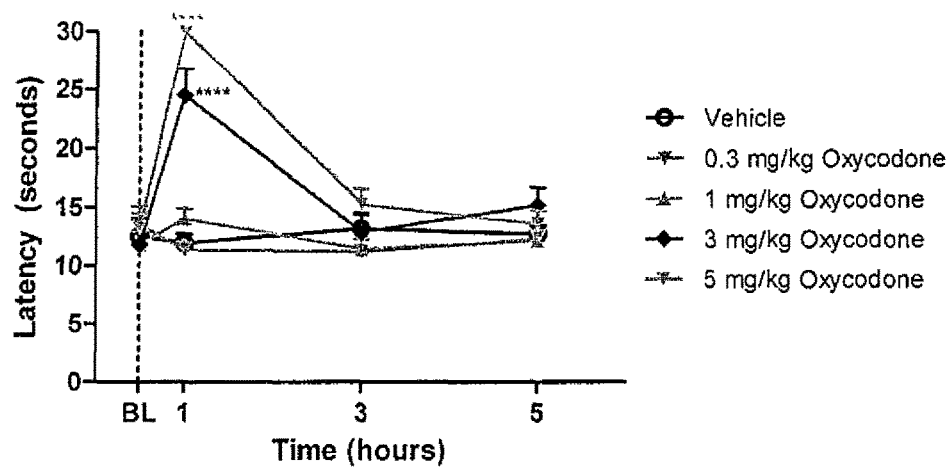
FIGS. 8A, 8B, 8C and 8D are graphical depictions of the results of Example 8.

The results shown in FIG. 8A demonstrate that oxycodone provides analgesia as evidenced by increased latency to nocifensive response. This effect was dose dependent with a greater magnitude of effect observed with increasing dose.

Example 8B

Subjects: male Sprague-Dawley rats, 234-279 g; n=10/group. Compound was administered SC 1 hour prior to testing. Oxycodone hydrochloride (0.3-5 mg/kg) was dissolved in 0.9% normal saline solution (NSS) (vehicle) and administered SC 1 hour prior to testing against vehicle. Hot plate was set to 52° C. and cutoff was 30 seconds. % MPE=. Percent Maximum Possible Effect. % MPE=(test latency-baseline)/(cutoff (30 s)-baseline). Data were analyzed by a two-way ANOVA using Bonferroni Multiple Comparisons test for post-hoc analysis, ****P<0.000. Data are represented as the means+SEM.

Figure 8B:
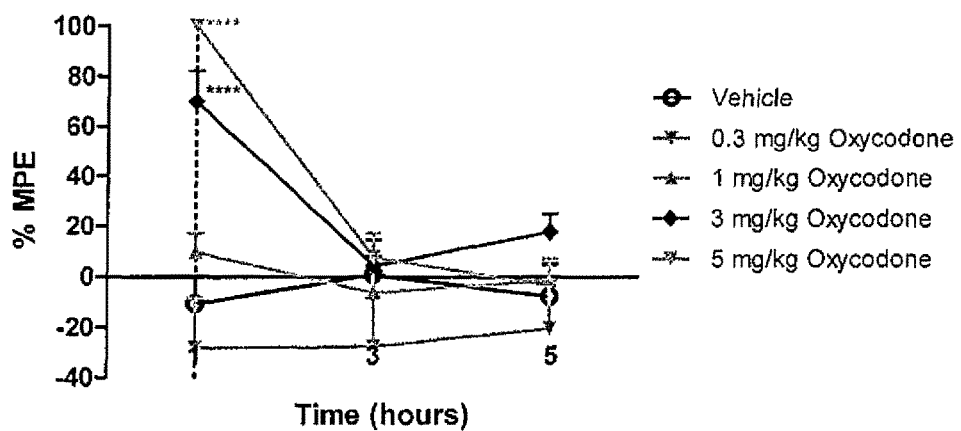

The results shown in FIG. 8B demonstrate that oxycodone provides analgesia as evidenced by increased % of the maximal possible effect (a normalized transformation of the latency to nocifensive response). This effect was dose dependent with a greater magnitude of effect observed with increasing dose.

Example 8C

Test subjects: male Sprague-Dawley rats, 200-230 g; n=10/group

Oxycodone HCl was administered SC 1 hour prior to testing. Thermal latency was assessed the day prior (BL) and then 1, 3 and 5 hours post-oxycodone dosing. The hotplate was set to 52° C. and the cutoff was 30 seconds. Oxycodone was dissolved in 0.9% NS (vehicle). Note: at 10 mg/kg, 4 out of 10 were found dead at the 3 hr time point. Data were analyzed by a two-way ANOVA using the Bonferroni Multiple Comparisons test for post-hoc analysis where, ***P<0.001. Data are represented as the means+SEM.

Figure 8C:
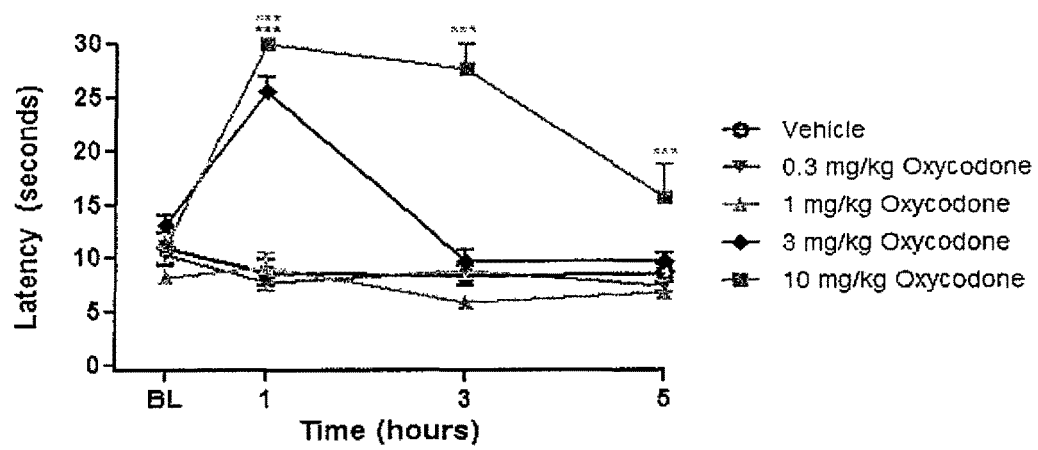

The results shown in FIG. 8C demonstrate that oxycodone mitigates acute pain in the rat; MED=3 mg/kg SC.

Example 8D

Subjects: male Sprague-Dawley rats, 226-251 g; n=10/group.

Oxycodone HCl was administered PO 1 hour prior to testing, while morphine sulfate, the positive control, was administered SC 1 hour prior to testing. Behavior was assessed the day prior (BL) and then 1, 3, 5 and 24 hours post-compound administration. The hot plate was set to 52° C. and the cutoff was 30 seconds. Oxycodone was dissolved in water (vehicle), while morphine sulfate was dissolved in 0.9% NS. Data were analyzed by a two-way ANOVA using a Bonferroni Multiple Comparisons Test, where ****P<0.0001.

Figure 8D:
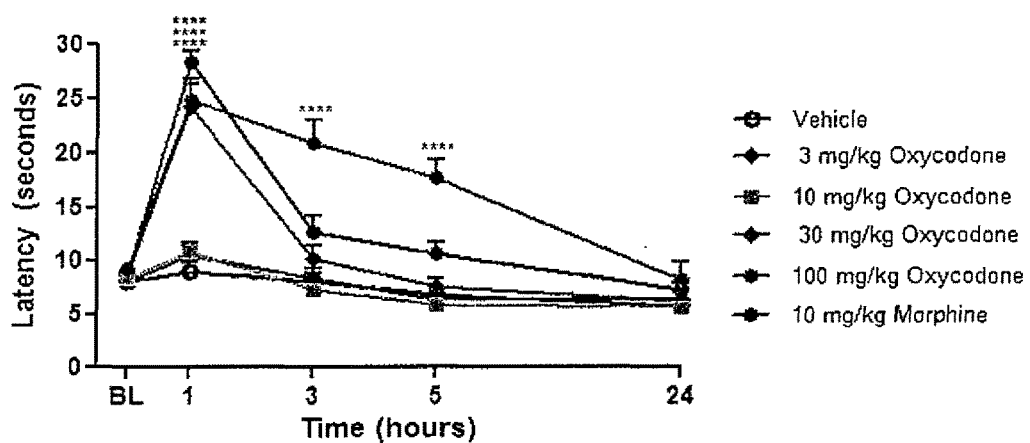

The results shown in FIG. 8D demonstrate that oxycodone mitigates acute pain in the rat; MED=10 mg/kg PO.

Example 9

The Effect of Oxycodone in Response Latency in a Rat Tail Flick Assay

Example 9A

Subjects: male Sprague-Dawley rats, 234-279 g; n=10/group.

Oxycodone hydrochloride (0.3-5 mg/kg) was dissolved in 0.9% normal saline solution (NSS) (vehicle) and administered SC 1 hour prior to testing against vehicle. Data were analyzed by a two-way ANOVA using a Bonferroni multiple comparisons test, ****P<0.001.

Figure 9A:
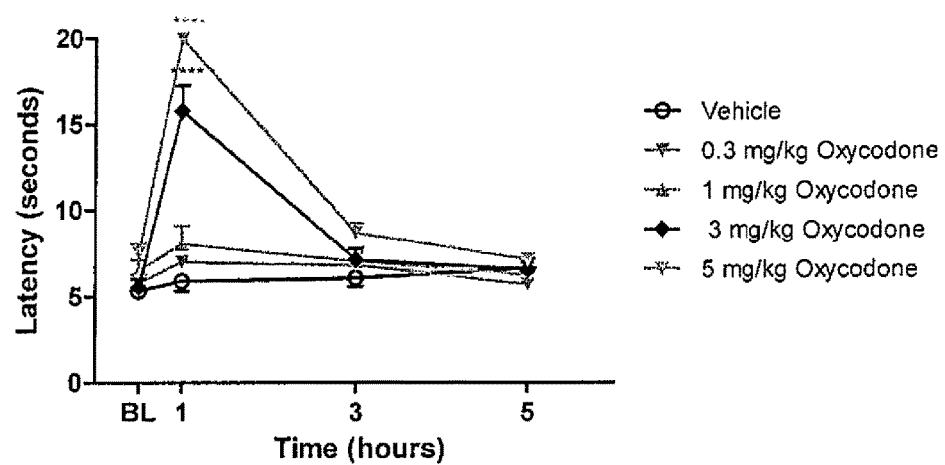
FIGS. 9A, 9B and 9C are graphical depictions of the results of Example 9.

The results shown in FIG. 9A demonstrate that oxycodone provides analgesia as evidenced by increased latency to nocifensive response. This effect was dose dependent with a greater magnitude of effect observed with increasing dose.

Example 9B

Subjects: male Sprague-Dawley rats, 234-279 g; n=10/group.

Oxycodone hydrochloride (0.3-5 mg/kg) was dissolved in 0.9% normal saline solution (NSS) (vehicle) and administered SC 1 hour prior to testing against vehicle. % MPE=Percent Maximum Possible Effect. % MPE=(test latency-baseline)/(cutoff(20 s)-baseline)*100. Data were analyzed by a two-way ANOVA using a Bonferroni multiple comparisons test, ****P<0.001.

Figure 9B:
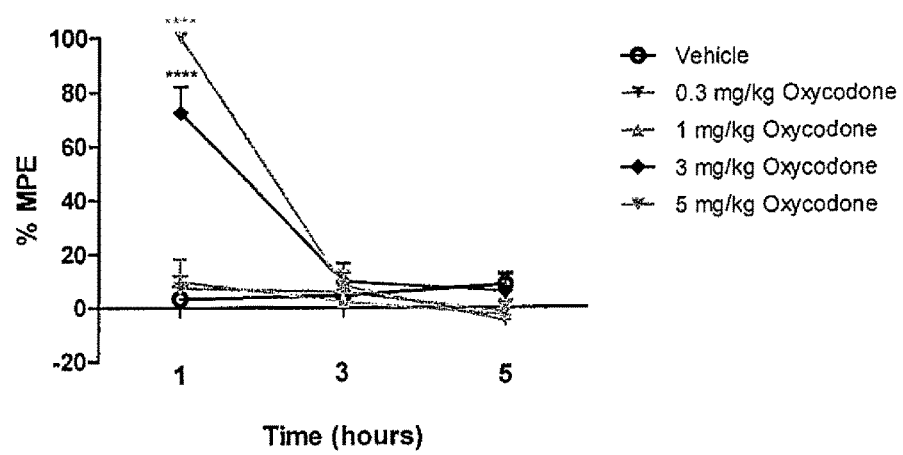

The results shown in FIG. 9B demonstrate that oxycodone provides analgesia as evidenced by increased % of the maximal possible effect (a normalized transformation of the latency to nocifensive response). This effect was dose dependent with a greater magnitude of effect observed with increasing dose.

Example 9C

Test subjects: male Sprague-Dawley rats, 200-230 g; n=10/group.

Oxycodone HCl and vehicle were administered SC 1 hour prior to testing. Rats were assessed one day prior (BL) and then 1, 3 and 5 hours post-oxycodone administration. The tail flick was set to an intensity of 40 and the cutoff was 20 seconds. Oxycodone was dissolved in 0.9% (vehicle). Note: for the 10 mg/kg dosing group, 4 out of 10 rats were found dead at the 3 hr time point. Data were analyzed by a two-way ANOVA followed by the Bonferroni Multiple Comparisons Test where, *P<0.05 and ****P<0.001.

Figure 9C:
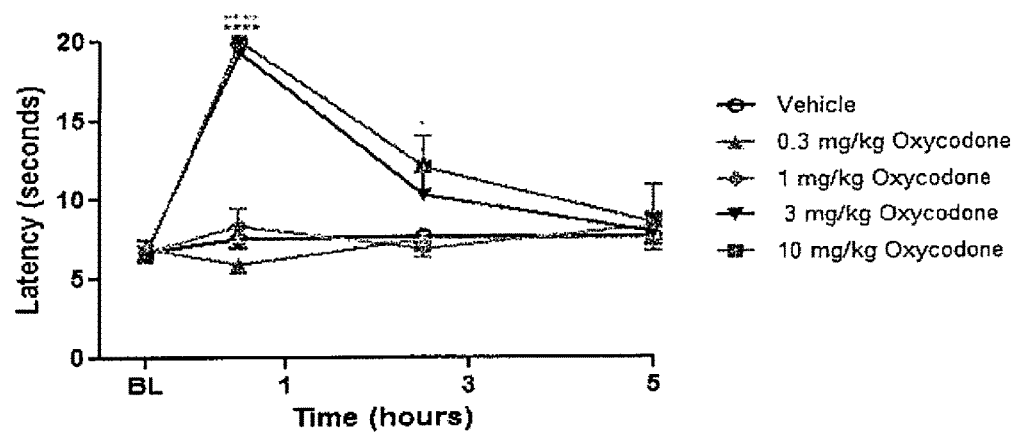

The results shown in FIG. 9C demonstrate that oxycodone mitigates acute pain in the rat, MED=3 mg/kg SC.

Example 9D

Test subjects: male Sprague-Dawley rats, 226-251 g; n=10/group.

Oxycodone HCl was administered PO 1 hour prior to testing, while morphine sulfate, the positive control, was administered SC 1 Hour prior to testing. Behavior was assessed the day prior (BL) to dosing, and then 1, 3, 5 and 24 hours post-compound administration. The tail flick was set to an intensity of 40 and 20 seconds was used as the cutoff. Oxycodone was dissolved in water (vehicle), while morphine was dissolved in 0.9% NS. Data were analyzed by a two-way ANOVA using a Bonferroni Multiple Comparisons Test, where *P<0.05, P<0.01, *P<0.001 and ****P<0.0001.

The results shown in FIG. 9D demonstrate that oxycodone mitigates acute pain in the rat; MED=10 mg/kg PO.

Example 10

The Effect of Buprenorphine on Morphine-Induced Inhibition of GI Transit

Test subjects: male Sprague-Dawley rats, 220-240 g; n=8-21/group.

Buprenorphine free base (0.0005-1 mg/kg) (Bup) or 25% hydroxylpropyl-beta-cyclodextrin (HPBCD; vehicle) was administered SC to the test subjects. 1 hour later, a SC dose of 10 mg/kg morphine sulfate or saline was administered. 0.5 hour after morphine or saline injection, the test subjects were given a PO administration of a charcoal meal (1 ml/100 grams).

Figure 10:
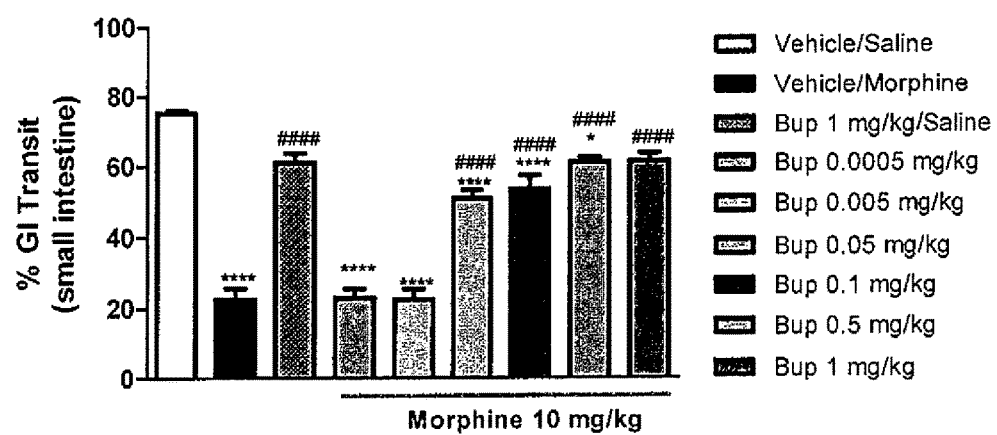
FIG. 10 is a graphical depiction of the results of Example 10.

One hour after the charcoal meal, the test subjects were euthanized by CO2 and the GI tract was removed from the stomach to the cecum. The length of the small intestine and the distance (cm) to the leading edge of the charcoal were recorded. Data were analyzed using a one-way ANOVA with Bonferroni's multiple comparisons test. *P<0.05, ***P<0.001 vs. vehicle/saline and ###P<0.001 vs. vehicle/morphine. Data are represented as the means+S.E.M. The results shown in FIG. 10 demonstrate that buprenorphine when administered prior to morphine prevents the morphine induced retardation of GI transit. This effect was dose dependent with a greater magnitude of effect observed with increasing dose.

Example 11

The Effect of Buprenorphine on Morphine Co-Administration on Rat GI Transit

Test subjects: male Sprague-Dawley rats, 226-260 g; n=10/group.

Buprenorphine free base (0.0005-1 mg/kg) (Bup) or 25% hydroxylpropyl-beta-cyclodextrin (HPBCD; vehicle) was administered SC to the test subjects immediately prior to a SC dose of 10 mg/kg morphine sulfate or saline (co-administration; different sites). 0.5 hour after morphine injection, the test subjects were given a PO administration of a charcoal meal (1 ml/100 grams).

Figure 11:
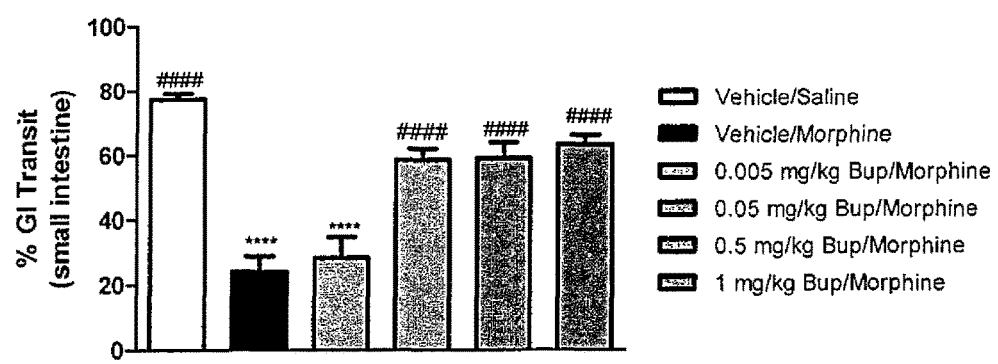
FIG. 11 is a graphical depiction of the results of Example 11.

One hour after the charcoal meal, the test subjects were euthanized by CO2 and the GI tract was removed from the stomach to the cecum. The length of the small intestine and the distance (cm) to the leading edge of the charcoal were recorded. Data were analyzed using a one-way ANOVA with Bonferroni's multiple comparisons test. *P<0.05, ****P<0.0001 vs. vehicle/saline and ####P<0.0001 vs. vehicle/morphine. Data are represented as the means+S.E.M. The results shown in FIG. 11 demonstrate that buprenorphine when co-administered with morphine prevents the morphine induced retardation of GI transit. This effect was dose dependent with a greater magnitude of effect observed with increasing dose.

Example 12

The Effect of Buprenorphine and Morphine in Response Latency in a Rat Hot Plate Assay Example 12A Subjects: male Sprague-Dawley rats, 220-243 g; n=10/group.

Buprenorphine free base (0.005-1 mg/kg) was formulated in 25% HPBCD (vehicle) while morphine sulphate (10 mg/kg), the positive control, was dissolved in 0.9% NSS (vehicle). Buprenorphine free base (0.005-1 mg/kg) was administered SC 1 hour prior to morphine sulfate (10 mg/kg). Rats were assessed for thermal latency the day prior to dosing, then 1.5, 3 and 5 hours post-morphine administration. Data were analyzed by a two-way ANOVA using the Bonferroni Multiple Comparisons Test, where ****P<0.0001 compared to vehicle+vehicle. Data are represented as the means+S.E.M.

Figure 12A:
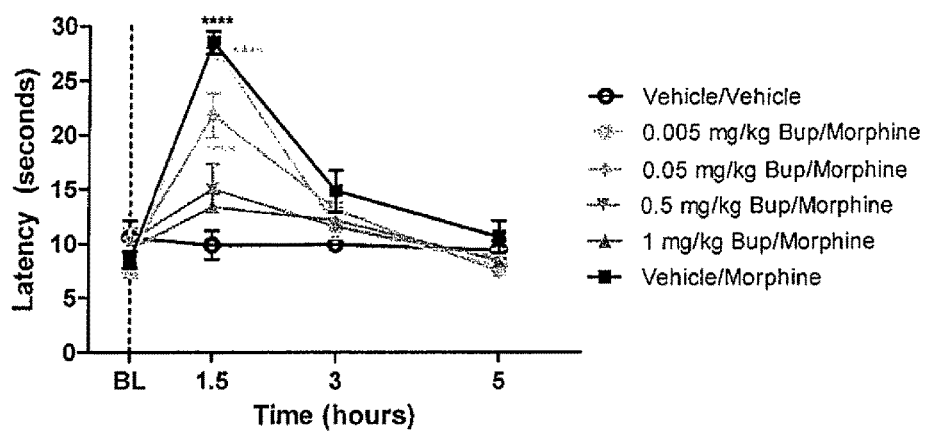
FIGS. 12A and 12B are graphical depictions of the results of Example 12.

The results shown in FIG. 12A demonstrate that buprenorphine when administered prior to morphine produces some erosion of the analgesic efficacy of morphine, as evidenced by a statistically significant reduction in latency to nocifensive response as compared to morphine alone. This effect was dose dependent with a greater magnitude of effect observed with increasing dose.

Example 12B

Subjects: male Sprague-Dawley rats, 220-243 g; n=10/group.

Buprenorphine free base (0.005-1 mg/kg) was formulated in 25% HPBCD (vehicle) while morphine sulphate (10 mg/kg), the positive control, was dissolved in 0.9% NSS (vehicle). Buprenorphine free base (0.005-1 mg/kg), was administered SC 1 hour prior to morphine sulfate (10 mg/kg). Rats were assessed for thermal latency 1.5, 3 and 5 hours post-morphine administration. % MPE=Percent Maximum Possible Effect. % MPE=(test latency-baseline)/(cutoff (30 s)-baseline). Data were analyzed by a two-way ANOVA using Bonferroni Multiple Comparisons test for post-hoc analysis, where P<0.01 and **P<0.0001. Data are represented as the means+SEM.

Figure 12B:
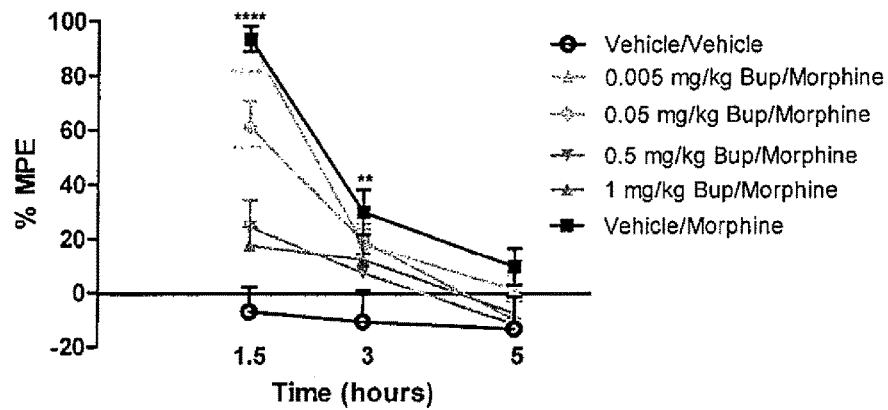

The results shown in FIG. 12B demonstrate that buprenorphine administered prior to morphine produces some erosion of the analgesic efficacy of morphine, as evidenced by a statistically significant reduction in the % of the maximum possible effect (a normalized transformation of the latency to nocifensive response) as compared to morphine alone. This effect was dose dependent with a greater magnitude of effect observed with increasing dose.

Example 13

The Effect of Buprenorphine and Morphine in Response Latency in a Rat Tail Flick Assay Example 13A Subjects: male Sprague-Dawley rats, 198-243 g; n=10/group.

Buprenorphine free base (0.005-1 mg/kg) was formulated in 25% HPBCD (vehicle) while morphine sulphate (10 mg/kg), the positive control, was dissolved in 0.9% NSS (vehicle). Buprenorphine free base (0.005-1 mg/kg), was administered SC 1 hour prior to, morphine sulfate (10 mg/kg). Rats were assessed for tail flick latency the day prior to dosing, then 1.5, 3 and 5 hours post-morphine administration. Data were analyzed by a two-way ANOVA using the Bonferroni Multiple Comparisons Test, where ****P<0.0001 compared to vehicle+vehicle. Data are represented as the means+S.E.M.

Figure 13A:
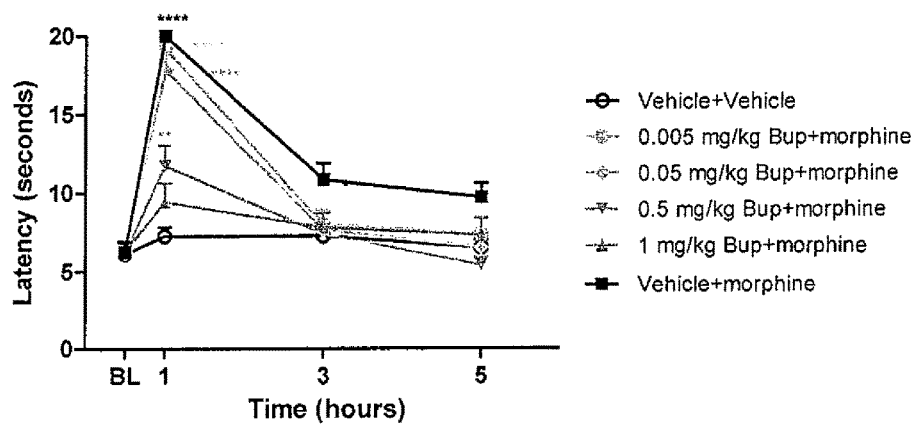
FIGS. 13A and 13B are graphical depictions of the results of Example 13.

The results shown in FIG. 13A demonstrate that buprenorphine when administered prior to morphine produces some erosion of the analgesic efficacy of morphine, as evidenced by a statistically significant reduction in latency to nocifensive response as compared to morphine alone. This effect was dose dependent with a greater magnitude of effect observed with increasing dose.

Example 13B

Subjects: male Sprague-Dawley rats, 198-243 g; n=10/group.

Buprenorphine free base (0.005-1 mg/kg) was formulated in 25% HPBCD (vehicle) while morphine sulphate (10 mg/kg), the positive control, was dissolved in 0.9% NSS (vehicle). Buprenorphine free base (0.005-1 mg/kg), was administered SC 1 hour prior to morphine sulfate (10 mg/kg). Rats were assessed for thermal latency 1.5, 3 and 5 hours post-morphine administration. % MPE=Percent Maximum Possible Effect. % MPE=(test latency-baseline)/(cutoff (20 s)-baseline)*100. Data were analyzed by a two-way ANOVA using a Bonferroni multiple comparisons test for post-hoc analysis where *P<0.05 and ****P<0.001. Data are represented as the means+SEM.

Figure 13B:
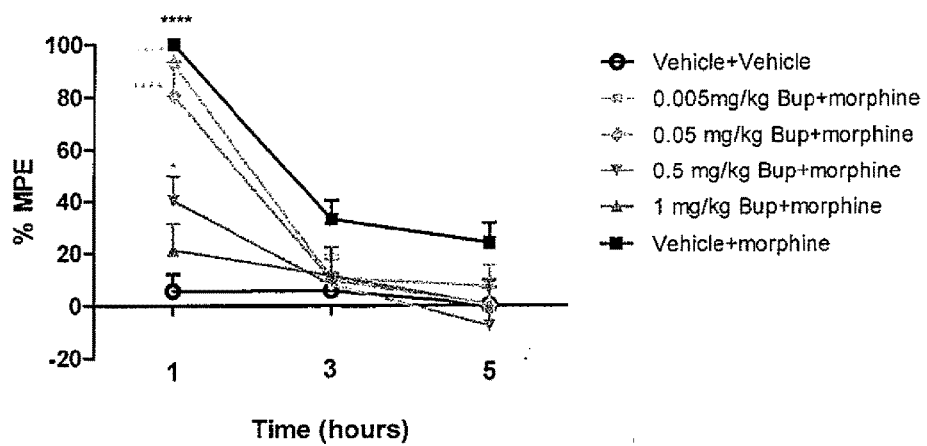

The results shown in FIG. 13B demonstrate that buprenorphine administered prior to morphine produces some erosion of the analgesic efficacy of morphine, as evidenced by a statistically significant reduction in the % of the maximum possible effect (a normalized transformation of the latency to nocifensive response) as compared to morphine alone. This effect was dose dependent with a greater magnitude of effect observed with increasing dose.

Example 14

The Effect of Buprenorphine and Oxycodone on GI Transit

Example 14A

Subjects: male Sprague-Dawley rats, 211-236 g; n=10/group.

Rats were dosed with buprenorphine free base (0.005-0.5 mg/kg) or vehicle (25% HPBCD) SC 1 hour prior to an SC dose of 8 mg/kg oxycodone hydrochloride, 10 mg/kg morphine sulphate, or vehicle (0.9% saline). 0.5 hr (in the case of morphine) or 1 hour (other treatments) later the rats received PO administration of a charcoal meal (1 ml/100 grams). One hour after charcoal administration, all rats were euthanized by CO2 and the GI tract was removed from the stomach to the cecum. The length of the small intestine and the distance (cm) to the leading edge of charcoal were recorded. Data were analyzed using a one-way ANOVA with Bonferonni's Post-Test where $P<0.01$, **$P<0.0001$ vs. vehicle and ####$P<0.0001$ vs. vehicle+oxycodone. Data are represented as the means+S.E.M.

Figure 14A:
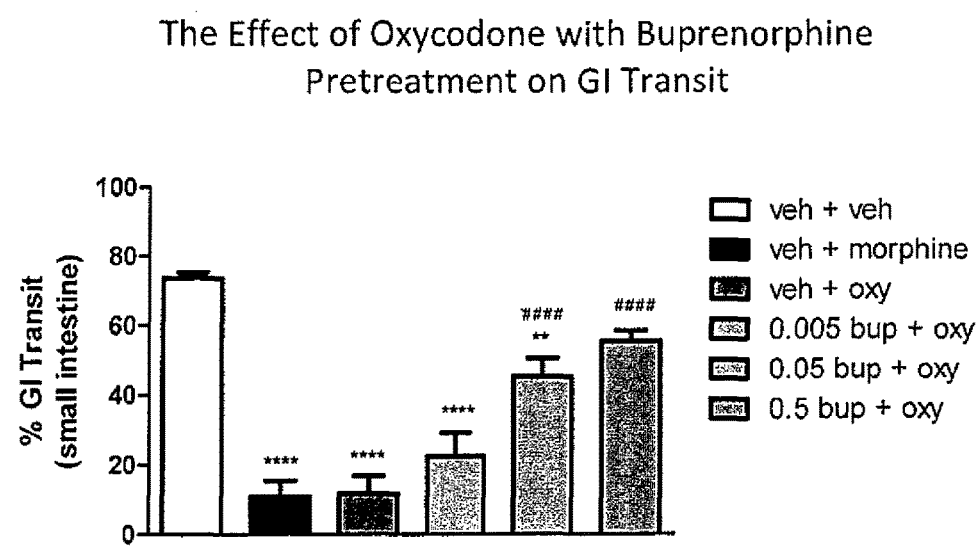
FIGS. 14A and 14B are graphical depictions of the results of Example 14.

The results shown in FIG. 14A demonstrate that buprenorphine when administered prior to oxycodone prevents the oxycodone induced retardation of GI transit. This effect was dose dependent with a greater magnitude of effect observed with increasing dose. Buprenorphine displays a higher potency (i.e. significant effects observed at lower doses) against oxycodone induced retardation of GI transit as compared to morphine induced retardation of GI transit.

Example 14B

Subjects: male Sprague-Dawley rats, 211-236 g; n=10/group.

Rats were dosed with buprenorphine free base (0.5-3) or vehicle (25% HPBCD) SC 1 hour prior to an SC dose of 8 mg/kg oxycodone hydrochloride, 10 mg/kg morphine sulphate, or vehicle (0.9% saline). 0.5 hr (in the case of morphine) or 1 hour (other treatments) later the rats received PO administration of a charcoal meal (1 ml/100 grams). One hour after charcoal administration, all rats were euthanized by CO2 and the GI tract was removed from the stomach to the cecum. The length of the small intestine and the distance (cm) to the leading edge of charcoal were recorded. Data were analyzed using a one-way ANOVA with Bonferonni's PostTest where $P<0.01$, **$P<0.0001$ vs. vehicle and ####$P<0.0001$ vs. vehicle+oxy. Data are represented as the means+S.E.M.

Figure 14B:
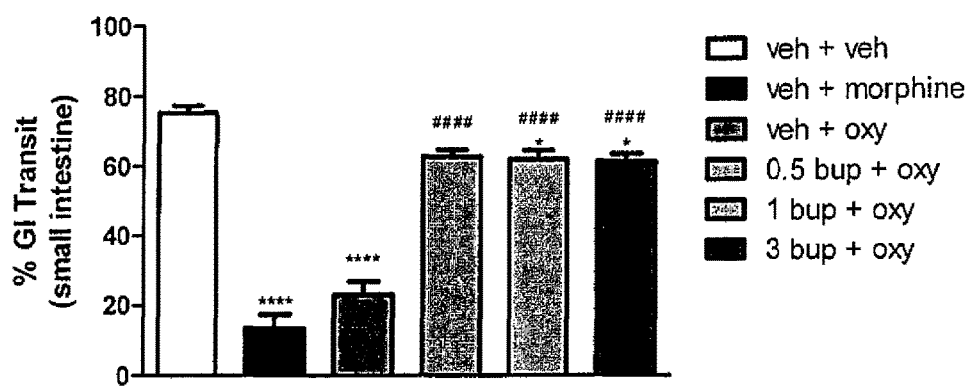

The results shown in FIG. 14B demonstrate that buprenorphine when administered prior to oxycodone prevents the oxycodone induced retardation of GI transit. A "ceiling effect" was observed whereby increasing doses of buprenorphine did not produce greater magnitude of effects.

Example 15

The Effect of PO Buprenorphine on Oxycodone-Induced Inhibition on Rat GI Transit Test subjects: male Sprague-Dawley rats, 224-253 g; n=10 or 11/group.

Buprenorphine free base (30-300 mg/kg) (Bup) or 25% hydroxylpropyl-beta-cyclodextrin (HPBCD; vehicle) was orally administered to the test subjects one hour prior to an oral administration of 100 mg/kg oxycodone or water. One hour after the oral oxycodone administration, the test subjects were given a PO administration of a charcoal meal (1 ml/100 grams).

One hour after the charcoal meal, the test subjects were euthanized by CO2 and the GI tract was removed from the stomach to the cecum. The length of the small intestine and the distance (cm) to the leading edge of the charcoal were recorded. Data were analyzed using a one-way ANOVA with Bonferroni's Post-Test where *$P<0.05$, $P<0.01$, *$P<0.001$ and ****$P<0.0001$ vs. veh+veh, and ####$P<0.0001$ vs. veh+oxycodone. Data are represented as the means+S.E.M.

Figure 15:
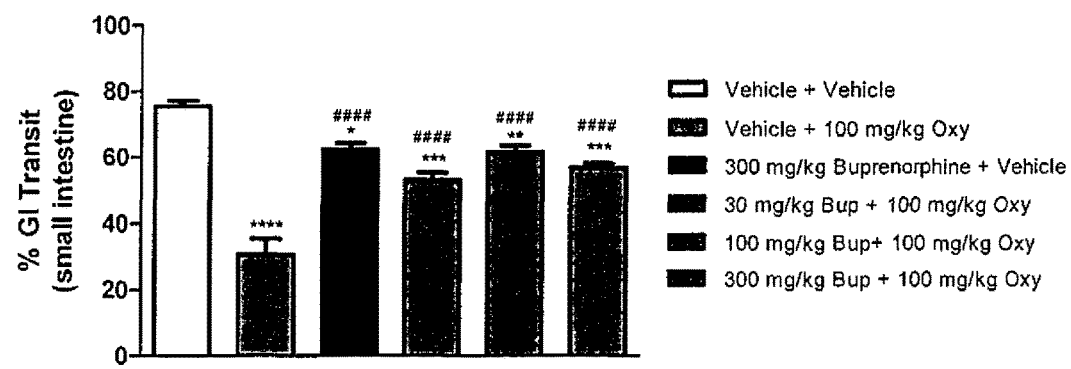
FIG. 15 is a graphical depiction of the results of Example 15.

The results are shown in FIG. 15.

Example 16

The Effect of Oral PO Buprenorphine and Oral Oxycodone Dosing on Rat GI Transit

Test subjects: male Sprague-Dawley rats, 226-265 g; n=10/group.

Buprenorphine free base (3-30 mg/kg) (Bup) or 25% hydroxylpropyl-beta-cyclodextrin (HPBCD; vehicle) was orally administered to the test subjects one hour prior to an oral administration of 100 mg/kg oxycodone or water. One hour after the oral oxycodone administration, the test subjects were given a PO administration of a charcoal meal (1 ml/100 grams).

One hour after the charcoal meal, the test subjects were euthanized by CO2 and the GI tract was removed from the stomach to the cecum. The length of the small intestine and the distance (cm) to the leading edge of the charcoal were recorded. Data were analyzed using a one-way ANOVA with Bonferroni's Post-Test where * $P<0.05$, $P<0.01$, **$P<0.0001$ vs. vehicle+vehicle and #$P<0.05$ vs. veh+Oxy. Data are represented as the means+S.E.M.

Figure 16:
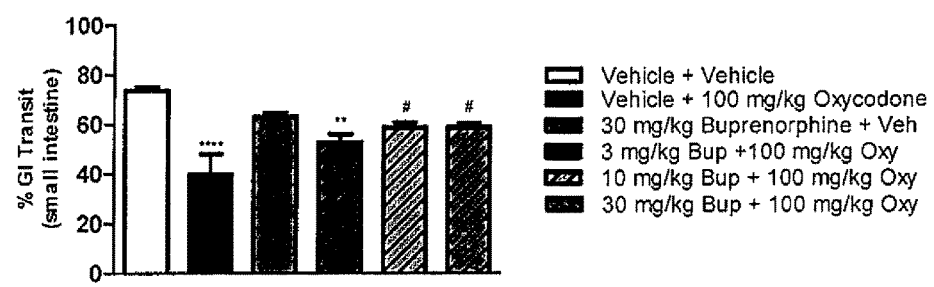
FIG. 16 is a graphical depiction of the results of Example 16.

The results are shown in FIG. 16.

Example 17

The Effect of Buprenorphine and Oxycodone in Response Latency in a Rat Hot Plate Assay Example 17A Subjects: male Sprague-Dawley rats, 227-252 g; n=10/group.

Figure 17A:
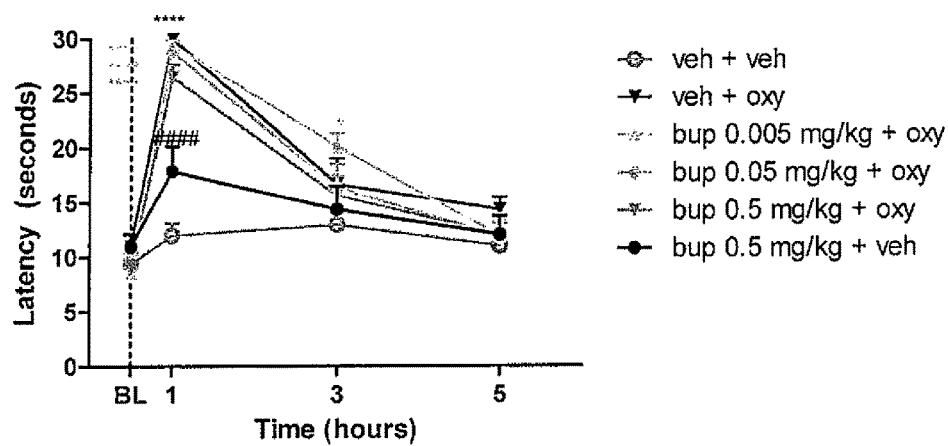
FIGS. 17A and 17B is a graphical depiction of the results of Example 17.

Buprenorphine free base (0.005-1 mg/kg) or vehicle (25% HPBCD) were administered SC 1 hour prior to a SC injection of 8 mg/kg oxycodone or vehicle (0.9% saline). Rats were tested 1 hour after oxycodone injection. Hot plate was set to 52° C. and cutoff was 30 seconds. Data were analyzed by a two-way ANOVA using a Bonferroni multiple comparisons test, where ####$P<0.0001$ vs. veh+oxy. All oxy-dosed groups were significantly different from vehicle+vehicle at 1 hour ($P<0.0001$) and *$P<0.05$ at 3 hours. Data are represented as the means+S.E.M The results shown in FIG. 17A demonstrate that buprenorphine when administered prior to oxycodone does not produces erosion of the analgesic efficacy of oxycodone, as evidenced by a lack of statistically significant reduction in latency to nocifensive response as compared to oxycodone alone. Importantly the same dose range was effective in prevention of oxycodone induced retardation of GI transit.

Example 17B

Subjects: male Sprague-Dawley rats, 227-252 g; n=10/group.

Buprenorphine free base (0.005-0.5 mg/kg) or vehicle (25% HPBCD) were administered SC 1 hour prior to a SC injection of oxycodone or vehicle (0.9% saline). Rats were tested 1 hour after oxycodone injection. Hot plate was set to 52° C. and cutoff was 30 seconds.

% MPE=Percent Maximum Possible Effect. % MPE=(test latency-baseline)/(cutoff (30 s)-baseline). Data were analyzed by a two-way ANOVA using a Bonferroni multiple comparisons test, where ####P<0.0001 vs. vehicle+oxycodone. ****<P 0.0001 significantly different from veh+veh at 1 hour (P<0.0001). Data are represented as the means+S.E.M.

Figure 17B:
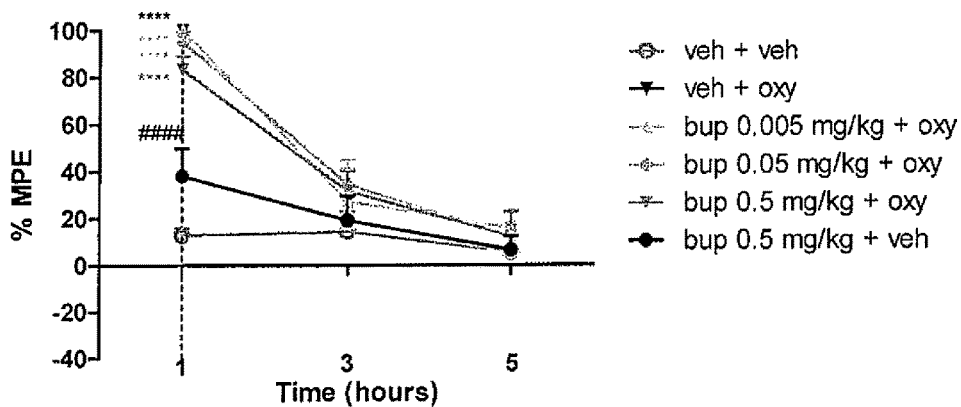

The results shown in FIG. 17B demonstrate that buprenorphine when administered prior to oxycodone does not produces erosion of the analgesic efficacy of oxycodone, as evidenced by a lack of statistically significant reduction in the % of the maximum possible effect (a normalized transformation of the latency to nocifensive response) as compared to oxycodone alone. Importantly the same dose range was effective in prevention of oxycodone induced retardation of GI transit.

Example 18

The Effect of Buprenorphine and Oxycodone in Response Latency in a Tail Flick Assay Example 18A Subjects: male Sprague-Dawley rats, 209-242 g; n=10/group.

Buprenorphine free base (0.005-0.5 mg/kg) or vehicle (25% HPBCD) were administered SC 1 hour prior to a SC injection of 8 mg/kg oxycodone or vehicle (0.9% saline). Rats were tested 1 hour after oxycodone injection. Tail Flick was set to 40 Intensity and cutoff was 20 seconds. Data were analyzed by a two-way ANOVA using a Bonferroni multiple comparisons test, where ##P<0.0001 vs. veh+oxy. ****P<0.0001 were significantly different from vehicle+vehicle at 1 hour. Data are represented as the means+S.E.M.

Figure 18A:
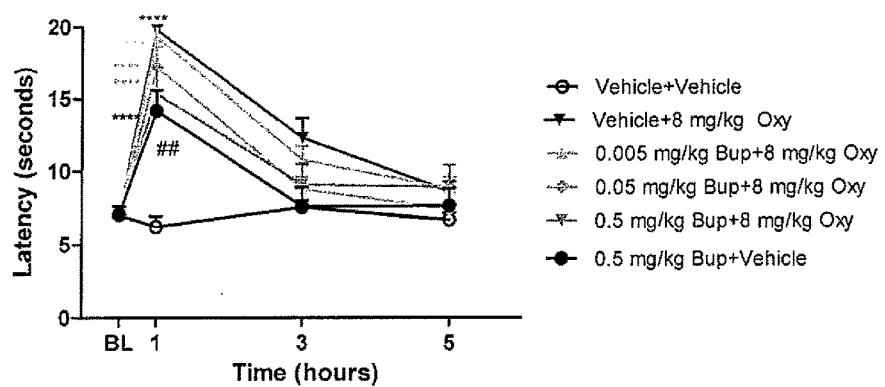
FIGS. 18A and 18B are graphical depictions of the results of Example 18.

The results shown in FIG. 18A demonstrate that buprenorphine when administered prior to oxycodone does not produces erosion of the analgesic efficacy of oxycodone, as evidenced by a lack of statistically significant reduction in latency to nocifensive response as compared to oxycodone alone. Importantly the same dose range was effective in prevention of oxycodone induced retardation of GI transit.

Example 18B

Subjects: male Sprague-Dawley rats, 227-252 g; n=10/group.

Buprenorphine free base (0.005-0.5 mg/kg) or vehicle (25% HPBCD) were administered SC 1 hour prior to a SC injection of oxycodone or vehicle (0.9% saline). Rats were tested 1 hour after oxycodone injection. Tail Flick was set to 40 Intensity and cutoff was 20 seconds.

% MPE=Percent Maximum Possible Effect. % MPE=(test latency-baseline)/(cutoff (30 s)-baseline). Data were analyzed by a two-way ANOVA using a Bonferroni multiple comparisons test, where #P<0.05 vs. vehicle+oxycodone and ****P, 0.0001 vs. vehicle+vehicle. Data are represented as the means+S.E.M.

Figure 18B:
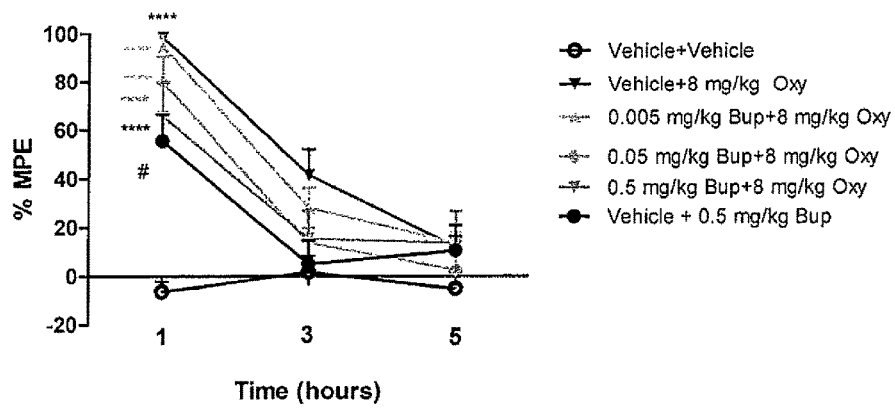

The results shown in FIG. 18B demonstrate that buprenorphine when administered prior to oxycodone does not produces erosion of the analgesic efficacy of oxycodone, as evidenced by a lack of statistically significant reduction in the % of the maximum possible effect (a normalized transformation of the latency to nocifensive response) as compared to oxycodone alone. Importantly the same dose range was effective in prevention of oxycodone induced retardation of GI transit.

Example 19

The Effect of Buprenorphine and Oxycodone Co-Administration on Acute Analgesia

Example 19A

Test subjects: Male Sprague-Dawley rats, 209-242 g, n=10/group

Oxycodone HCl (8 mg/kg), buprenorphine free base (0.005 mg/kg-0.5 mg/kg) (Bup) or 25% hydroxylpropyl-beta-cyclodextrin/saline (HPBCD/saline; vehicle) were co-administered subcutaneously (SC) albeit at different sites. Rats were assessed one day prior (BL) and then 1, 3, and 5 hours post co-administration. Tail Flick was set to 40 Intensity and cutoff was 20 seconds. Data was analyzed by a two-way ANOVA using a Bonferroni multiple comparisons test, where all groups were significantly different from veh+veh at 1 hour, ****P<0.0001. Data are represented as the means+S.E.M.

Figure 19A:
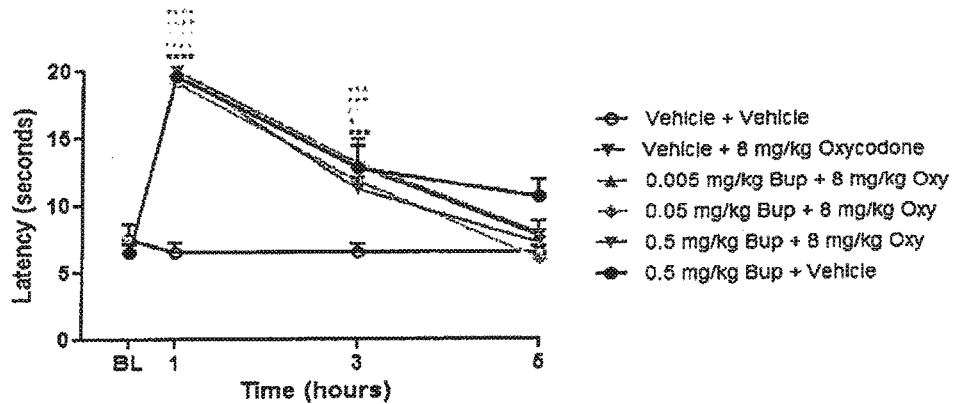
FIGS. 19A and 19B are graphical depictions of the results of Example 19.

The results shown in FIG. 19A demonstrate that buprenorphine pretreatment does not attenuate the analgesic effect of 8 mg/kg oxycodone.

Example 19B

Oxycodone HCl (8 mg/kg), buprenorphine free base (0.005 mg/kg-0.5 mg/kg) (Bup) or 25% hydroxylpropyl-beta-cyclodextrin/saline (HPBCD/saline; vehicle) were co-administered subcutaneously (SC) albeit at different sites. Rats were assessed one day prior (BL) and then 1, 3, and 5 hours post co-administration. Hot plate was set to 52° C. and cutoff was 30 seconds. Data was analyzed by a two-way ANOVA using a Bonferroni multiple comparisons test, where all groups were significantly different from veh+veh at 1 hour, ****P<0.0001 and ####P<0.0001 and ###P<0.001 vs. veh+8 mg/kg Oxycodone. Data are represented as the means+S.E.M.

Figure 19B:
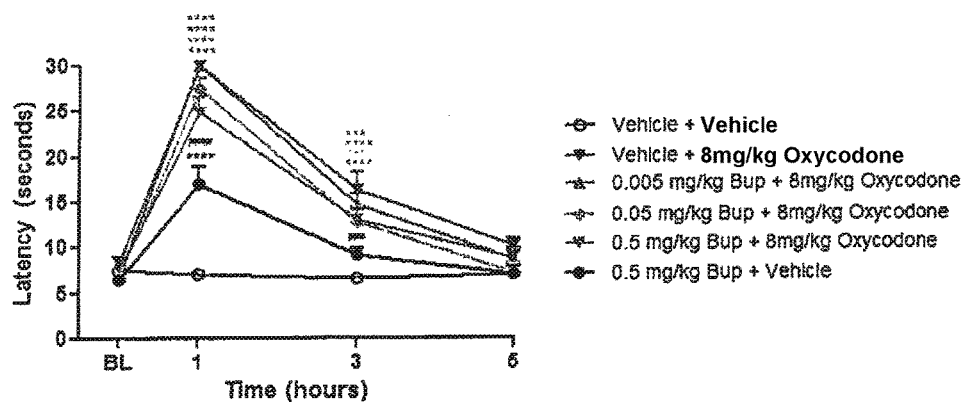

The results shown in FIG. 19B demonstrate that buprenorphine pretreatment does not attenuate the analgesic effect of 8 mg/kg oxycodone.

Example 20

The Effect of Buprenorphine Pretreatment on Oxycodone-Induced Inhibition of GI Transit in the Rat Test subjects: Male Sprague-Dawley rats, 211-236 g, n=10-20/group Rats were dosed with buprenorphine free base (0.005 mg/kg-3 mg/kg) (Bup) or 25% hydroxylpropyl-beta-cyclodextrin (HPBCD vehicle), 10 mg/kg morphine, or vehicle (0.9% saline), ½ hour (in the case of morphine) or 1 hour (all other treatments) later, the rats received a charcoal meal PO (1 ml/100 g). One hour after charcoal, all rats were euthanized by $CO_2$ and the GI tract was removed from the stomach to the cecum. The length of the small intestine and the distance (cm) to the leading edge of charcoal was recorded. Data were analyzed using a one-way ANOVA with Bonferroni Post-Test, where P<0.01, **P<0.0001 vs. veh+veh, and ####P<0.0001 vs. veh+oxycodone. Data are represented as the means+S.E.M.

Figure 20:
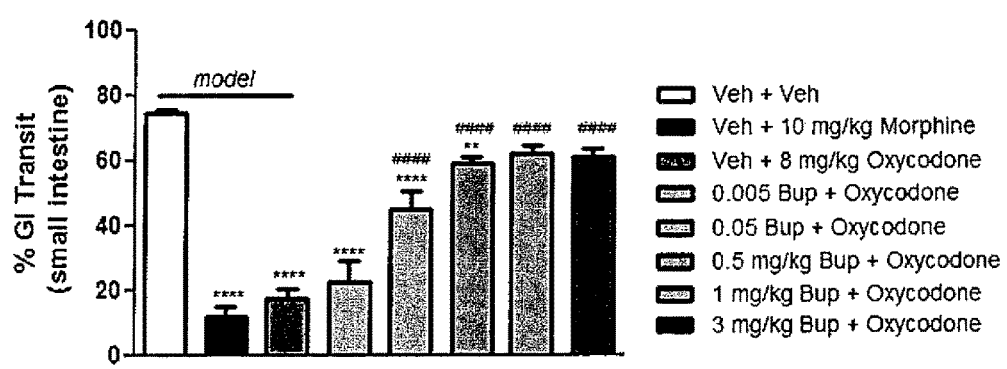
FIG. 20 is a graphical depiction of the results of Example 20.

The results shown in FIG. 20 demonstrate that 0.05 mg/kg SC buprenorphine attenuates the constipating effect of SC oxycodone.

Example 21

The Effect of Buprenorphine+Oxycodone SC Co-Administration on GI Transit in the Rat Test subjects: Male Sprague-Dawley rats, 211-236 g, n=10-20/group Oxycodone or vehicle (25% HPBCD) were administered SC immediately prior to SC buprenorphine; BUP or saline (co-admin; different sites). One hour later, rats were given a PO administration of a charcoal meal (1 ml/100 grams). One hour after charcoal, all rats were euthanized by CO2 and the GI tract was removed from the stomach to the cecum. The length of the small intestine and the distance (cm) to the leading edge of charcoal were recorded. Subjects: male Sprague-Dawley rats, 226-258 g; n=10/group. Data were analyzed using a one-way ANOVA with Bonferonni's Post-Test where *P<0.001, and **P<0.0001 vs. veh+veh and ###P<0.001, ####P<0.0001 vs. veh+oxycodone. Data are represented as the means+S.E.M.

Figure 21:
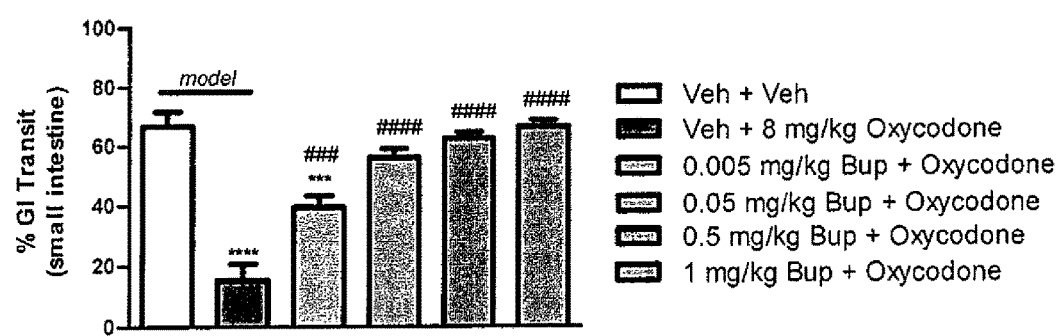
FIG. 21 is a graphical depiction of the results of Example 21.

The results shown in FIG. 21 demonstrate that when co-Administered, 0.005 mg/kg SC buprenorphine can attenuate the constipating effect of SC oxycodone.

Example 22

The Summarized Effect of Buprenorphine PO Pre-Treatment on Oxycodone-Induced Inhibition of GI Transit in the Rat Test subjects: male Sprague-Dawley rats, 223-250 g; n=10-41/group (4 studies combined).

Rats were dosed PO with Buprenorphine/Bup or vehicle (25% HPBCD) PO. One hour later they were dosed PO with Oxycodone/Oxy or vehicle (water). One hour after Oxy or veh, a PO administration of a charcoal meal (1 ml/100 grams) was given. One hour after charcoal, all rats were euthanized by CO2 and the GI tract was removed from the stomach to the cecum. The length of the small intestine and the distance (cm) to the leading edge of charcoal was recorded. Data were analyzed using a one-way ANOVA with Bonferonni's Multiple Comparison Test, where *P<0.05, P<0.01, *P<0.001 vs. vehicle+vehicle and #P<0.05, ##P<0.01, ###P<0.001, ####P<0.0001 vs. vehicle+100 mg/kg oxycodone. Data are represented as the means+S.E.M.

Figure 22:
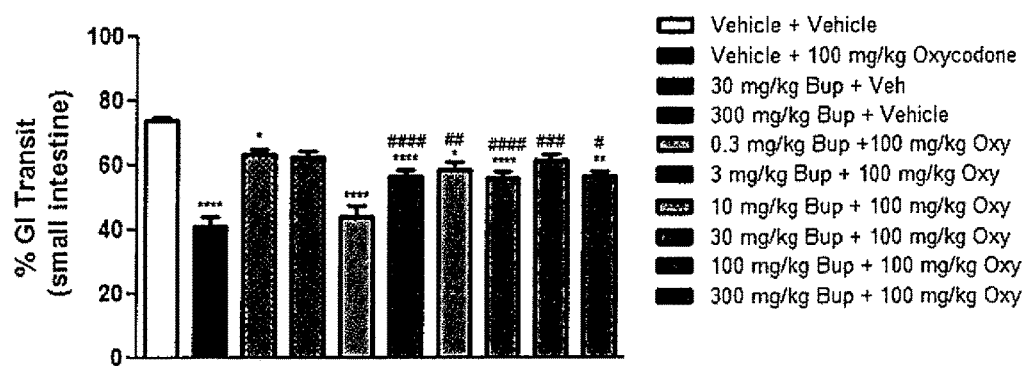
FIG. 22 is graphical depiction of the results of Example 22.

The results shown in FIG. 22 demonstrate that 3 mg/kg is the lowest PO dose that attenuates the constipating effect of oral oxycodone (combined data sets).

Example 23

The Effect of a Single Bup Administration on Oxycodone-Induced Attenuation of GI Transit in the Rat Following Repeated Oxycodone Dosing Test subjects: male Sprague-Dawley rats, 203-253 g on the day of testing; n=9-0/group.

Rats were dosed once daily for 5 days with Oxycodone/Oxy or saline SC. On the 5th day, Buprenorphine/Bup or vehicle (25% HPBCD) was administered SC at the same time as the last oxycodone dose. One hour later, a PO administration of a charcoal meal (1 ml/100 grams) was given. One hour after charcoal, all rats were euthanized by CO2 and the GI tract was removed from the stomach to the cecum. The length of the small intestine and the distance (cm) to the leading edge of charcoal was recorded. Data were analyzed using a one-way ANOVA with Bonferonni's Multiple Comparisons Test where P<0.01, **P<0.0001 vs. vehicle+vehicle and #P<0.05 vs. veh+Oxy. Data are represented as the means+S.E.M.

Figure 23:
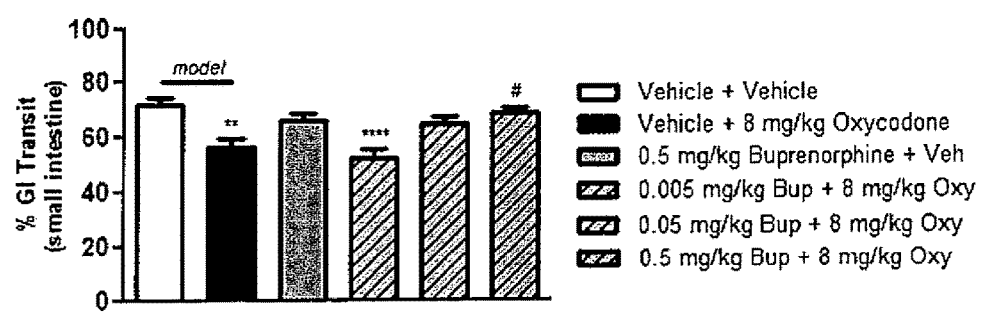
FIG. 23 is a graphical depiction of the results of Example 23.

The results shown in FIG. 23 demonstrate that acute 0.5 mg/kg SC buprenorphine administration reverses oxycodone-induced inhibition of GI Transit.

Example 24

The Effect of Repeated Buprenorphine and Oxycodone SC Administration (Co-Administration) on GI Transit in the Rat Test subjects: male Sprague-Dawley rats, 202-250 g on the day of testing; n=9-11/group.

Rats were co-dosed for 5 days with Oxycodone/Oxy or water and Buprenorphine/Bup or vehicle (25% HPBCD) SC. One hour after the 5th dose of each, a PO administration of a charcoal meal (1 ml/100 grams) was given. One hour after charcoal, all rats were euthanized by CO2 and the GI tract was removed from the stomach to the cecum. The length of the small intestine and the distance (cm) to the leading edge of charcoal was recorded. Data were analyzed using a one-way ANOVA with Bonferonni's Multiple Comparison Test where P<0.01, **P<0.0001 vs. vehicle+vehicle and #P<0.05, ####P<0.0001 vs. veh+Oxy. Data are represented as the means+S.E.M.

Figure 24:
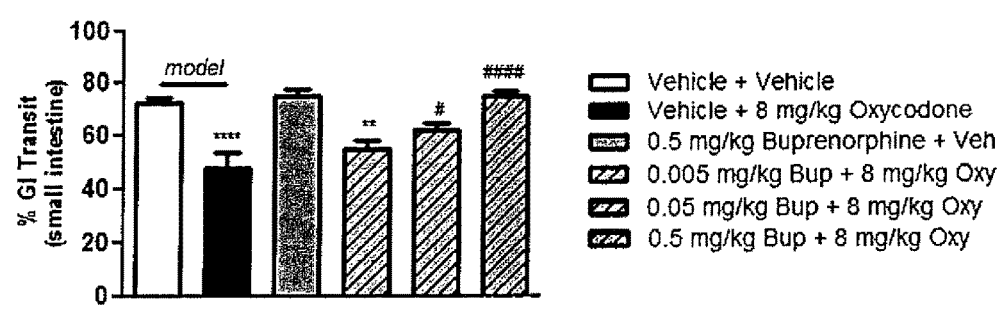
FIG. 24 is a graphical depiction of the results of Example 24.

The results shown in FIG. 24 demonstrate that repeated dosing with SC buprenorphine×5 days lowers the MED needed to attenuate the effect of oxycodone on GI Transit (0.05 mg vs. 0.5 mg/kg).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

We claim:

1. A method of preventing or treating an opioid-induced adverse pharmacodynamic response comprising:
    concurrently administering to a patient in need thereof an effective amount of an opioid agonist selected from the group consisting of oxycodone, morphine, codeine, oxymorphone, fentanyl, hydrocodone, hydromorphone, tramadol, and a pharmaceutically acceptable salt thereof to provide an analgesic effect and an effective amount of buprenorphine to prevent or treat an adverse pharmacodynamic response induced by the administration of the opioid agonist,
    wherein the buprenorphine is sub-analgetic and does not affect the analgesic effect of the opioid agonist.

2. The method of claim 1, wherein the administration of the opioid agonist is initiated prior to administration of the buprenorphine.

3. The method of claim 2, wherein the patient initiates administration of the opioid agonist on a chronic basis prior to administration of the buprenorphine.

4. The method of claim 3, wherein the patient exhibits the opioid-induced adverse pharmacodynamic response prior to administration of the buprenorphine.

5. The method of claim 4, wherein the administration of the buprenorphine treats the opioid induced adverse pharmacodynamic response induced by the opioid agonist.

6. The method of claim 1, wherein the patient is opioid naive.

7. The method of claim 1, wherein the patient is administered the opioid agonist on a chronic basis.

8. The method of claim 1, wherein the administration of the buprenorphine is initiated prior to initiating the administration of the opioid agonist.

9. The method of claim 1, wherein the opioid agonist has an $E_{max}$ of greater than about 25%.

10. The method of claim 1, wherein the buprenorphine is selected from the group consisting of buprenorphine base, a pharmaceutically acceptable salt thereof, and a mixture thereof.

11. The method of claim 1, wherein the buprenorphine is administered by the same route as the opioid agonist.

12. The method of claim 11, wherein the opioid agonist and the buprenorphine are each administered by a route selected from the group consisting of oral, transdermal, sublingual, buccal, gingival, rectal, subcutaneous, intramuscular, intravenous and parenteral.

13. The method of claim 1, wherein the buprenorphine is administered by a different route than the opioid agonist.

14. The method of claim 13, wherein the buprenorphine and the opioid agonist are administered by different routes independently selected from the group consisting of oral, transdermal, sublingual, buccal, gingival, rectal, subcutaneous, intramuscular, intravenous and parenteral.

15. A pharmaceutical unit dosage form comprising:
(i) an effective amount of an opioid agonist selected from the group consisting of oxycodone, morphine, codeine, oxymorphone, fentanyl, hydrocodone, hydromorphone, tramadol and a pharmaceutically acceptable salt thereof to provide an analgesic effect, and
(ii) an effective amount of buprenorphine to prevent or treat an adverse pharmacodynamic response induced by the opioid,
wherein the buprenorphine is sub-analgetic and does not affect the analgesic effect of the opioid agonist.

16. A kit comprising:
(i) a unit dose of an effective amount of an opioid agonist selected from the group consisting of oxycodone, morphine, codeine, oxymorphone, fentanyl, hydrocodone, hydromorphone, tramadol and a pharmaceutically acceptable salt thereof to provide an analgesic effect, and
(ii) a unit dose of an effective amount of buprenorphine to prevent or treat an opioid-induced adverse pharmacodynamic response induced by the opioid agonist, wherein the buprenorphine is sub-analgetic and does not affect the analgesic effect of the opioid agonist.

* * * * *